US012736527B2

(12) United States Patent
Muotri et al.

(10) Patent No.: US 12,736,527 B2
(45) **Date of Patent: *Sep. 15, 2026**

(54) FUNCTIONAL CORTICAL ORGANOIDS, METHODS OF MAKING, AND USES THEREOF

(71) Applicant: The Regents of the University of California, Oakland, CA (US)

(72) Inventors: Alysson Renato Muotri, La Jolla, CA (US); Priscilla Davidson Negraes, San Diego, CA (US); Cleber Trujillo, San Diego, CA (US); Pinar Mesci, Carlsbad, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/378,530

(22) Filed: Oct. 10, 2023

(65) Prior Publication Data

US 2024/0264152 A1 Aug. 8, 2024

Related U.S. Application Data

(62) Division of application No. 16/634,140, filed as application No. PCT/US2018/043983 on Jul. 26, 2018, now Pat. No. 11,821,895.

(60) Provisional application No. 62/537,368, filed on Jul. 26, 2017.

(51) Int. Cl.
*C12N 5/0789* (2010.01)
*G01N 33/50* (2006.01)

(52) U.S. Cl.
CPC ....... *G01N 33/5058* (2013.01); *C12N 5/0647* (2013.01); *G01N 33/5011* (2013.01); *C12N 2501/115* (2013.01); *C12N 2501/15* (2013.01); *C12N 2501/155* (2013.01)

(58) Field of Classification Search
CPC ........... G01N 33/5058; G01N 33/5011; C12N 5/0619; C12N 5/0623; C12N 2501/115; C12N 2501/01; C12N 2501/13; C12N 5/0662–0668; C12N 5/0696; C12N 2501/15; C12N 2501/155; C12N 5/0647
See application file for complete search history.

(56) References Cited

U.S. PATENT DOCUMENTS

2018/0282689 A1 10/2018 Andersen
2018/0298330 A1 10/2018 Bolognin
2019/0345439 A1 11/2019 Skardal

OTHER PUBLICATIONS

Burotto et al., "Brain metastasis in patients with adrenocortical carcinoma: a clinical series", J. Clin. Endocrinol Metab., Feb. 2015, vol. 100, No. 2, pp. 331-336.
Fukusumi et al., "Establishment of Human Neural Progenitor Cells from Human Induced Pluripotent Stem Cells with Diverse Tissue Origins", Stem Cells Int., 2016, vol. 2016, p. 7235757.
Gemini-Bioproducts, Gem21 NeuroPlex Serum-Free Supplement Solution, Feb. 29, 2012 [the date is according to the document properties for the posted document] [online].Retrieved from the Internet Sep. 24, 2018: <https://www.gembio.com/sites/main/files/file-attachments/400-160_gem21_product_usage_0.pdf>.
Gem21 NeuroPlex(TM) without Vitamin A Serum-Free Supplement, Material Safey Data Sheet, Gemini Bio-Products, Apr. 8, 2011.
GLUTAMAX(TM), Product Information Sheet, GIBCO, ThermoFisher Scientific, Nov. 4, 2020.
Krausz et al., "Translation of a tumor microenvironment mimicking 3D tumor growth co-culture assay platform to high-content screening," J Biomol Screen, Jan. 2013, vol. 18, No. 1, pp. 54-66.
Lancaster et al., "Generation of cerebral organoids from human pluripotent stem cells" Nature Protocols, Oct. 2014, vol. 9, No. 10, pp. 2329-2340.
Liu et al., "Nonviral Reprogramming Genes Accelerate Formation of Neurons from Murine Embryonic Brain Cells: Synergistic Effect of Brain Derived Neurotrophic Factor Gene Therapy," Transl Med (Sunnyvale) 2016, vol. 6, No. 1, pp. 1-8.
Nickitas-Etienne, Athina, International Preliminary Report on Patentability and Written Opinion, The International Bureau of WIPO, PCT/US18/43983, Feb. 6, 2020.
Quadrato et al., "Cell diversity and network dynamics in photosensitive human brain organoids," Nature, May 4, 2017, vol. 545, No. 7652, pp. 48-53.
Young, Lee W., International Search Report and Written Opinion, United States Patent and Trademark Office, PCT/US18/43983, Jan. 3, 2019.

*Primary Examiner* — David W Berke-Schlessel
*Assistant Examiner* — Trent R Clarke
(74) *Attorney, Agent, or Firm* — McKee, Voorhees & Sease, PLC

(57) ABSTRACT

The disclosure provides methods of making functional cortical organoids from somatic cells and stem cells and methods of using the functional organoids.

14 Claims, 48 Drawing Sheets

Specification includes a Sequence Listing.

2 months

DAPI/Nestin/β-Catenin/MAP2

DAPI/SOX2/CTIP2/MAP2

DAPI/NeuN/Ki67/MAP2

DAPI/NeuN/Ki67

4 months

DAPI/TBR1/CTIP2/SOX2

DAPI/GFAP/CTIP2/MAP2

DAPI/SATB2/CTIP2/SOX2

DAPI/SOX/NeuN/MAP2

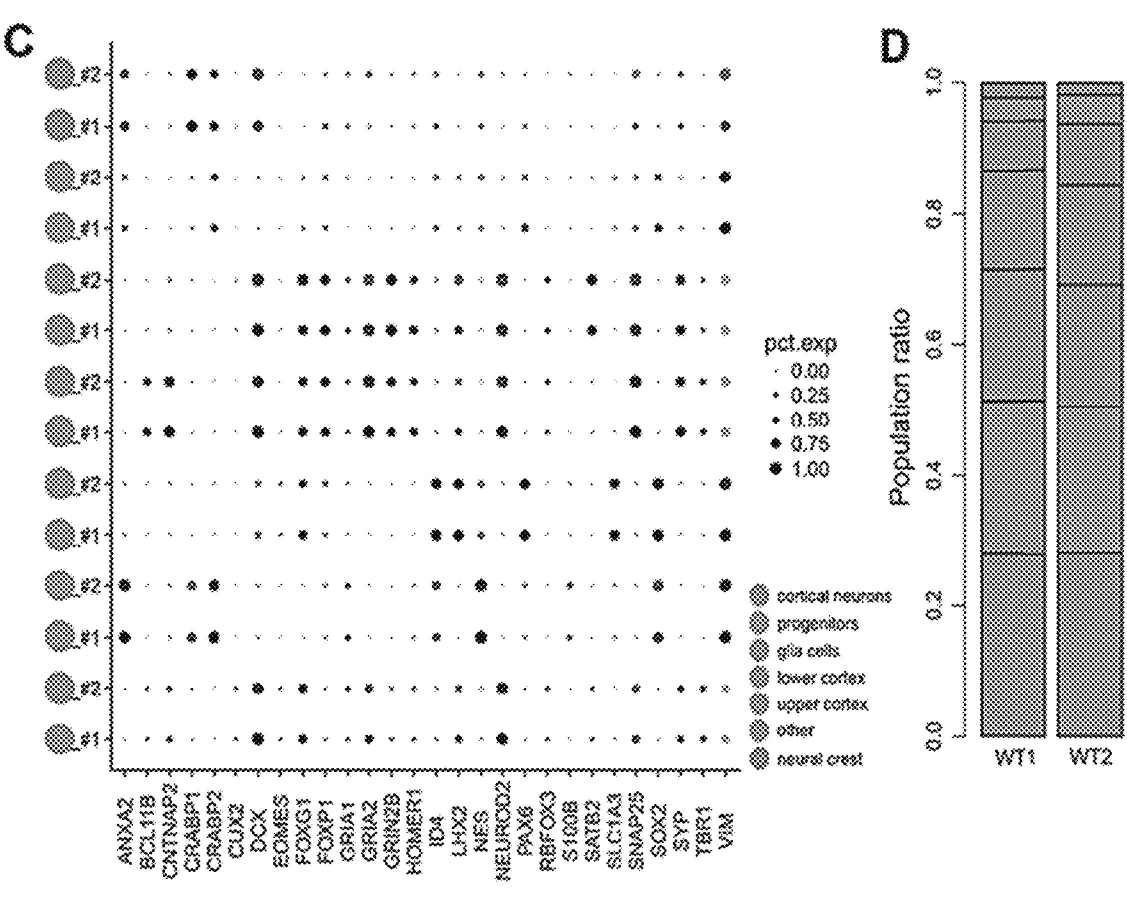
*FIG. 2C-D*
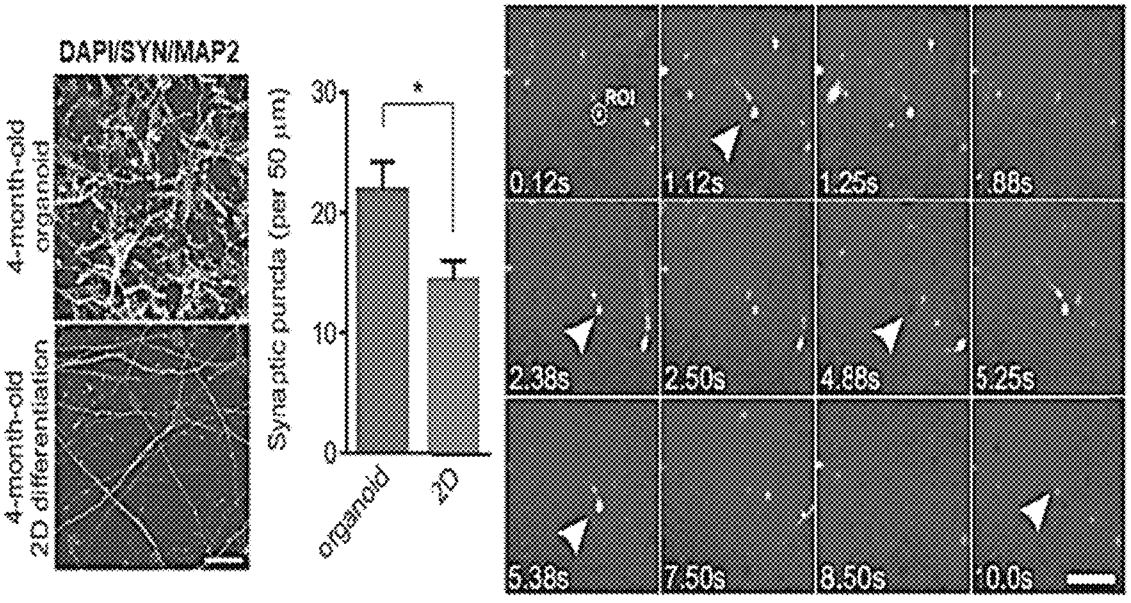
*FIG. 3A*
*FIG. 3B*

FIG. 4E-F

Cortical organoids and iPSC-derived neurons

Spike rate (spike/s)

1500
1000
500
10
5
0

Amin et al. 2016 (64)
Odawara et al. 2014 (62)
Odawara et al. 2016 (63)
Marchetto et al. 2017 (61)
Xu et al. 2017 (54)
Quadrato et al. 2017 (24)
Nageshappa et al. 2016 (51)
Vessoni et al. 2016 (59)
Chailangham et al. 2016 (53)
Tukker et al. 2016 (57)
Bardy et al. 2015 (58)
Quadrato et al., 2017 (24)

8
12
16
20
24
28
32
36
40

Time (weeks)

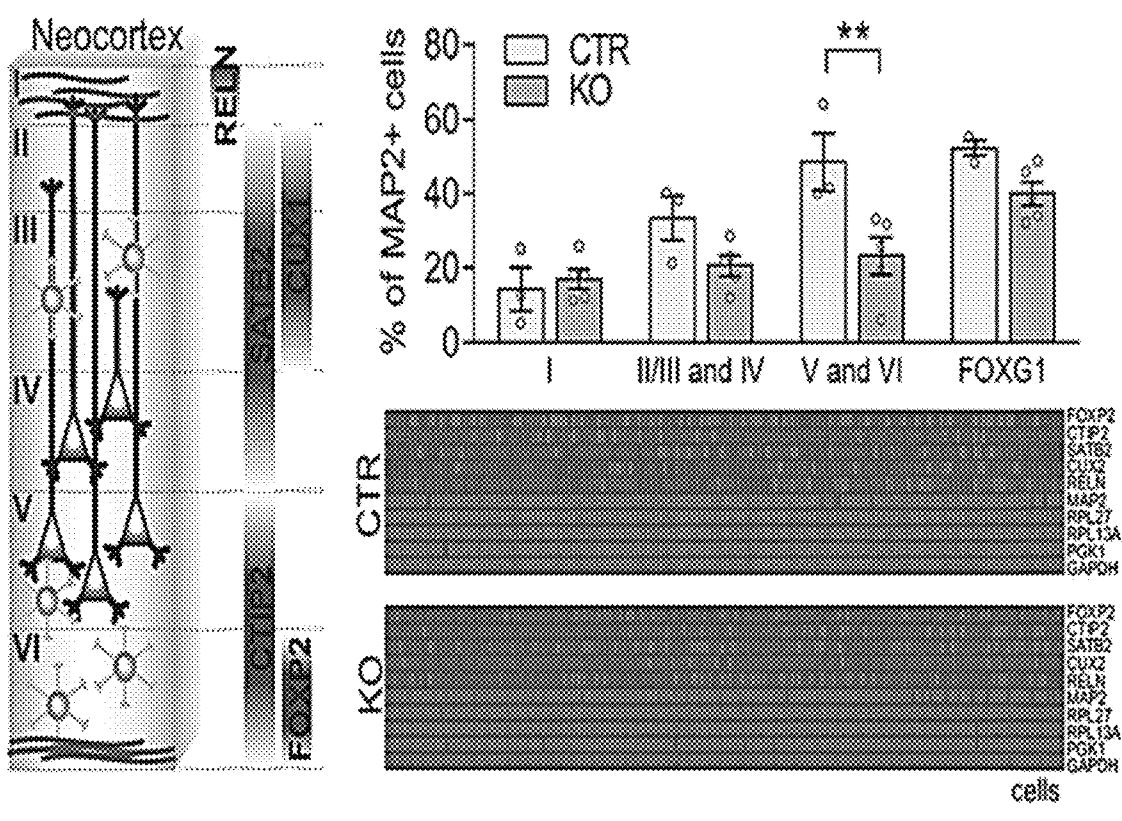
*FIG. 10G*
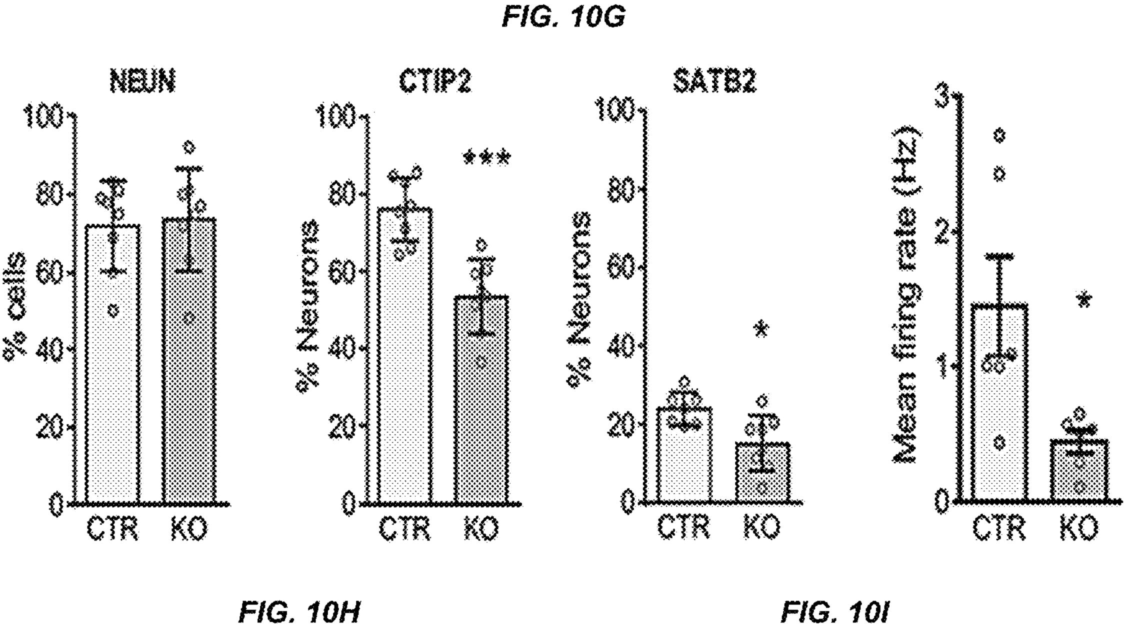
*FIG. 10H*
*FIG. 10I*

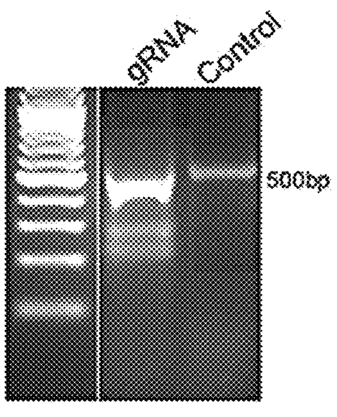
*FIG. 13B*
Exon sequencing
| Sample | Coverage | WT | Del |
|---|---|---|---|
| WT82 | 117 | 117 | 0 |
| K82fs | 161 | 0 | 161 |
WT82 vs K82fs (off-target mutations)
| Chr | Position | Reference | Mutation | Gene |
|---|---|---|---|---|
| 5 | 76373240 | A | G | ZBED3 |
| 14 | 105414790 | A | G | AHNAK2 |
| 11 | 5685385 | C | T | TRIM5 |
| 4 | 22438154 | C | A | GPR125 |
| 17 | 38975328 | G | A | KRT10 |
*FIG. 13C*
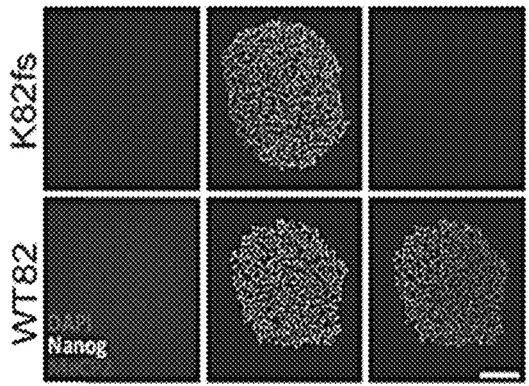
*FIG. 13D*
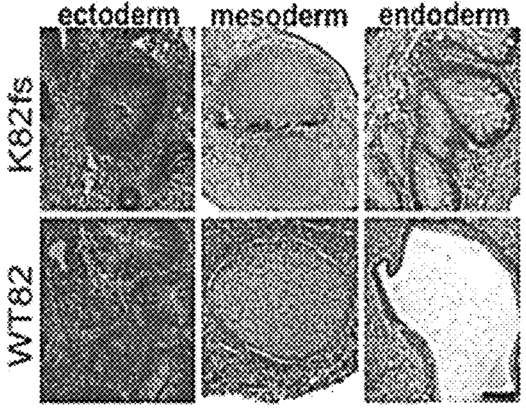
*FIG. 13E*
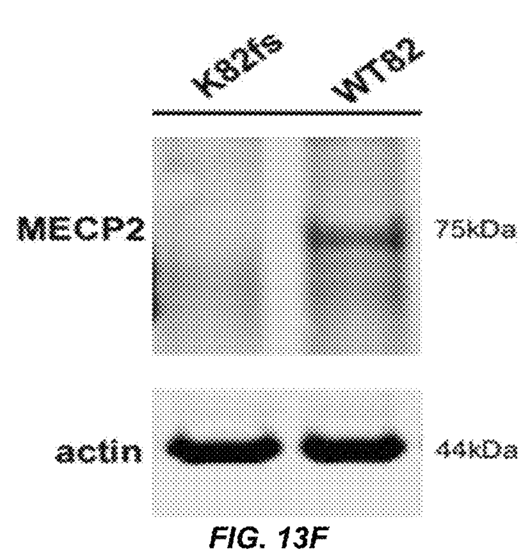
*FIG. 13F*
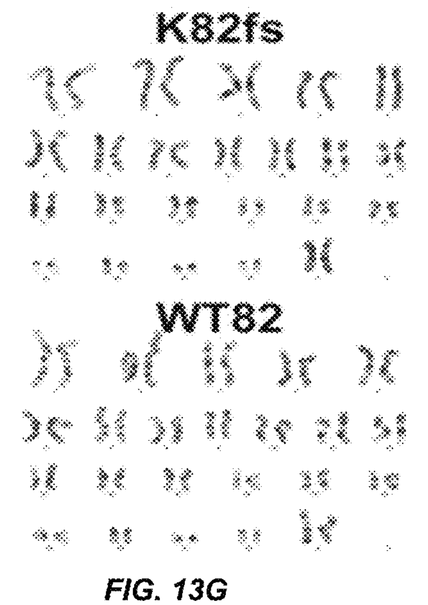
*FIG. 13G*

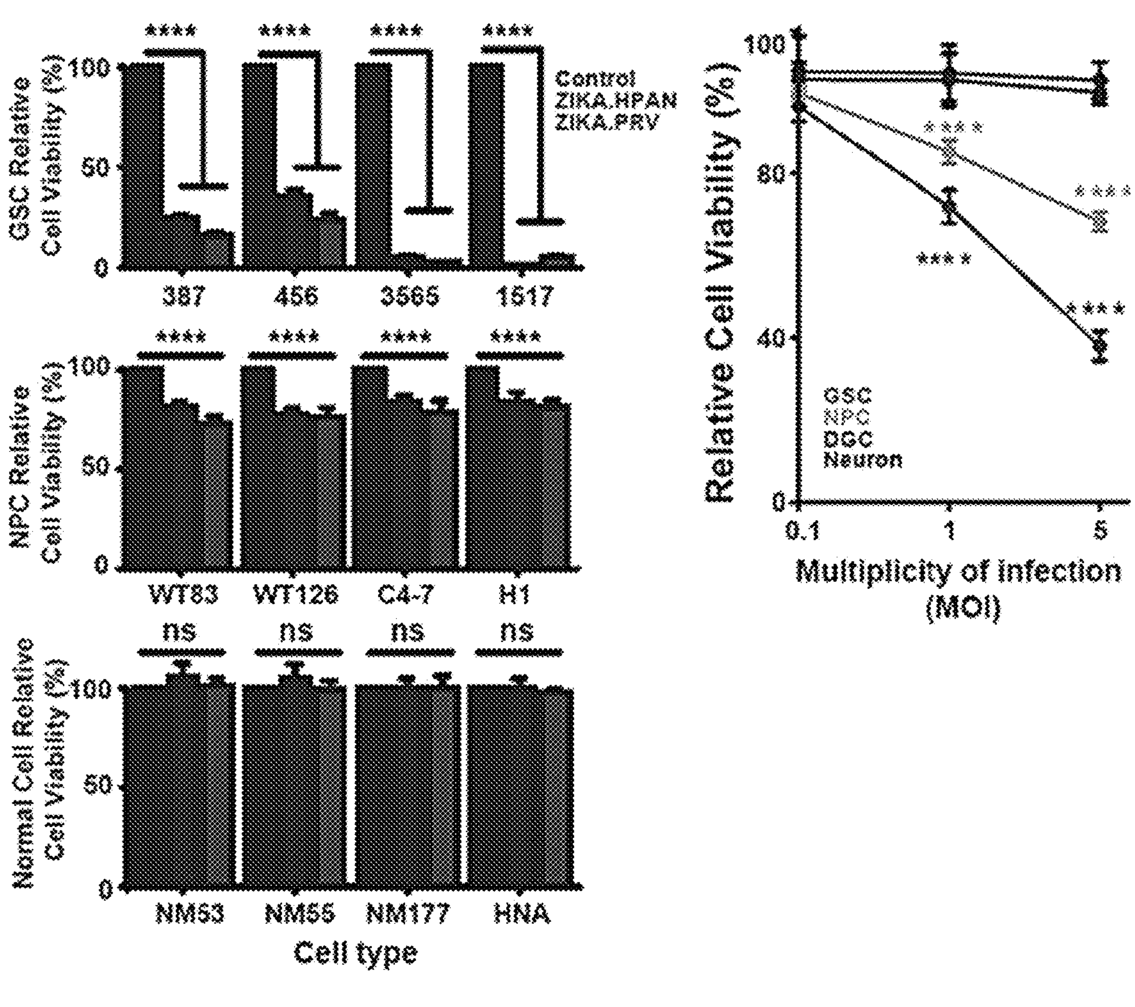
FIG. 16C
FIG. 16D
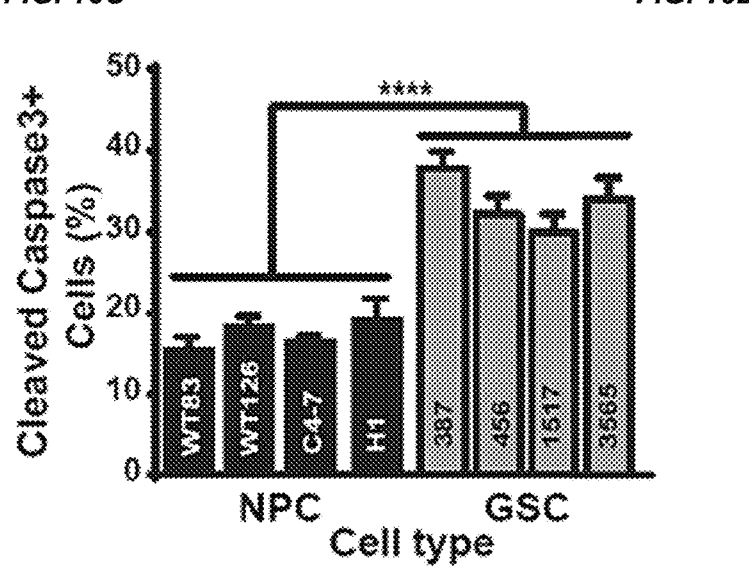
FIG. 16E

FUNCTIONAL CORTICAL ORGANOIDS, METHODS OF MAKING, AND USES THEREOF

CROSS REFERENCE TO RELATED APPLICATIONS

This application is a divisional of U.S. Application Ser. No. 16/634,140, filed Jan. 25, 2020, which application is a U.S. National Stage Application filed under 35 U.S.C. § 371 and claims priority to International Application No. PCT/US2018/043983, filed Jul. 26, 2018, which claims the priority under 35 U.S.C. § 119 from U.S. Provisional Application Ser. No. 62/537,368, filed Jul. 26, 2017, the disclosures of which is are incorporated herein by reference.

STATEMENT REGARDING FEDERALLY SPONSORED RESEARCH

This invention was made with government support under MH109885, MH107367. MH107771, MH109587, MH094753, MH100175, and MH108528 awarded by the National Institutes of Health. The government has certain rights in the invention.

TECHNICAL FIELD

The disclosure provides methods of making functional cortical organoids from somatic cells and stem cells and methods of using the organoids.

INCORPORATION BY REFERENCE OF SEQUENCE LISTING

Accompanying this filing is a Sequence Listing entitled, "2940335-038-US3_SL.xml" created on Apr. 22, 2024 and having 3,846 bytes of data, machine formatted on IBM-PC, MS-Windows operating system. The sequence listing is hereby incorporated by reference in its entirety for all purposes.

BACKGROUND

Diverse and hierarchical cellular networks develop into circuits with patterns of functional spatiotemporal activity to form the human brain. Neural oscillations robustly track cognitive, behavioral, and disease states, and they have long been leveraged to study the brain due to their ubiquity and accessibility. This complex network emerges early in development and is unclear if shaped exclusively by biological programming prenatally. In vitro and in vivo rodent studies have shown that a conserved repertoire of organized network activity, such as traveling waves, Giant Depolarizing Potentials (GDPs), and Early Network Oscillations (ENO), develop according to a consistent timeline prior to and immediately after birth. However, it is unclear whether the same happens in humans, due to an inability to interrogate the electrophysiology of intact embryonic brains. As a result, our knowledge about human brain functional development rests upon extrapolations from nonhuman model systems.

SUMMARY

Structural and transcriptional changes during early brain maturation follow fixed developmental programs defined by genetics. Cognition and behavior require flexible and dynamic coordination of neural ensembles across multiple spatial and temporal scales. Oscillations in the ensemble electric field are a candidate mechanism for how such coordination is instantiated, with oscillatory disruptions associated with numerous and heterogeneous disease states. While network oscillations are readily observed in the intact brain and cortical slices, the development and physiological mechanisms leading to their emergence are not well understood, primarily due to the experimental inaccessibility of the early stages of the living human brain.

The disclosure demonstrates low-frequency oscillations (1-4 Hz) in a novel protocol for cortical organoids derived from human pluripotent stem cells. Using this three-dimensional system, robust and reproducible oscillatory activity, in both population spiking and local field potential (LFP) recordings, was identified after 4 months of development. This coordinated oscillatory electroencephalography (EEG)-like network activity was monitored over 10 months and became more sophisticated as the organoids matured and developed into cortical multi-layered structures. The results show that functional neural circuitry can be achieved in vitro and resembles complex features of the human brain. The present disclosure fills a gap of functional brain development, neuronal network formation and emergence of complex brain waves. The disclosure shows activity of a neuronal circuitry and not only from a single neuron action potential. The main excitatory and inhibitory neurotransmitter systems of the human cortex were present and involved in the establishment of a synchronized network. In addition, low-frequency oscillations (1-4 Hz)—EEG-like brain waves observable in humans—were identified using this novel protocol. The cortical organoids developed herein spontaneously exhibit periodic and highly regular oscillatory network events, followed by a transition to irregular and spatiotemporally complex patterns. This coordinated network activity became more sophisticated as the organoids matured and developed into cortical multi-layered structures. Oscillatory network events mediated delta-high gamma phase-amplitude coupling, while GABAergic blockade increased network-synchronous events and abolished oscillatory dynamics. Additionally, it was found that the Methyl-CpG-binding protein 2 (MECP2) is important for the timely emergence of synchronous oscillatory activity, corroborating that functional maturation might be compromised in MECP2-related genetic disorders. A machine learning approach was used to demonstrate that network activity between 28- to 38-week-old organoids closely mimics features of late-stage preterm infant electroencephalography. The results showed that functional neural circuitry can be achieved in vitro and resembles the activity previously reported in preterm infants, and adults under general anesthesia. These results argue that experience-independent cortical activity may also follow stable genetic programming, as a convergent feature of the early developing human brain. By closing the gap between in vitro neurodevelopmental models and the brain, this study provides heretofore unique opportunities for investigating and manipulating the role of synchronous network activity in the developing human nervous system. The methods and compositions of the disclosure provide heretofore unapproachable opportunities for investigating how oscillatory biomarkers might be disrupted in neurological and psychiatric disorders.

The methods of the disclosure provide a versatile organoid technology platform without the need for specialized equipment, such as a bioreactor; to overcome experimental variability issues, and to develop a mature functional network system that allows the direct interrogation of human cortical activity. In addition to ease of use, the method successfully generated cortical organoids from different cell lines with high reproducibility.

Notably, the cortical organoids were also robust and reproducible at the functional level. The compositions of the disclosure provide a new tool for identifying distinct pathological states and for screening effective drugs. For example, a brain cancer model was developed by integrating human cerebral organoids with glioblastoma stem cell (GSC) models which showed that inhibition of auβs by ZIKV led to the selective depletion of GSCs from mature brain organoids. Accordingly, the cerebral organoids disclosed herein can be used in any number of integrated models looking at pre-clinical testing or drug discovery for brain tumors, and other neurological diseases, disorders and conditions.

In a particular embodiment, the disclosure provides for an in vitro method of generating functional cortical organoids from neural progenitor cells (NPCs) comprising, consisting essentially of or consisting of: culturing NPCs in serum-free supplemented neurobasal media comprising brain-derived neurotrophic factor (BDNF), glial cell-derived neurotrophic factor (GDNF), neutropin-3 (NT-3), a fibroblast growth factor, L-ascorbic acid, and dibutyryl-cAMP to generate functional cortical organoids, wherein the functional cortical organoids are able to produce nested oscillatory waves upon differentiation. In an embodiment, or in furtherance of any embodiment presented herein, the serum-free supplemented neurobasal media is supplemented with GlutaMAX™, Gem21 NeruoPlex™ and non-essential amino acids. In an embodiment, or in furtherance of any embodiment presented herein, the serum-free supplemented neurobasal media comprises antibiotics. In an embodiment, or in furtherance of any embodiment presented herein, the fibroblast growth factor is FGF2. In an embodiment, or in furtherance of any embodiment presented herein, the functional cortical organoids are comprised predominantly of proliferative neural progenitor cells (NPCs) that have self-organized into a polarized neuroepithelium-like structure. In an embodiment, or in furtherance of any embodiment presented herein, a method of the disclosure further comprises: differentiating the functional cortical organoids in serum-free supplemented neurobasal media for at least 60 days. In an embodiment, or in furtherance of any embodiment presented herein, the functional cortical organoids comprise a proliferative region that is surrounded by intermediate progenitor cells expressing TBR2$^+$ and deep cortical layer markers TBR1$^+$ and CTIP2$^+$ and wherein cortical plate folding is observed in the cortical organoids. In an embodiment, or in furtherance of any embodiment presented herein, a method of the disclosure further comprises: differentiating the functional cortical organoids in serum free supplemented neurobasal media for at least 300 days and up to 2 years. In an embodiment, or in furtherance of any embodiment presented herein, the functional cortical organoids comprise pyramidally-shaped neurons, dendritic spines and structurally defined synapses. In an embodiment, or in furtherance of any embodiment presented herein, the functional cortical organoids are cultured with cancer cells to form cortical organoids comprising cancerous tumors. In an embodiment, or in furtherance of any embodiment presented herein, the cancer cells are cancer stem cells. In an embodiment, or in furtherance of any embodiment presented herein, the cancer cells are cells from a cancer selected from the group consisting of adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma. supratentorial primitive neuroectodermal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma. Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, smal intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In an embodiment, or in furtherance of any embodiment presented herein, the cancer cells are cells from a cancer selected from the group consisting of brain cancer, brain tumor, brain stem glioma, cerebellar astrocytoma, cerebral astrocytoma/malignant glioma, ependymoma, medulloblastoma, supratentorial primitive neuroectodermal tumors, and visual pathway and hypothalamic glioma. In an embodiment, or in furtherance of any embodiment presented herein, the cancer cells are glioblastoma cell, glioblastoma multiforme cells, neuroblastoma cells, astrocytoma cells, glioma cells, medullomyoblastoma cells, neuroglioma cells, endothelioma cells, and gliosarcoma cells. In an embodiment, or in furtherance of any embodiment presented herein, the cancer cells are glioblastoma stem cells, glioblastoma multiforme stem cells, neuroblastoma stem cells, astrocytoma stem cells, glioma stem cells, medullomyoblastoma stem cells, neuroglioma stem cells, endothelioma stem cells, and gliosarcoma stem cells. In an embodiment, or in furtherance of any embodiment presented herein, the cancer cells are selected from the group consisting of A172 cells. BC3H1 cells, Bend.3 cells, BT142 cells, CCF-STTG1 cells, CHLA-01-MED cells, CHLA-02-ATRT cells, CHL-157 cells, CHP-212 cells, D283 cells, D341 cells, DAOY cells, DBTRG cells, DBTRG-05MG cells, EP-1 cells, GMB146, GMB157, HBMB03 cells, H4 cells, Hs 683 cells, IMR-32 cells, LN-18 cells, LEE cells, LN-229 cells, LN-827 cells, M059J cells, M059K cells, N1E-115 cells, NB41A3 cells, Neuro-2a cells, PFSK-1 cells, SF-295 cells, SF-539 cells, SF-767 cells, SNB-19 cells, SW 1088 cells, SW 1783 cells, T98G cells, U-87 MG cells, U-118MG cells, U-138 MG cells, U251 cells, 9L cells, C6 cells, C6/A cells, F98EGFR cells, G98npEGFRvIII cells, F98 cells, RG2 cells, glioblastoma stem cell (GSC) line 387, GSC line 3832, and GSC line 3565. In an embodiment, or in furtherance of any embodiment presented herein, the NPCs are differentiated from stem cells comprising the steps of: (i) culturing stem cells in feeder-free media comprising inhibitors for bone morphogenetic protein (BMP) and transforming growth factor-β (TGF-β) pathways: (ii) subculturing the stem cells of (i) in suspension under rotation in the presence of a ROCK inhibitor to form free-floating spheres; (iii) culturing the free-floating spheres in serum-free supplemented neurobasal media comprising inhibitors for BMP and TGF-β pathways to obtain neuronal progenitor cells (NPCs); and (iv) expanding/proliferating the NPCs by first culturing the NPCs in serum-free supplemented neurobasal media comprising a fibroblast growth factor (FGF) and then culturing the NPCS in serum-free supplemented neurobasal media comprising the FGF and an epidermal growth factor (EGF). In an embodiment, or in furtherance of any embodiment presented herein, the stem cells are induced pluripotent stem cells. In an embodiment, or in furtherance of any embodiment presented herein, the induced pluripotent stems cells are obtained from fibroblasts. In an embodiment, or in furtherance of any embodiment presented herein, the fibroblasts are obtained from a subject having a neurological disease, disorder or syndrome. In an embodiment, or in furtherance of any embodiment presented herein, the fibroblasts are obtained from a patient that is suspected of having cancer or has a cancer. In an embodiment, or in furtherance of any embodiment presented herein, the patient that is suspected of having brain cancer or has a brain cancer. In an embodiment, or in furtherance of any embodiment presented herein, wherein for (i) the inhibitors for BMP and transforming growth TGF-β pathways comprise SB431542 and Dorsomorphin. In an embodiment, or in furtherance of any embodiment presented herein, wherein for (iii) the inhibitors for BMP and transforming growth TGF-β pathways comprise SB431542 and Dorsomorphin. In an embodiment, or in furtherance of any embodiment presented herein, wherein for (iii) the serum-free neurobasal media is supplemented with GlutaMAX™, Gem21 NeuroPlex™, N2 NeuroPlex™, and nonessential amino acids. In an embodiment, or in furtherance of any embodiment presented herein, wherein for (iv) the serum-free neurobasal media is supplemented with GlutaMAX™, Gem21 NeuroPlex™, N2 NeuroPlex™, and nonessential amino acids. In an embodiment, or in furtherance of any embodiment presented herein, wherein for (iv) the fibroblast growth factor is FGF2. In an embodiment, or in furtherance of any embodiment presented herein, wherein for (iv) the NPCs are first cultured in serum-free supplemented neurobasal media comprising an FGF for seven days and then cultured for seven days in serum-free supplemented neurobasal media comprising an FGF and EGF. In an embodiment, or in furtherance of any embodiment presented herein, a functional cortical organoid is made by the method disclosed herein. In an embodiment, or in furtherance of any embodiment presented herein, the functional cortical organoid comprises cancerous tumors. In an embodiment, or in furtherance of any embodiment presented herein, the disclosure provides a method for screening for one or more agents or one or more compounds that affect the oscillatory activity of a cortical organoid, comprising: contacting a functional cortical organoid of the disclosure with one or more agents or one or more compounds, or a vehicle control: and measuring any differences in the oscillatory activity of the cortical organoids contacted with the one or more agents or the one or more compounds vs. the vehicle control, wherein the vehicle control does not affect the oscillatory activity of the functional cortical organoid, and wherein a measured difference in the oscillatory activity of the functional cortical organoid contacted with the one or more agents or the one or more compounds vs. the vehicle control indicates that the one or more agents or the one or more compounds affect the oscillatory activity of the functional cortical organoid. In an embodiment, or in furtherance of any embodiment presented herein, the disclosure provides a method for screening for one or more agents or one or more compounds that have a neuroprotective effect, comprising: contacting a cortical organoid of the disclosure with one or more agents or one or more compounds, or a vehicle control; exposing the cortical organoid to a neurodegenerative insult; measuring any differences in the levels of glutathione, glial fibrillary acidic protein, and/or glutamate of the cortical organoid contacted with the one or more agents or the one or more compounds vs, the vehicle control, measuring any differences in the structure and/or function of the functional cortical organoid contacted with the one or more agents or the one or more compounds vs, the vehicle control, wherein the vehicle control does not affect the structure and/or function of the functional cortical organoid, and wherein a preservation or a reduction in the rate of the loss of the structure and/or function of the cortical organoid contacted with the one or more agents or the one or more compounds vs. the vehicle control indicates that the one or more agents or one or more compounds have a neuroprotective effect. In an embodiment, or in furtherance of any embodiment presented herein, the disclosure provides a method for screening for one or more agents or one or more compounds that can be used to treat malignancies or cancerous growths, comprising: contacting a functional cortical organoid of the disclosure comprising cancerous tumors with one or more agents or one or more compounds; and determining whether the one or more agents or the one or more compounds kills the cancerous tumor cells in the cortical organoid, wherein if it is determined that the one or more agents or the one or more compounds kills the cancerous tumor cells in the functional cortical organoid, then the one or more agents or the one or more compounds can be used to treat malignancies or cancerous growths. In an embodiment, or in furtherance of any embodiment presented herein, the functional cortical organoids comprise cancerous tumors of glioblastoma stem cells, glioblastoma multiforme stem cells, neuroblastoma stem cells, astrocytoma stem cells, glioma stem cells, medullomyoblastoma stem cells, neuroglioma stem cells, endothelioma stem cells, and/or gliosarcoma stem cells. In an embodiment, or in furtherance of any embodiment presented herein, the functional cortical organoids are generated from a patient that has a cancer, and the cancerous tumors of the cortical organoids are generated from the patient's cancer cells. In an embodiment, or in furtherance of any embodiment presented herein, the patient has a brain cancer. In an embodiment, or in furtherance of any embodiment presented herein, the disclosure provides for a screening method disclosed herein that utilizes high throughput screening in a multi-well format where each well comprises an individual functional cortical organoid that is exposed to a different agent or to a different compound, or to the vehicle control, and wherein more than a hundred functional cortical organoids are screened per high throughput run. In an embodiment, or in furtherance of any embodiment presented herein, more than a thousand cortical organoids are screened per high throughput run.

DESCRIPTION OF DRAWINGS

FIG. 2A-D demonstrates the reproducibility and single-cell characterization. (A) Schematic showing the single-cell approach performed to access reproducibility of organoid generation using two control iPSC lines. (B) tSNE plot of single-cell mRNA sequencing data from 6-month-old organoids color-coded by replicate. (C) Split Dot Plot depicting the correlation between expression patterns of representative markers and cell populations identified within the dataset. The size of the dots represents the percentage of cells expressing a given gene, while the intensity of the color denotes the average expression level (grey, low expression: red/blue, high expression). (D) Population ratio of each cluster by replicate.

FIG. 3A-D provides the synaptic and calcium profile. The synaptic content ($Syn1^+$ puncta) (A) and spontaneous intracellular calcium variation in a defined area of the neuronal soma (B-D) are increased compared to 2D monolayer neural cultures. Scale bar. 200 μm. (C) Representative spontaneous intracellular calcium variation traces from neurons in the cortical organoid at 6 weeks. (D) Calcium transient frequency (3 independent experiments for each cell culture; n=29 cells). Data presented as mean±s.e.m. * $P<0.05$, unpaired Student's t-test.

FIG. 4A-K provides for the oscillatory network dynamics in long-term cortical organoids. (A) Schematic of the organoid signal processing pipeline. Raw MEA data is analyzed as population spiking and LFP separately. Synchronous network events are highlighted in yellow. (B) Raster plot of network spiking activity after 1.5 and 6 months of maturation. A 3-s interval of activity over 5 channels is shown in the upper right corners. (C) Cortical organoids show elevated and continuously increasing mean firing rate compared to 2D monolayer neurons (n=8 organoid cultures, and n=12 for 2D neurons). Inset, correlation of the firing rate vector over 12 weeks of differentiation (from 8 to 20) between pairs of cultures showing reduced variability among organoid replicates. (D) Raster plot representations of MEA recordings from cortical organoids and 2D monolayer neurons. A 3-s burst over 5 channels is shown in the upper right corners. (E) Temporal evolution of cortical organoid network activity. Detailed definitions and further parameters are presented in FIG. 5B-C. (F) Time series of population spiking and LFP during network events in cortical organoid development. Each trace represents a single event during the same recording session. (G) Temporal evolution of cortical organoid network activity characterized by different parameters. n=8 (4 independent experiments performed in duplicates). (H) Oscillatory dynamics within network events develop nonlinearly, following an inverted-U trajectory. (I) Increase of network variability dynamics throughout development. (J) Oscillatory power increases up to the 25th week in culture and plateaus at 30 weeks. Inset, Oscillatory power is calculated by fitting a straight line (dashed) over the aperiodic portion of the PSD and taken as the height of narrow peaks rising above the linear fit. (K) Summary of the network development evidenced by the electrophysiological data. The data shown in (C), (E), and (H)-(J) are presented as mean±s.e.m. * $P<0.05$,  $P<0.01$, * $P<0.001$, unpaired Student's t-test (C), linear (H) and quadratic (I) regression.

FIG. 5A-E presents long-term microelectrode array (MEA) network activity. (A) Representative bright-field images of cortical organoids over time on the MEA plate. (B) Schematic representation of the electrical activity features analyzed from the MEA recordings. Each bar represents a spike; and a spike cluster (in blue) represents a burst. Bursts occurring at the same time in different channels characterize a network burst. The synchrony index is based on the cross-correlogram and represents a measure of similarity between two spike trains. (C) Temporal evolution of network activity characterized by different parameters. (D) Raster plots illustrating the development of network activity.

(E) Consistent and reproducible development of electrical activity in cortical organoids over time. The data are shown as mean±s.e.m (n=8, independent experiments performed in duplicates using two clones of a control iPSC line).

Figures 6A, 6B:
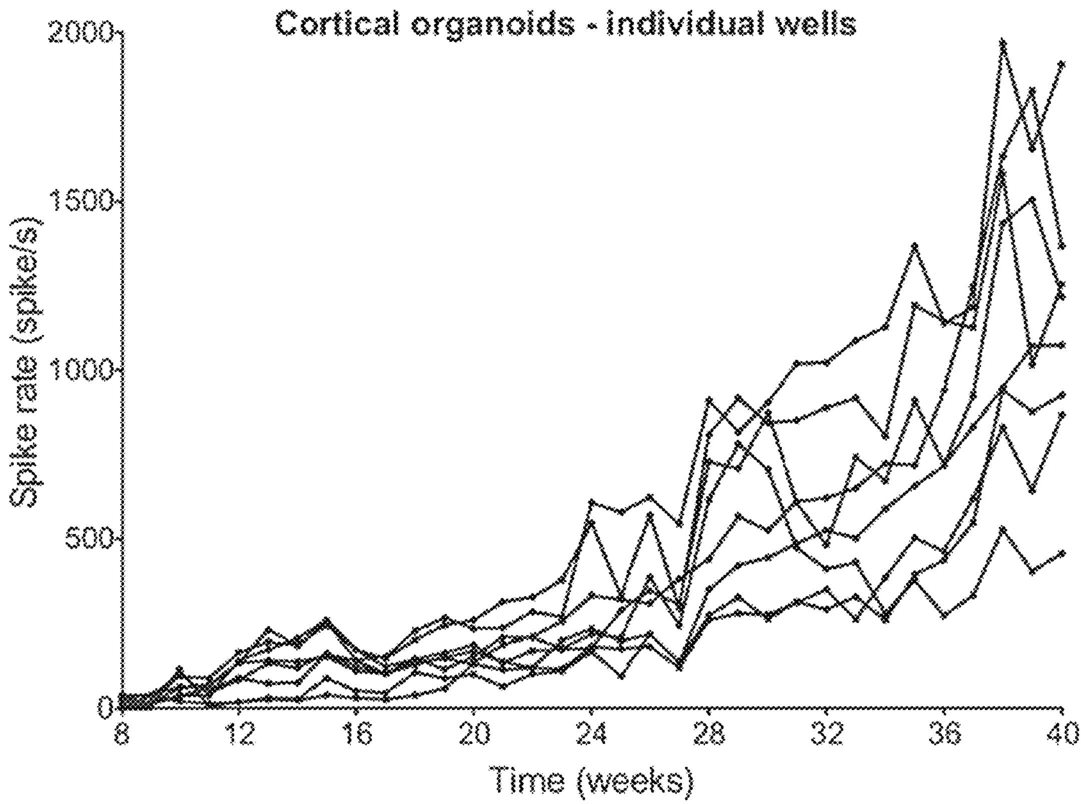
Figures 6C, 7A:
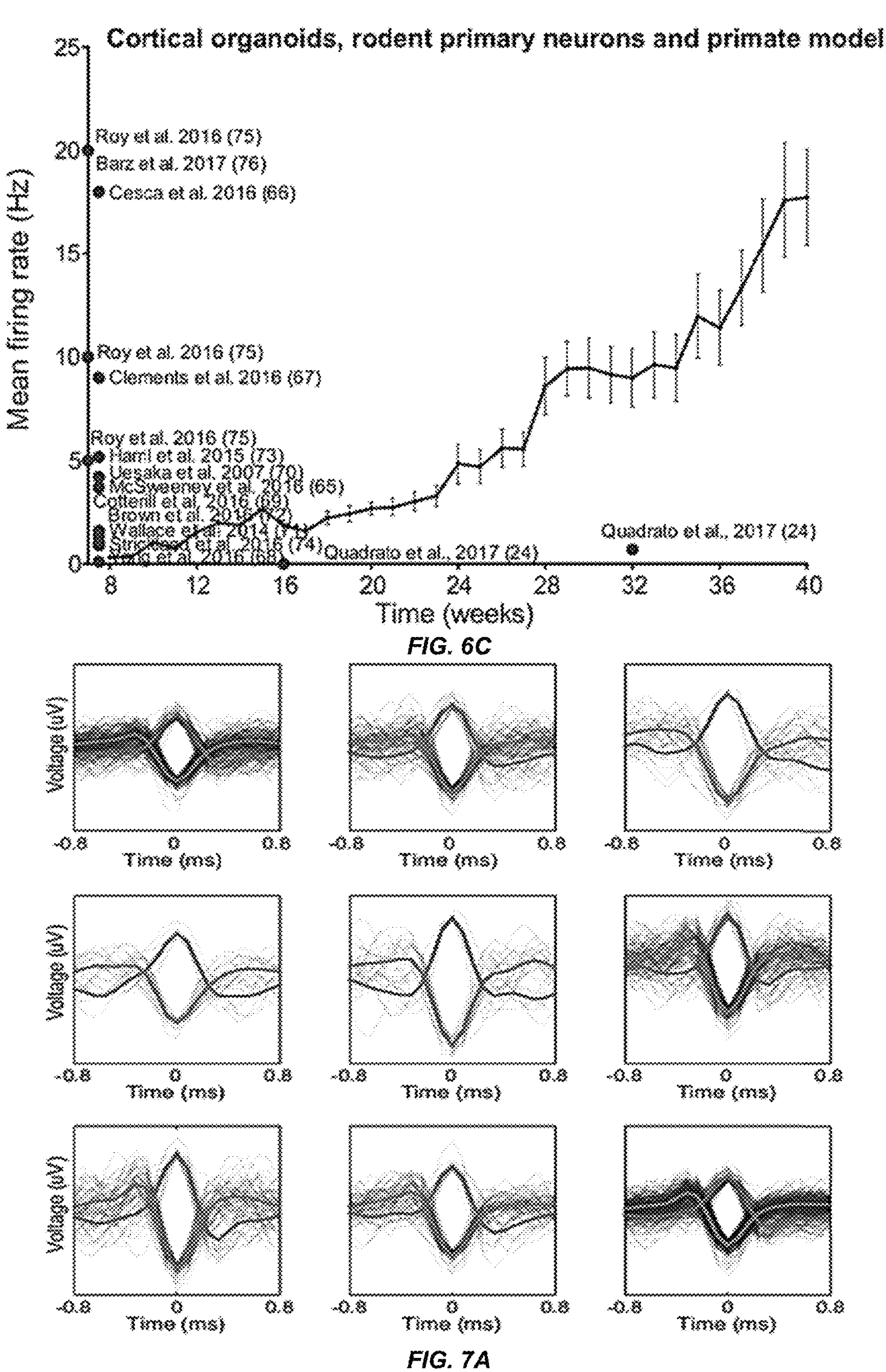

FIG. 6A-C provides MEA electrical activity comparison of cortical organoids with available published data from iPSC-derived neurons, organoids, rodent primary cultures and primate models. (A) Long-term network activity of the cortical organoids is shown for individual wells. Comparison of network activity between cortical organoids and iPSC-derived cortical neurons (B), rodent primary neuronal cultures and primate models (C). The data shown in (B) and (C) for cortical organoids are presented as mean +s.e.m. (n=8, independent experiments performed in duplicates).

FIG. 7A-J provides for the extended characterization of network electrophysiology. (A) Spikes detected on 9 channels. Black traces represent single spikes, blue and red traces represent the average of positive and negative spikes, respectively. Spike trains are not sorted for their polarity in the subsequent analyses, as total population spiking is the main feature of interest. (B) Representative oscillatory network events. Each overlapping trace represents a single occurrence of an event recorded on the same channel. LFP polarity of events differs between channels due to spatial configuration of cells around the electrode. (C) Event onset peak (Peak 1) increases in amplitude until 30 weeks, while (D), subpeak amplitude continues to increase (for the 2nd-4th peak) throughout development. (E) Subsequent peaks occur with a consistent latency of ~400 ms after the previous peak, particularly for Peak 3 and 4. (F) Spatial similarity of network events, which was measured via LFP correlation, increases for up to 25 weeks and then decreases, suggesting a divergence of network activity over space. (G) Temporal similarity of network events during the 3-s window is high at early time points, but decreases with development, acquiring more variable dynamics within an event. (H) Oscillatory dynamics within network events develop nonlinearly over 32 weeks in vitro, and the number of subpeaks within each event follows an inverted-U trajectory. Organoid networks acquire more complex dynamics throughout development. (I) The inter-event interval increases over time, indicating increasing variability in network event initiation and termination. (J) Network events occur at a high frequency over 40 weeks of development. The data shown in (C), (F) and (G) are presented as mean± s.e.m., linear (C), (G) or quadratic (F) model regression.

Figures 8A, 8B, 8C:
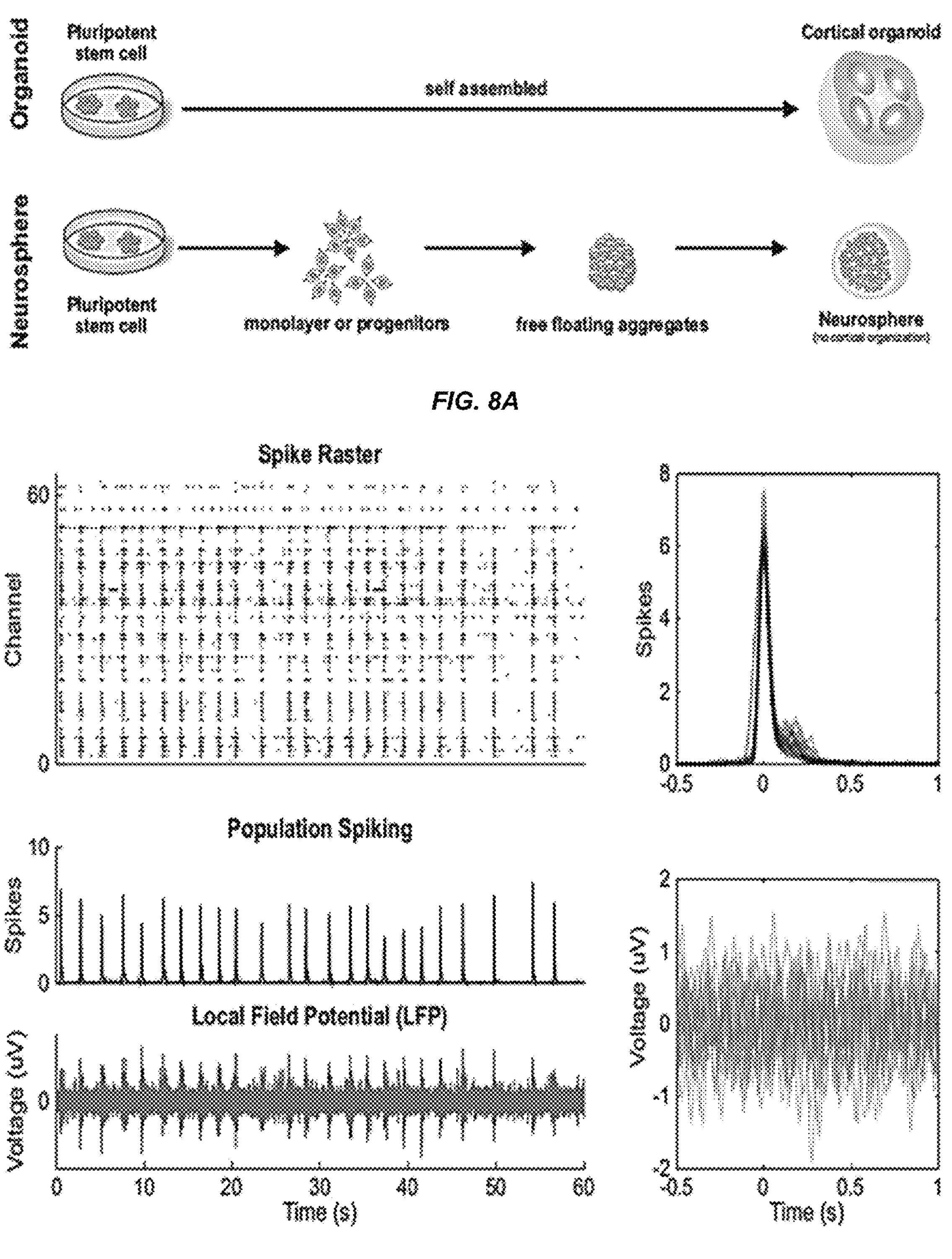
Figures 9A, 9B, 9C, 9D:
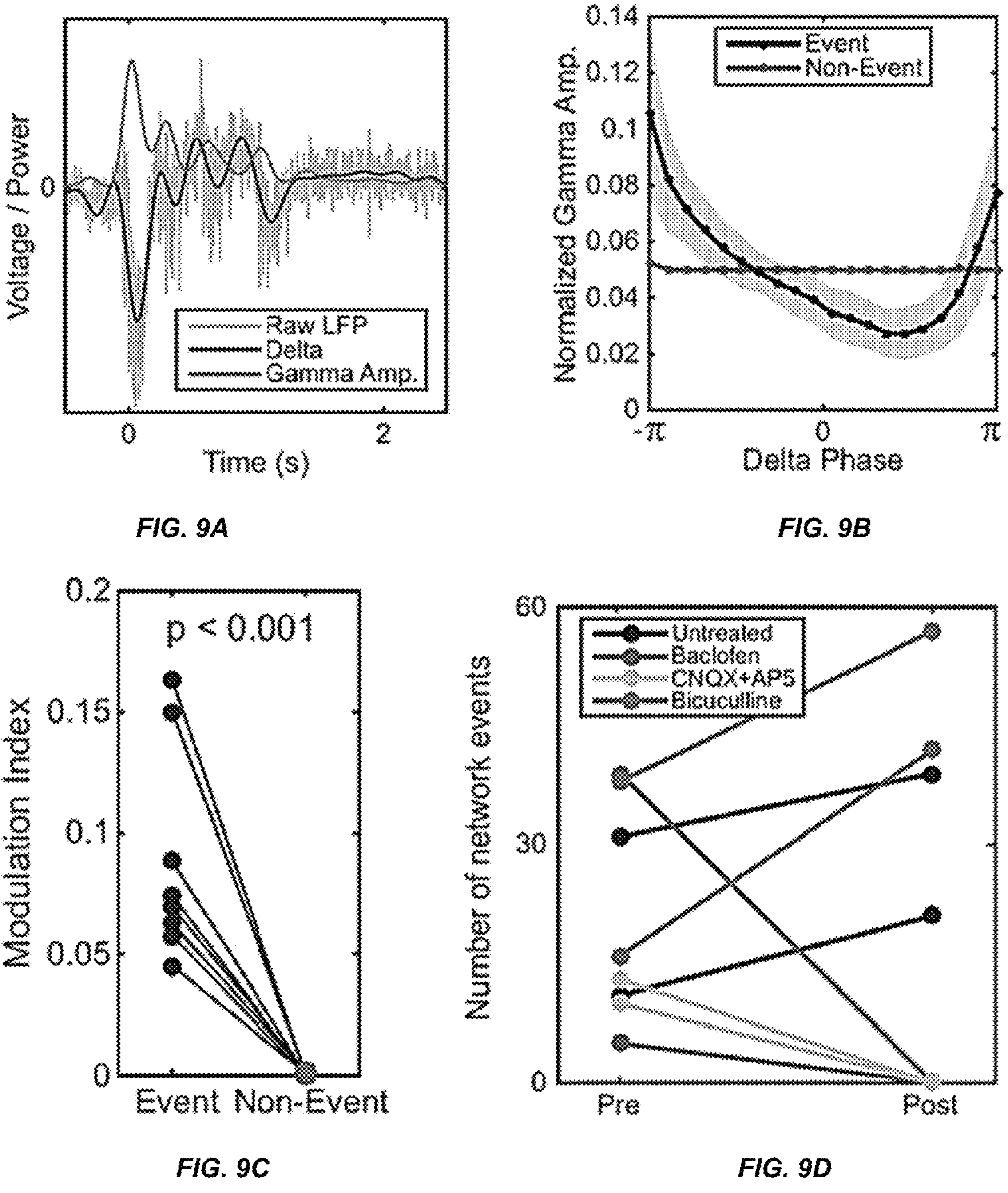
Figure 9E:
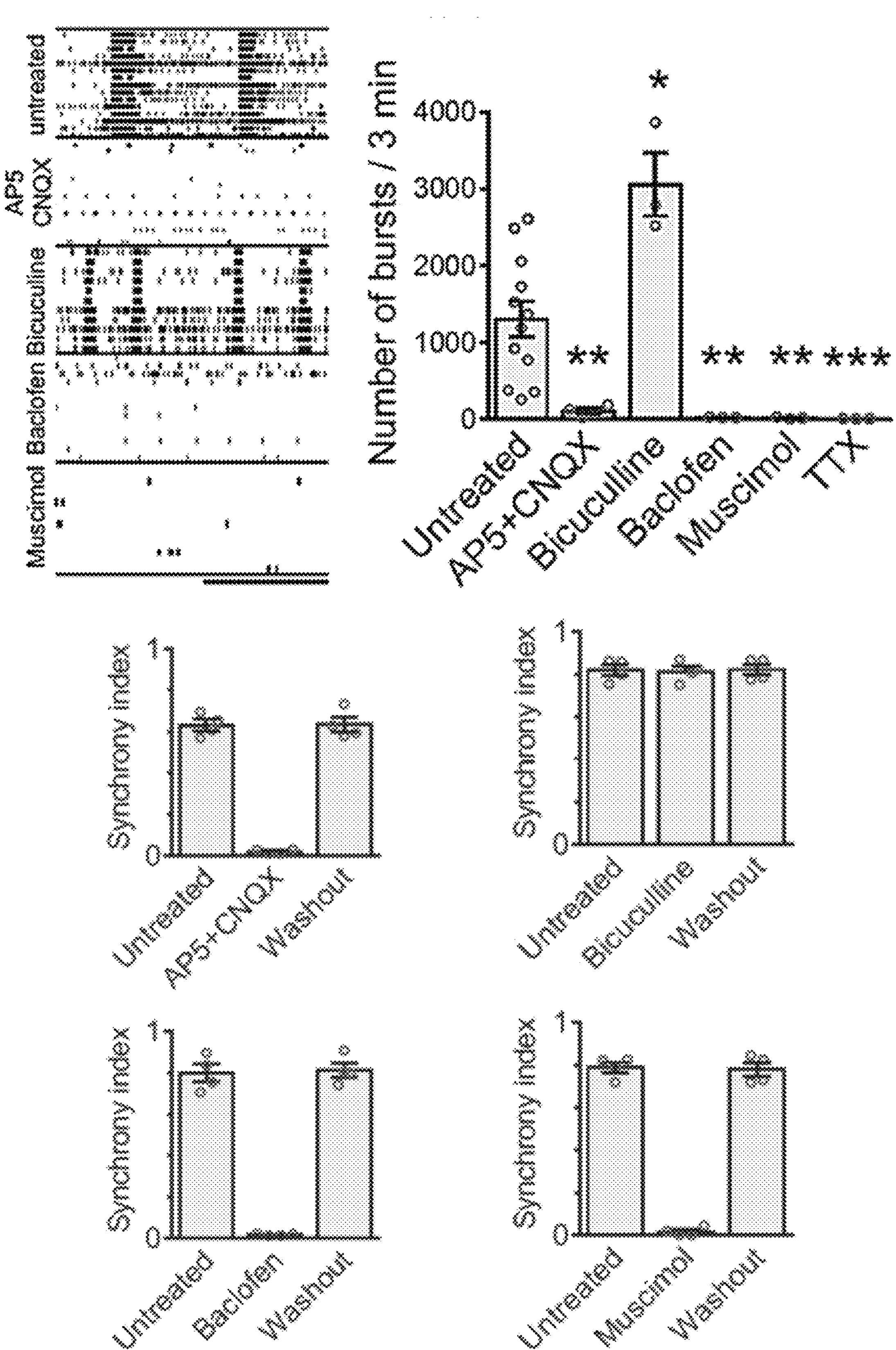
Figures 9F, 10A, 10B:
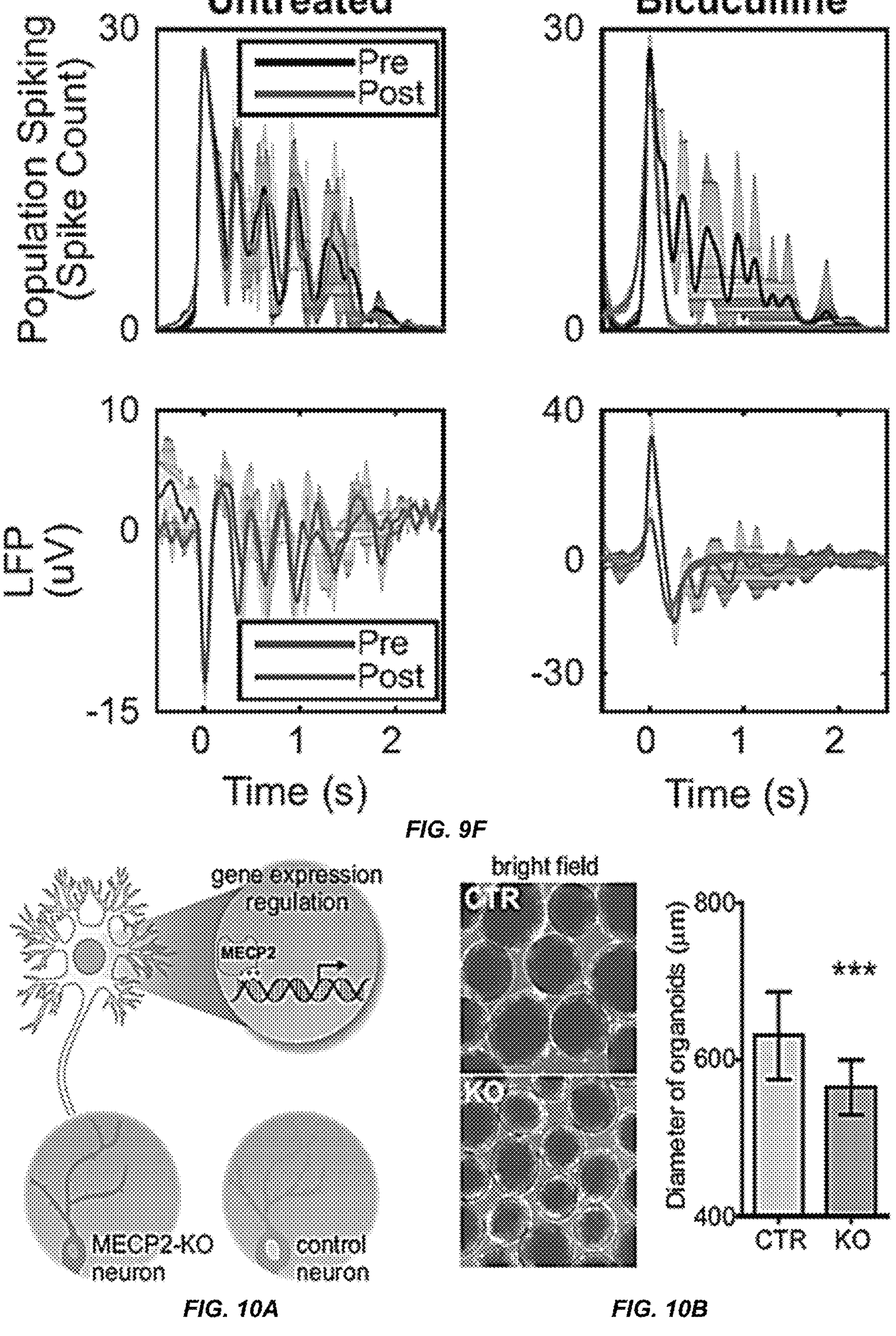
Figures 10C, 10D, 10E, 10F:
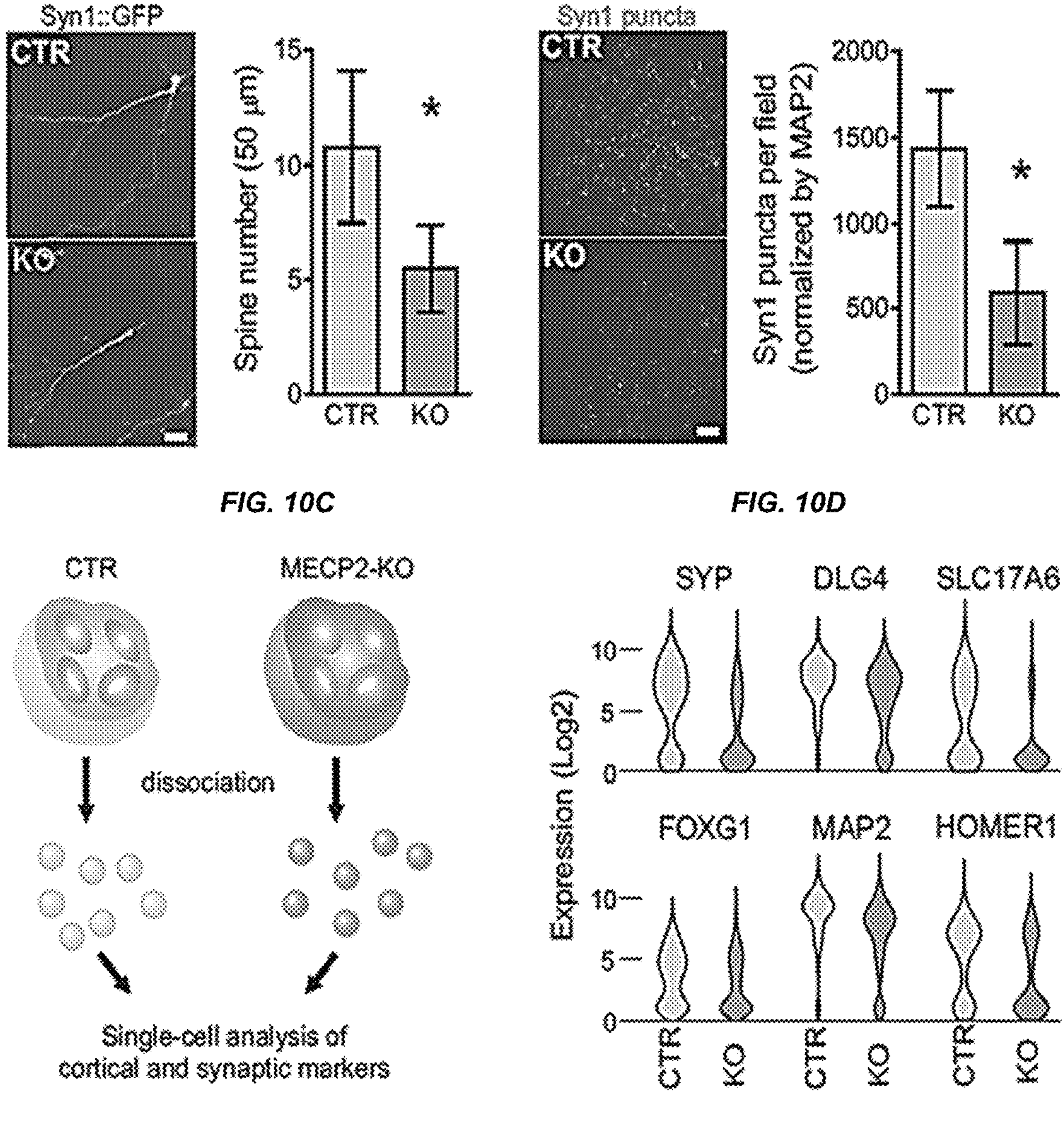
Figure 10J:
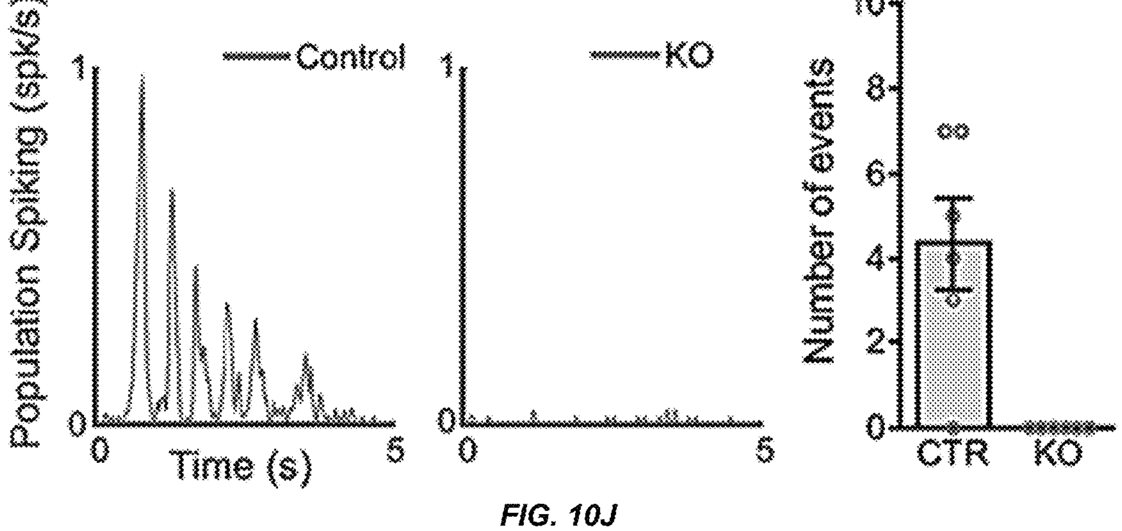

FIG. 8A-C presents a MEA recording from 3-month-old neurospheres. (A) Comparison of the protocol for neurosphere and cortical organoid generation. (B) Network-wide GDPs occur at a similar rate to those found in organoids recordings, and visible perturbations are observed in the LFP trace. However, the network recruitment in neurospheres is lower than in organoids (less than 8 spikes/s), and events have significantly shorter duration. No coherent low-frequency depolarizations are observed in filtered LFP events (C).

FIG. 9A-F demonstrates that the cortical organoid serves as a model of functional oscillations and their synaptic mechanisms. (A)-(C), Phase-amplitude coupling is observed in organoid LFP during network events, mimicking oscillation-mediated neural communication in vivo. (A) Example of raw LFP during a network event decomposed into its low-frequency component (1-4 Hz delta) and the amplitude envelope of the high-frequency, broadband gamma component (200-400 Hz). (B) Normalized gamma amplitude binned by delta phase during network events (black) shows greater modulation depth by low frequency delta than during non-event periods (red). (C) Phase-amplitude coupling during network events is significantly greater than non-event periods in all batches. (D) and (F), Pharmacological perturbation of oscillatory activity during network events in 6-month-old organoids. Application of bicuculline increases the number of network events, while CNQX+AP5 and baclofen completely abolishes synchronized network events. Bicuculline blocks oscillatory network activity but not the network event itself. (E) Effect of selective drug treatments on neuronal electrical activity in 6-month-old organoids. Representative raster plots and burst measurements of untreated and treated organoids. Scale bar, 20 s. Exposure to AP5+CNQX, baclofen and muscimol reversibly extinguish the network bursts (synchrony), while no changes were promoted by bicuculline. Data are shown as mean±s.e.m.; unpaired Student's t-test.

FIG. 10A-J demonstrates the MECP2 contribution to the emergence of network oscillations. (A) MECP2-knockout neurons (MECP2-KO) show reduced spine density and soma size compared to controls. (B) Organoid diameter quantification (CTR, n=210 organoids: KO, n=333 organoids). Spine density (C) and synaptic puncta (D) are reduced in MECP2-KO neurons. Scale bar, 50 μm. (E)-(H). Targeted single-cell analysis of neural markers and cortical layer-related genes over defined control Ct value. In 3-month-old cortical organoids, a significant decrease in the number of $CTIP2^{+}$ and SATB2+ neurons were observed. (I) MECP2-KO cortical organoids show decreased mean firing rate after 5 months of maturation (n=6 organoid cultures). (J) Lack of oscillatory network events in 5-month-old MECP2-KO organoids. Each trace represents a single event during the same recording session. For (B)-(D) and (G)-(I), data are shown as mean±s.e.m .: * $P<0.05$,  $P<0.01$, * $P<0.001$, unpaired Student's t-test.

Figure 11A:
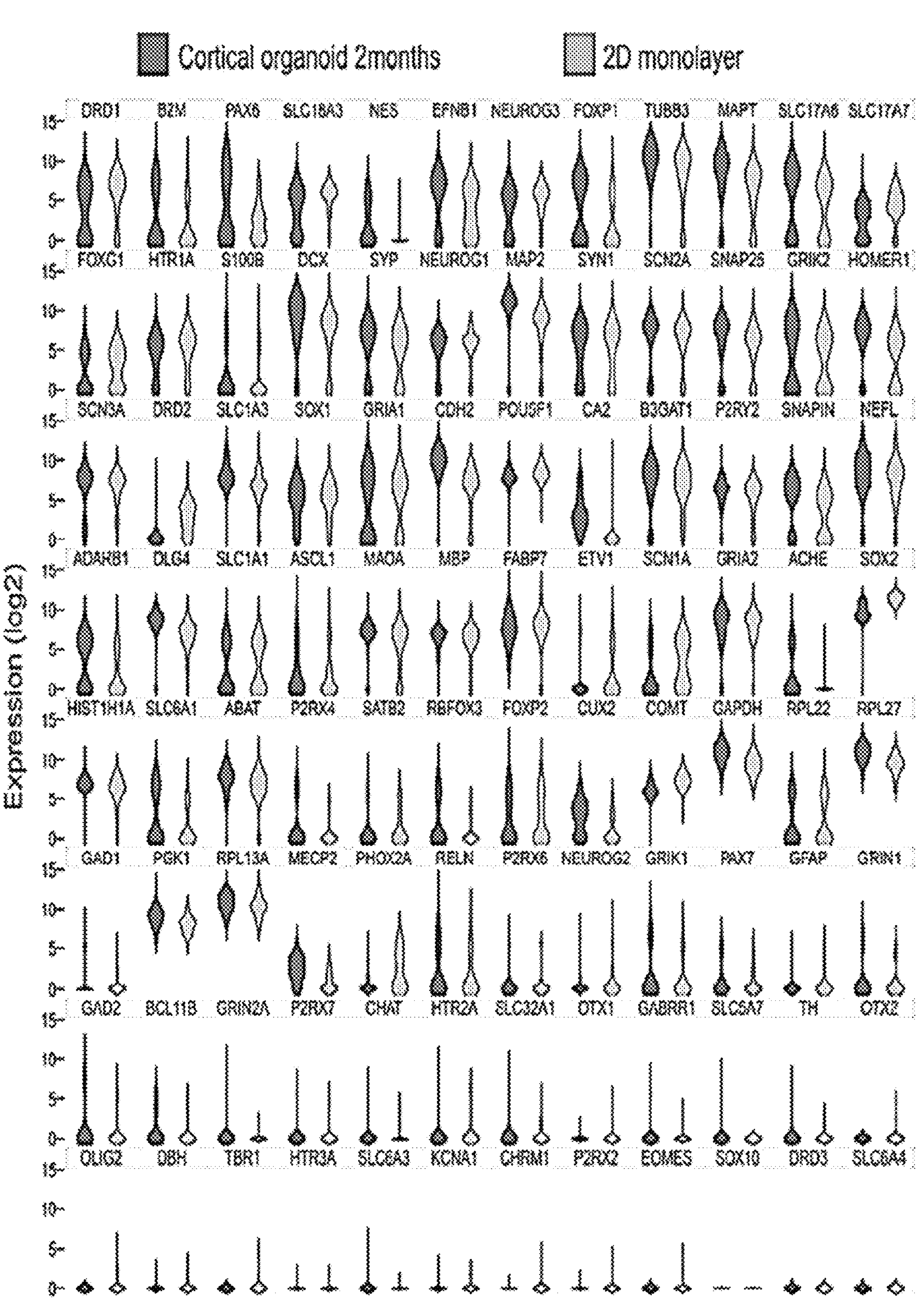
Figure 11B:
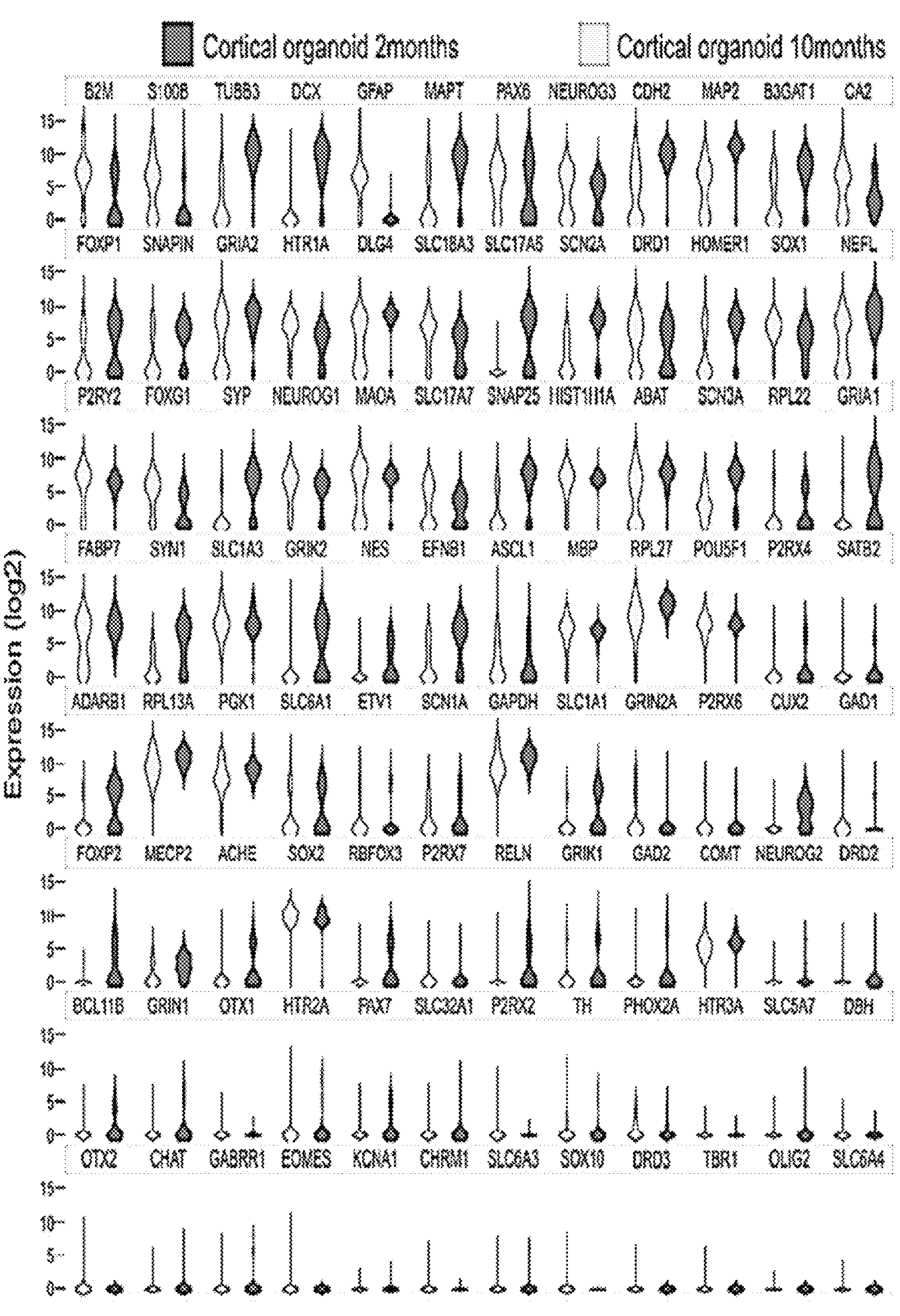

FIG. 11A-B shows reproducibility and single-cell characterization of iPSC-derived cortical organoids. (A) and (B) Violin plots of all 96 genes showing the comparison between 2-month-old cortical organoids and 2D monolayer neurons (A), and between 2-month-old cortical organoids and 10-month-old cortical organoids (B) from the single-cell analyses (Log2ex values). The iPSC stage was considered as day 0. n=2 for each cortical organoid culture (2- and 10-month-old): n=3 for 2D neurons.

Figures 12A, 12B:
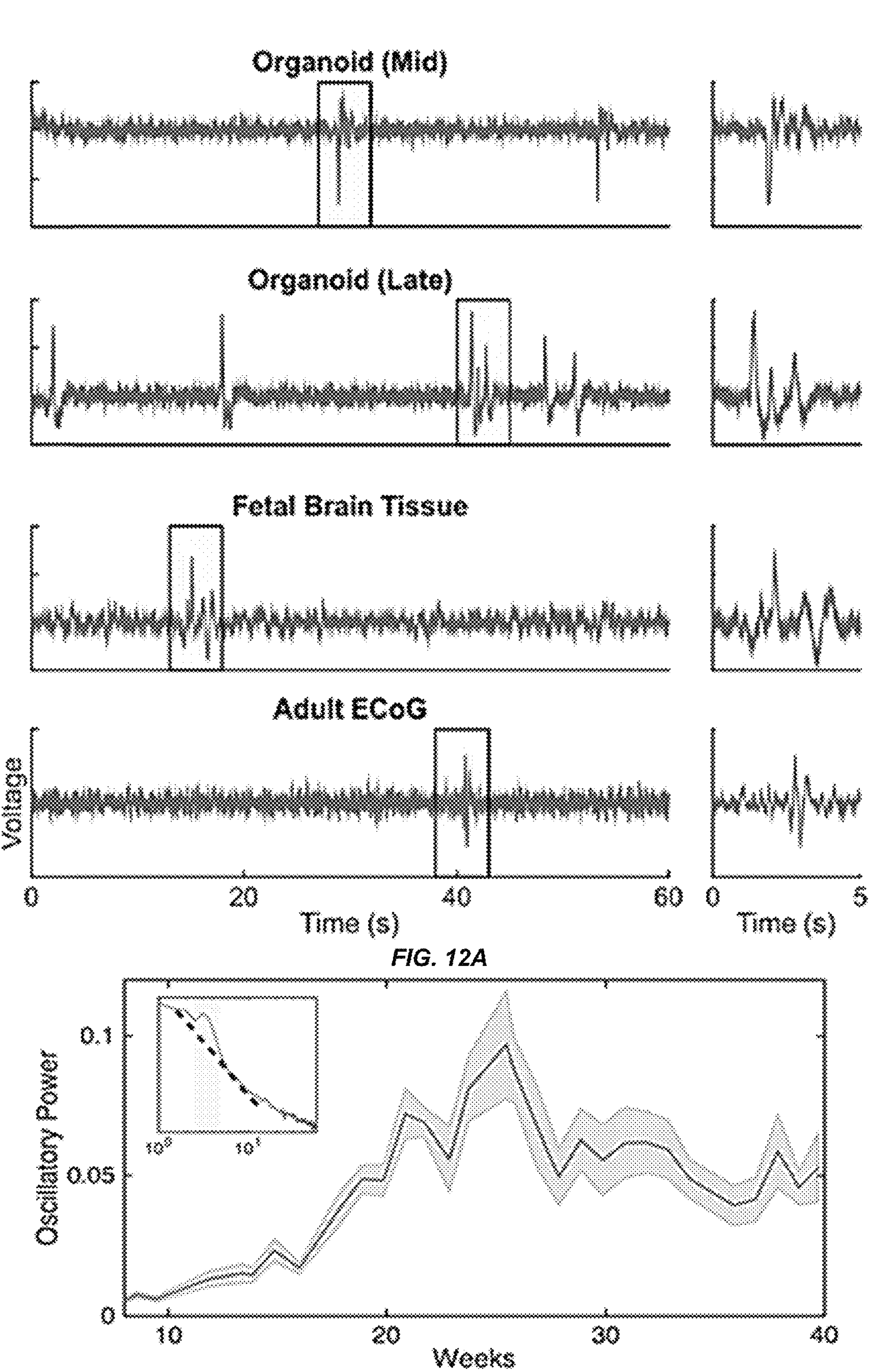
Figures 12C, 13A:
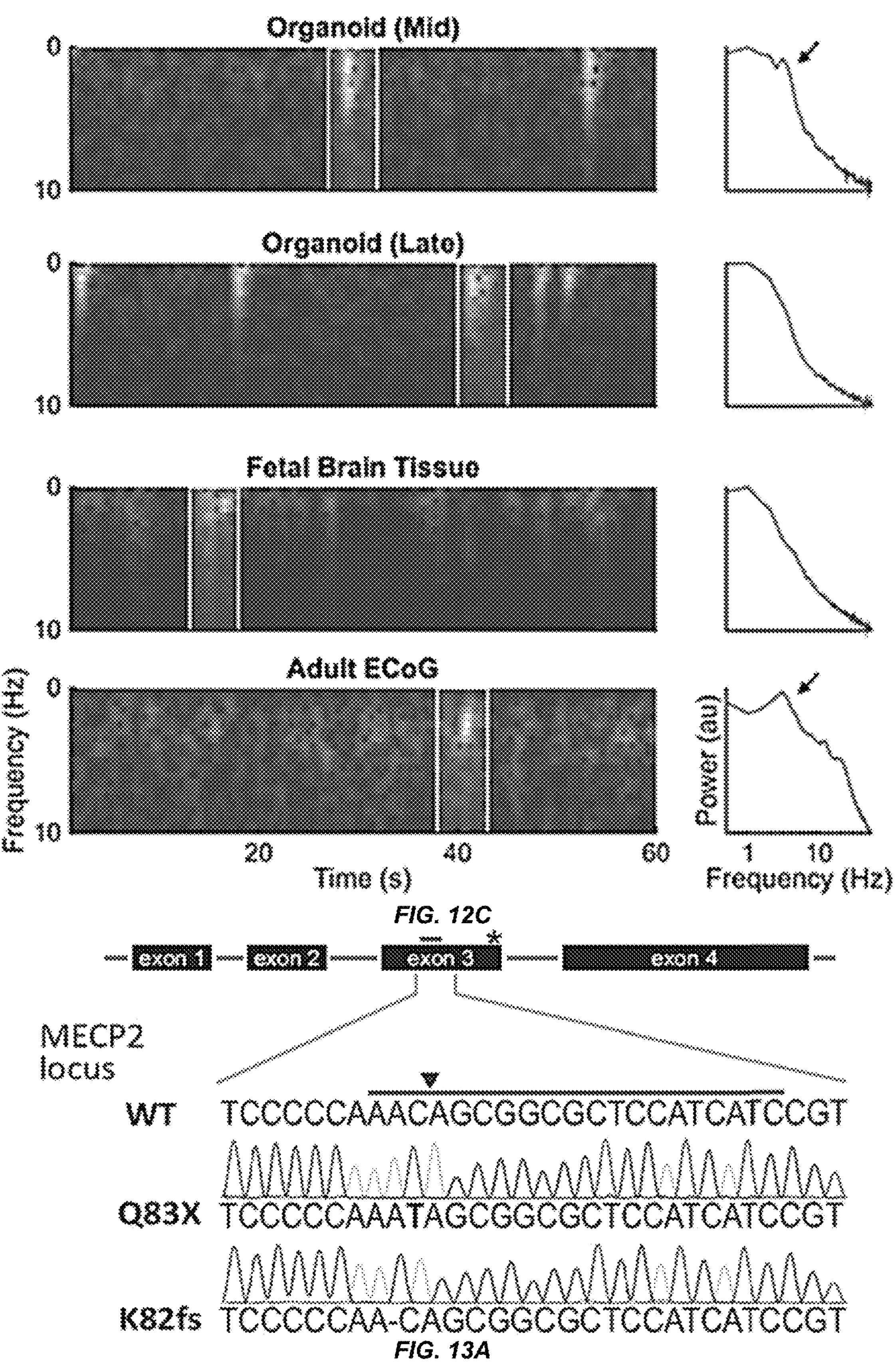
Figure 13H:
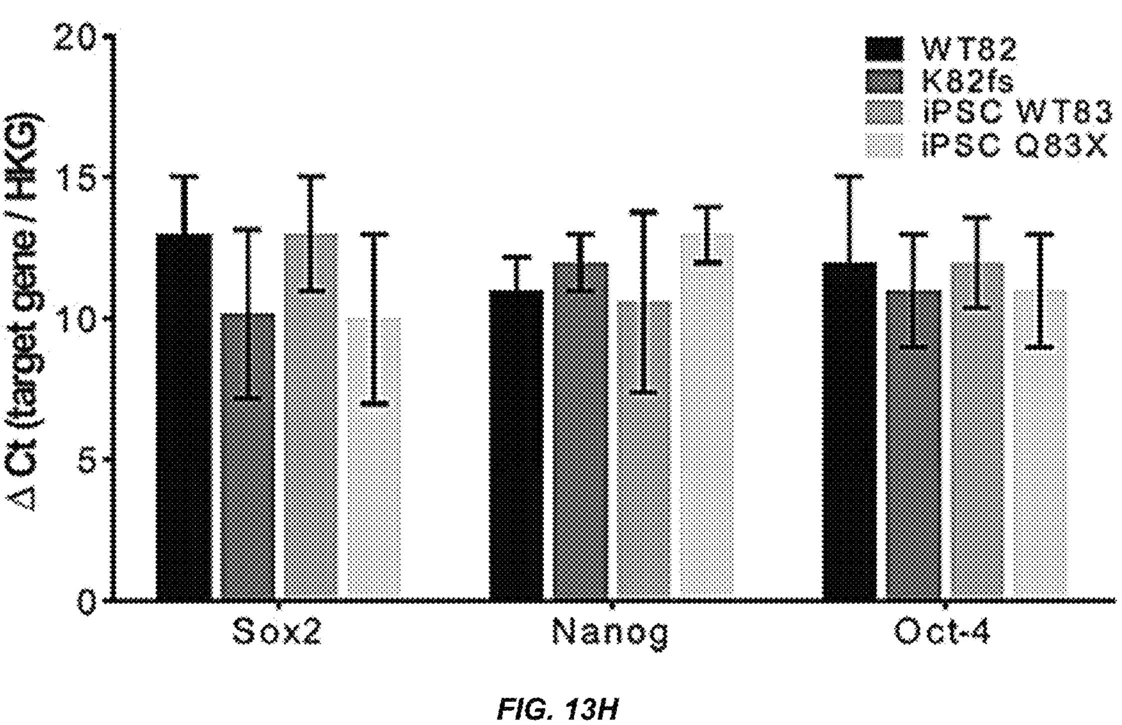
Figure 13I:
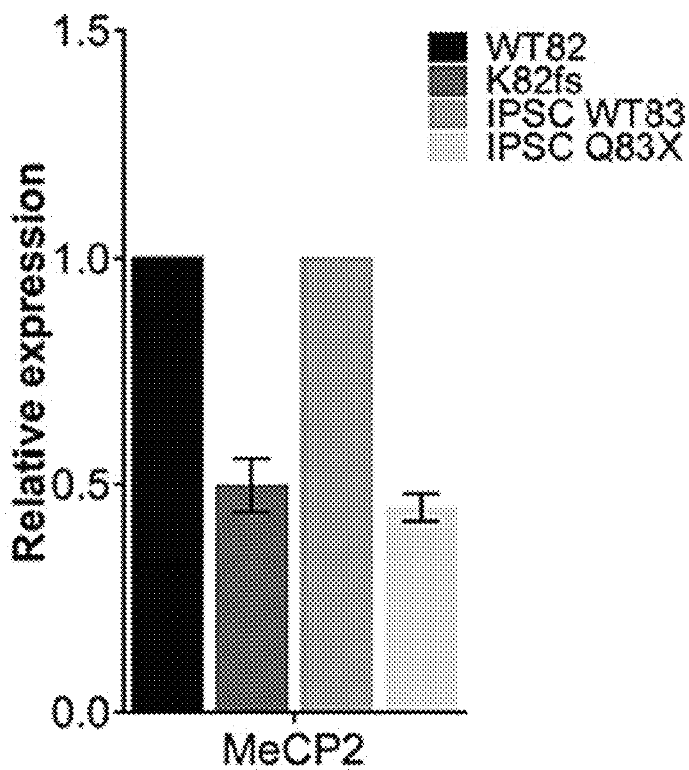
Figures 14A, 14B:
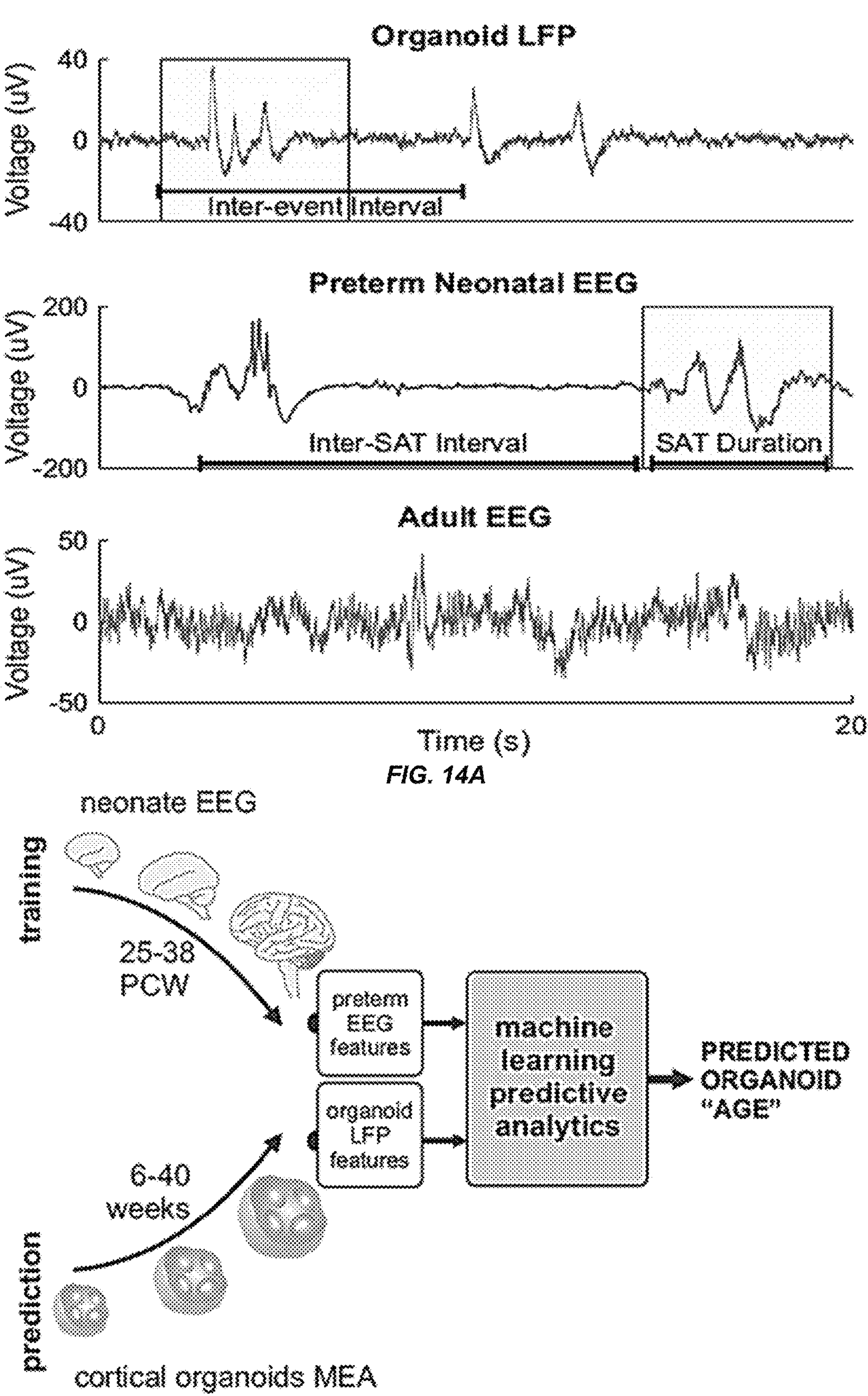
Figure 14C:
Figure 14C:
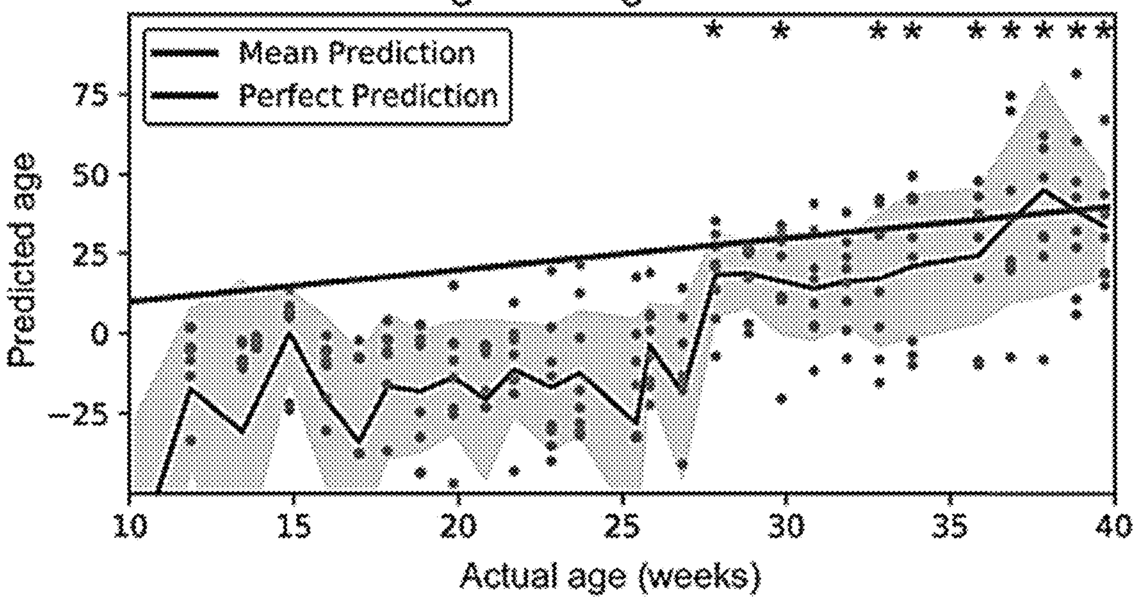
Figure 14D:
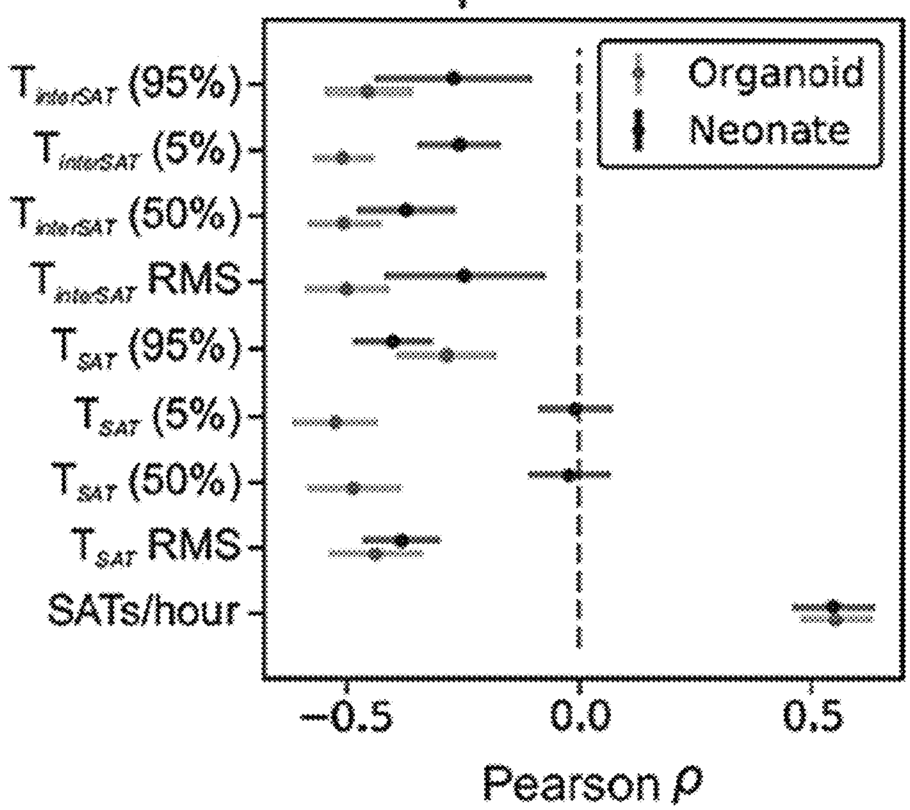
Figure 14E:
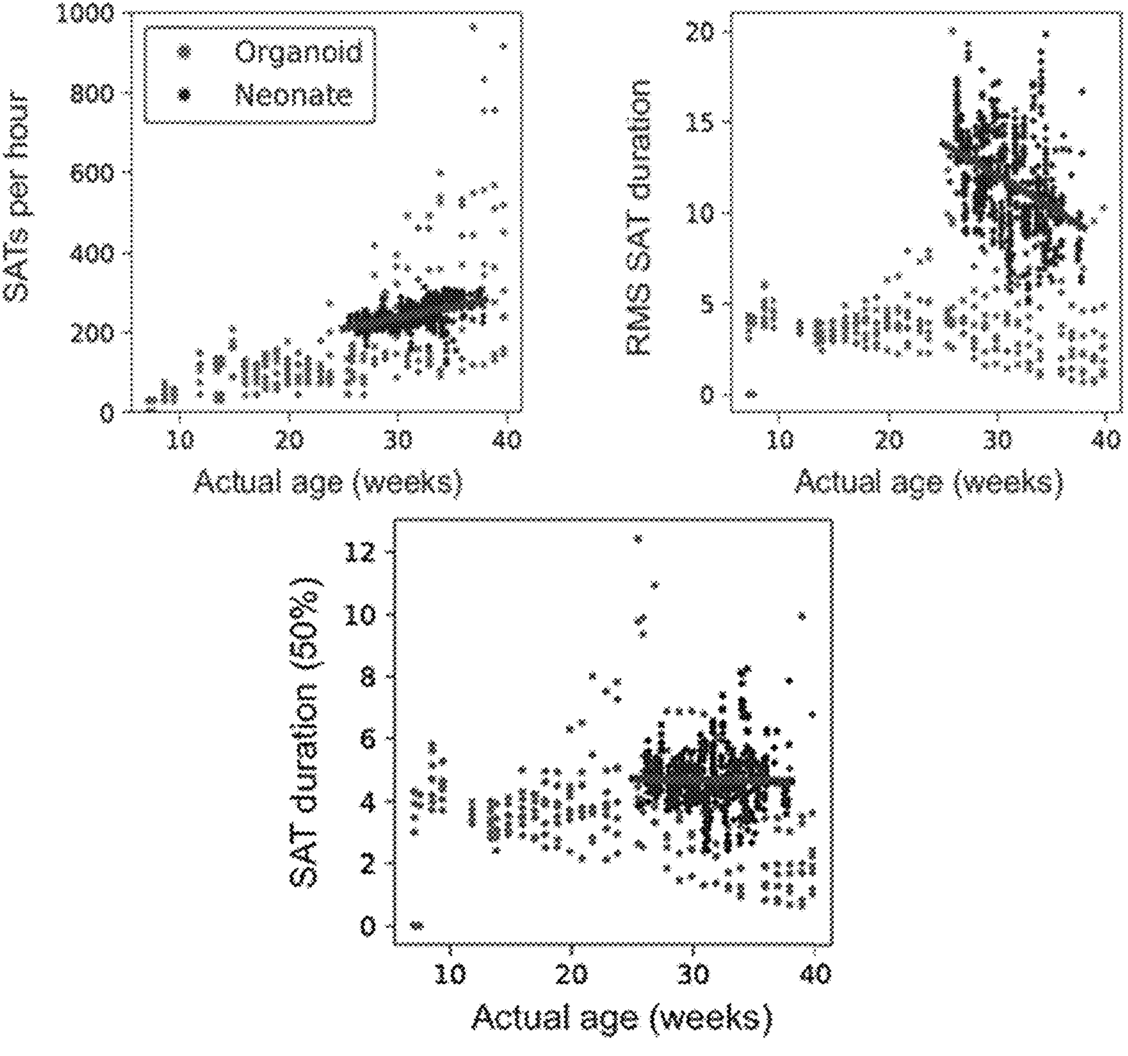

FIG. 12A-C shows oscillatory dynamics in cortical organoids mimic the bursting phenomenon in human electrophysiology. (A) An example tracing of an LFP recording in organoids (left) at two developmental time points, highlighting the instances of network events (right, zoomed in). Comparable events are shown in the human fetal brain culture and in the oscillatory burst in adult ECOG, and the respective highlighted events are zoomed in. Network events in organoids at late stages of development vary in latency and dynamics, similar to the activity observed in fetal tissue. (B) The oscillatory power in organoid LFP increases for up to the 25th week in culture and then plateaus. Inset, the oscillatory power is calculated by fitting a straight line (dashed) over the $1/f$ portion of the PSD; the heights of PSD peaks (highlighted) rising above the linear fit are computed as oscillatory power. (C) A spectral representation of time series data shown in (A). Spectrogram (left) of an organoid LFP that show bursts of activity localized at low frequency, while the PSD (right) displays canonical $1/f$ power law decay, and an oscillatory peak at approximately 2 Hz (arrow). Fetal tissue data and human ECOG also exhibit spatiotemporally localized oscillatory events.

FIG. 13A-I provides for the characterization of the MECP2-KO cell line. (A) Schematic overview of the MECP2 locus in iPSCs derived from fibroblasts of a male patient (Q83X), and CRISPR/Cas9 induced MECP2 mutation in an embryonic stem cell line (K82fs, H9 ESC). Q83X cell line characterization is shown elsewhere. DNA sequence chromatogram shows the nucleotide deletion in the MECP2 gene leading to a frameshift mutation (K82fs) and a predicted premature stop-codon in the end of exon 3 (asterisk). The WT82 and WT83 were used as controls. The Q83X and K82fs do not express MECP2 protein. Blue line represents the guide RNA target locus; SEQ ID NOs: 1-3, in order of appearance. (B) Gel images showing Surveyor nuclease assay of genomic DNA extracted from FACs sorted H9 ESC. Expected PCR products were 278 bp and 220 bp. (C) Exome sequencing analysis to evaluate CRISPR off-target mutations. Numbers indicate the amount of reads across the lines. Off-target gene mutations induced by MECP2 CRISPR/Cas9 are shown in the lower table. (D) Isogenic pairs of MECP2-mutant and control cell line colonies showing the expression of the pluripotency marker Nanog. Scale bar, 100 μm. (E) Eosin and Hematoxylin stains of teratomas showing the presence of all three germ layers. Scale bar, 200 μm. (F) Western blot of the isogenic pluripotent stem cells showing the absence of MECP2 in the mutant line. (G) Karyotypes of cell lines displaying no chromosomal abnormality. (H) and (I), Expression of pluripotency markers and MECP2 by qPCR. GAPDH was used as housekeeping gene.

FIG. 14A-E demonstrates the organoid network dynamics mimic premature neonates after 28 weeks of maturation. (A) Representative LFP trace from cortical organoid, highlighting instances of network events (yellow). Comparable events between periods of quiescence (discontinuous network dynamics) are shown in human preterm neonate EEG at 35 weeks gestational age, while a different pattern of continuous activity is observed in adult EEG. SAT: spontaneous activity transient. (B) Schematic of machine learning architecture for organoid "brain-age" prediction: 9 EEG features from 39 premature babies (567 recordings) between 25 and 38 PCW were used to train and cross-validate a regularized regression model to predict organoid age. (C) Predicted organoid "brain age" (determined by neonate model) plotted against actual organoid age. Black stars denote time points where mean predicted age is not significantly different from actual age under 1-sample t-test ($P<0.05$. $n=8$). (D) Resampled Pearson's correlation coefficient between age and electrophysiological features for both organoid and premature neonates show different degrees of developmental similarity for individual features. (E) EEG/LFP features over time for organoids and premature neonates.

Figure 15A:
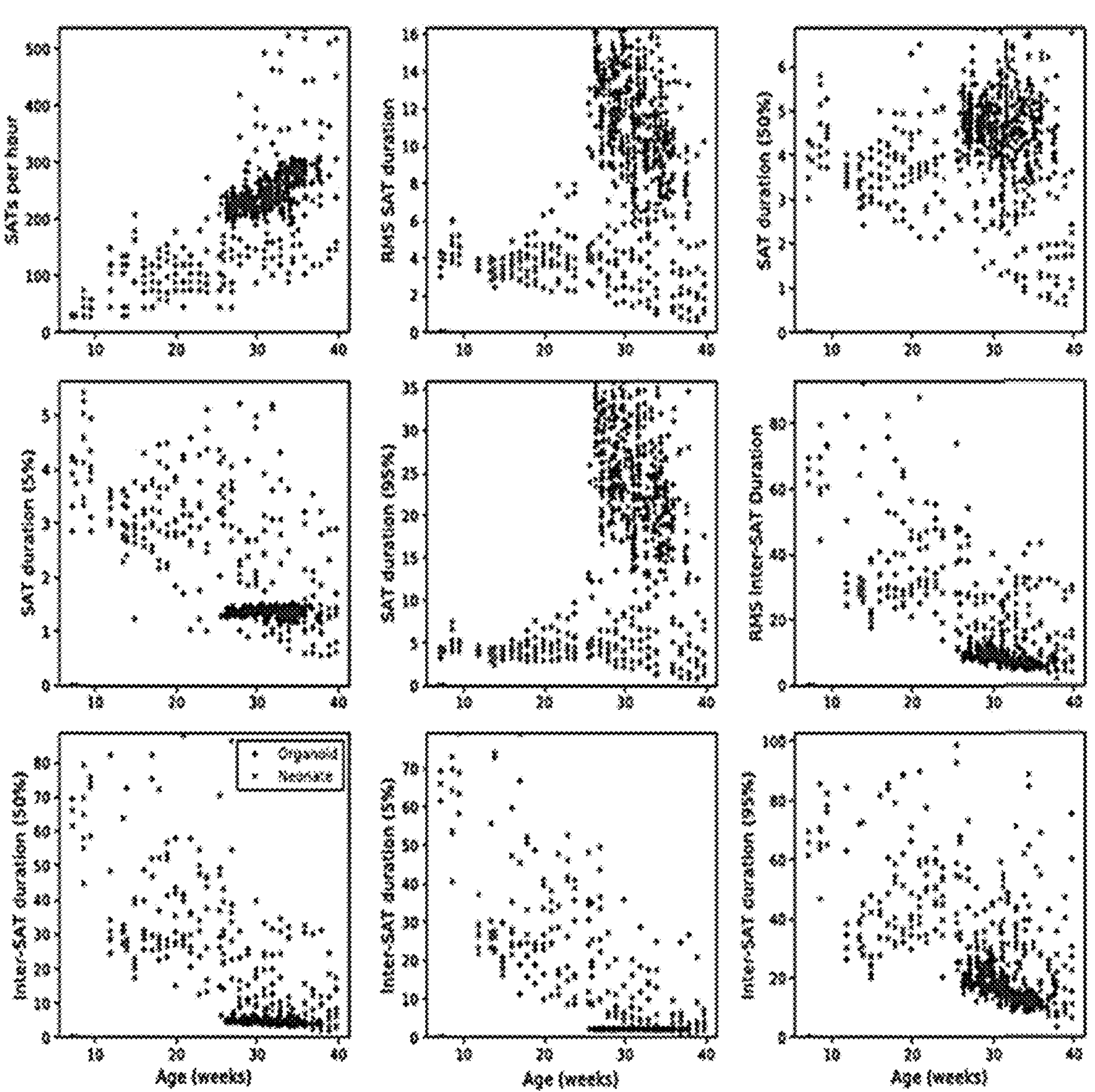
Figures 15B, 16A, 16B:
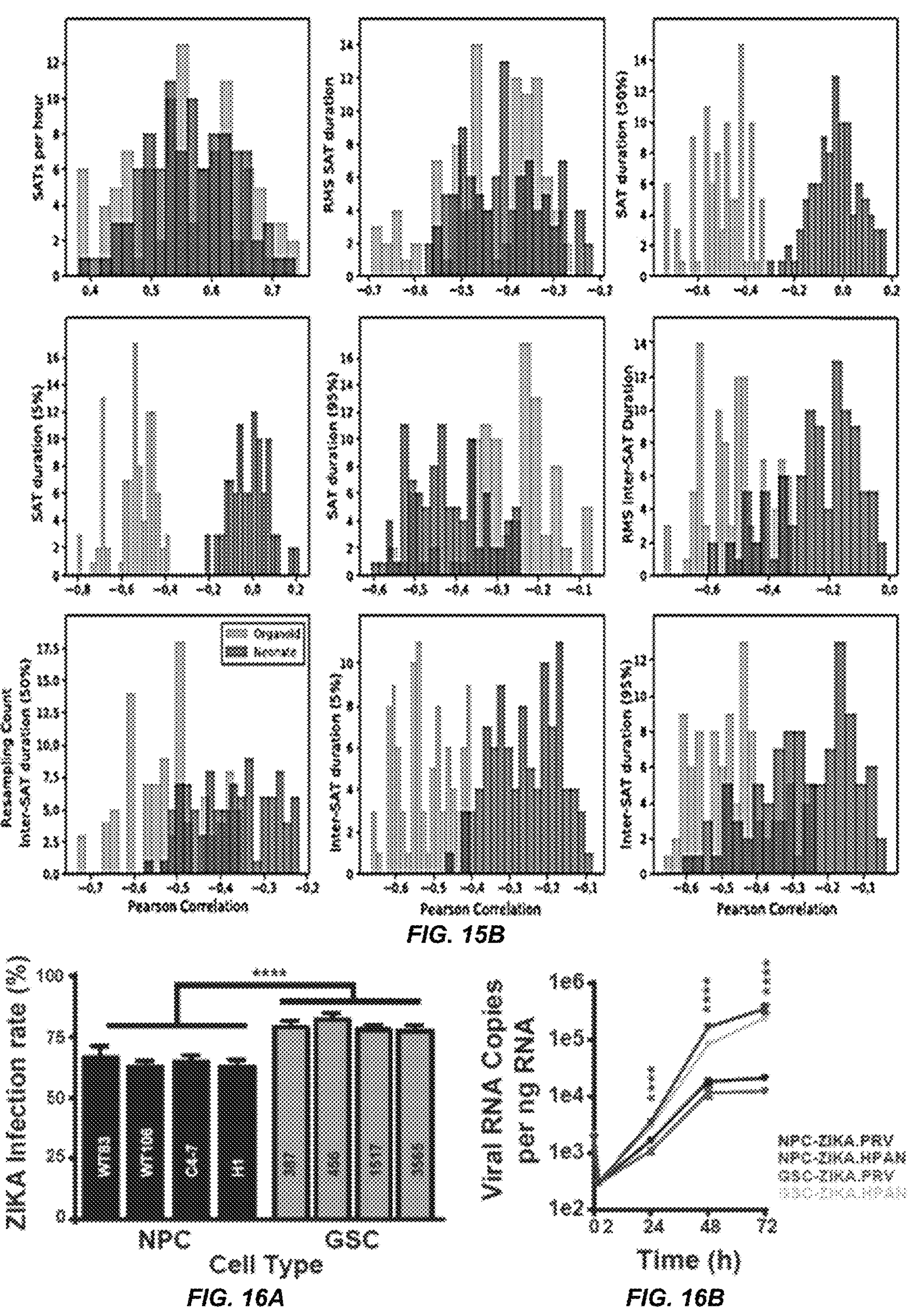

FIG. 15A-B demonstrates that the network activity in cortical organoids mimics oscillatory features in the developing human brain. (A) Comparison of 9 preterm neonate EEG and cortical organoid features over time. For included EEG features, see Table 3. (B) Distributions of resampled Pearson correlation coefficients between feature and age for preterm neonate and organoid.

FIG. 16A-E shows that Zika virus (ZIKV) infects and kills glioblastoma stem cells (GSCs) more efficiently than neural precursor cells (NPCs). (A) Quantification of infection efficiency in four GSC and NPC lines 48 hours after ZIKV-HPAN infection (MOI: 5 FFU/cell). Data were pooled from three technical replicates with two biological replicates. Values represent mean±SD. *, $p<0.0001$ by one-way ANOVA with Tukey's multiple comparison test. (B) Kinetics of viral RNA copies following ZIKV infection (MOI: 0.1 FFU/cell) by measuring viral RNA copies by qRT-PCR in hNPC-C47 and GSC3565 at the indicated time points. Cell death precluded collection of RNA from parental and control cells at some time points. Data were pooled from three technical replicates and with two biological replicates. Values represent mean±SD. **** $p<0.0001$. by one-way ANOVA with Tukey's multiple comparison test. (C) Cell viability normalized to day 0 as measured by CellTiter-Glo assay after 5 days of mock conditions or ZIKV infection (MOI: 5 FFU/cell) for GSCs, NPCs, and primary astrocytes. Each data set was pooled from three technical replicates with two biological replicates. Values represent mean±SD. NS, not significant: *, $p<0.0001$ by one-way ANOVA with Tukey's multiple comparison test correction compared to control. (D) GSCs (GSC3565) and NPCs (hNPC-C47) were cultured under serum-free conditions to maintain stemness or serum conditions to induce differentiation into differentiated glioma cells (DGC) and differentiated NPC (astrocytes/neurons). Cultures were then treated with mock conditions or infected with ZIKV-PRV (MOI: 0.1, 1, and 5) with viability assayed after 72 hours by CellTiter-Glo. Each data set was pooled from three technical replicates with two biological repeats. Values represent mean±SD. ** $p<0.0001$ by one-way ANOVA with Tukey's multiple comparison test between serum-free and differentiation conditions. (E) Quantification of percentage of cleaved caspase 3-positive cells in DAPI-positive cells for GSCs and NPCs 72 hours in mock conditions or after ZIKV-PRV infection (MOI: 5 FFU/cell). Data were pooled from three technical replicates with two biological repeats. Values represent mean±SD. **. $p<0.0001$ by one-way ANOVA with Tukey's multiple comparison test.

Figures 17A, 17B, 18A:
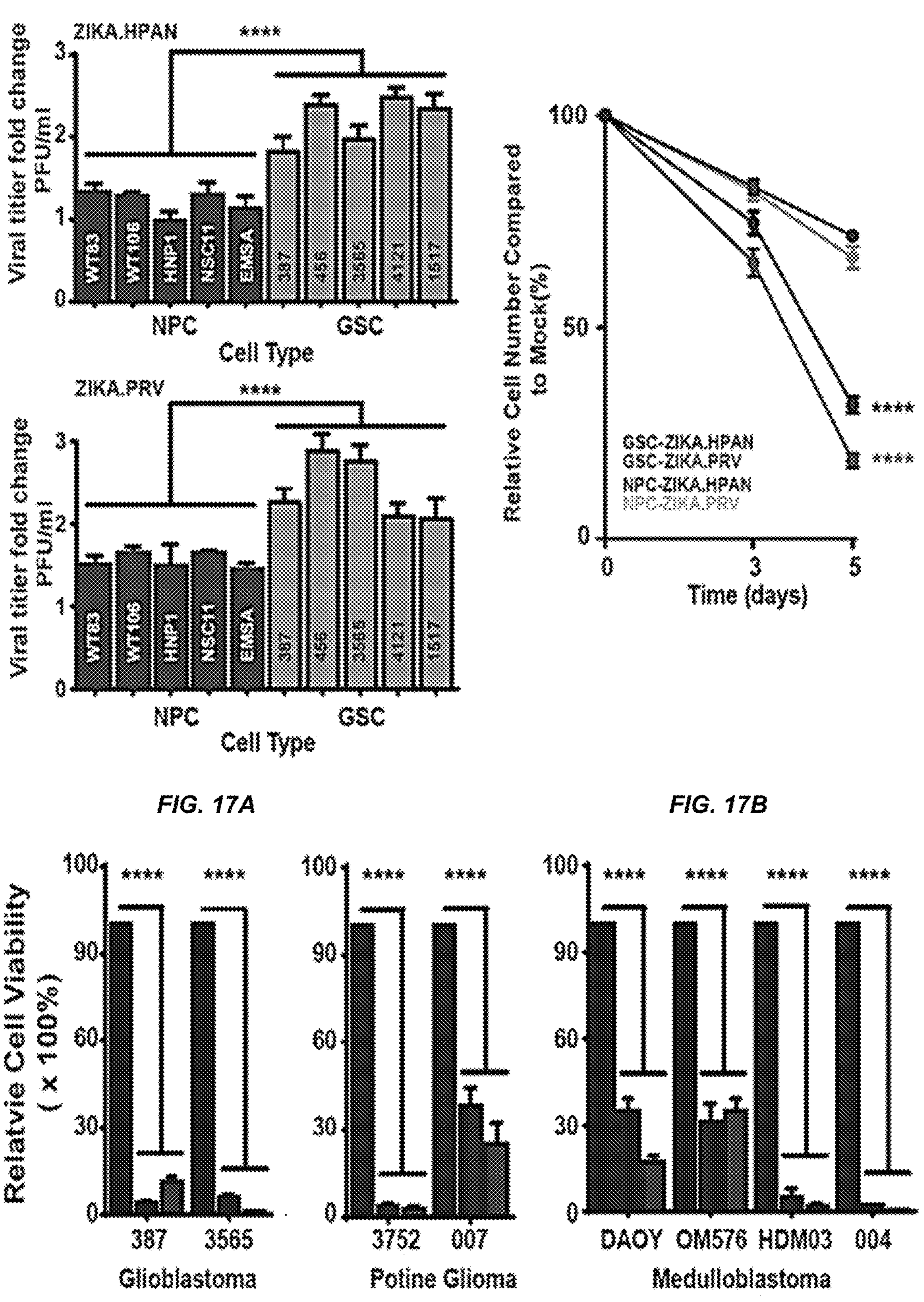

FIG. 17A-B demonstrates that Zika virus (ZIKV) infects and kills glioblastoma stem cells (GSCs) more efficiently than neural precursor cells (NPCs). (A) Plaque assays were used to determine viral titers of NPCs and GSCs four days post infection with either ZIKA.PRV or ZIKA.HPAN at MOI of 0.1 FFU/cell. Values represent mean±SD and were normalized to day 0 levels as fold change. Data were pooled from three technical replicates and performed in two biological repeats. ** , $p<0.0001$ by one-way ANOVA with Tukey's multiple comparison test. (B) GSCs (GSC3565) and NPCs (hNPC-C47) were treated with mock conditions or infected with ZIKV.PRV or ZIKV.HPAN (MOI: 5) with viability assayed over 5 days by Cell TiterGlo. Each data set was pooled from three technical replicates with two biological repeats. Values represent mean±SD. ** , $p<0.0001$ by one-way ANOVA with Tukey's multiple comparison test between serum-free and differentiation conditions.

Figure 18A:
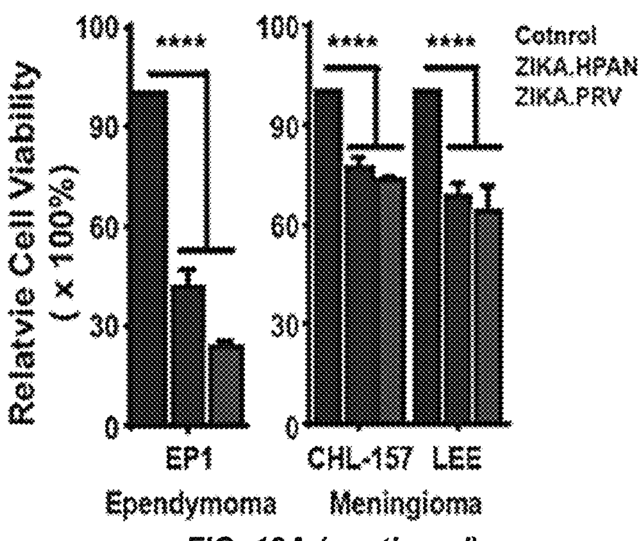
Figure 18B:
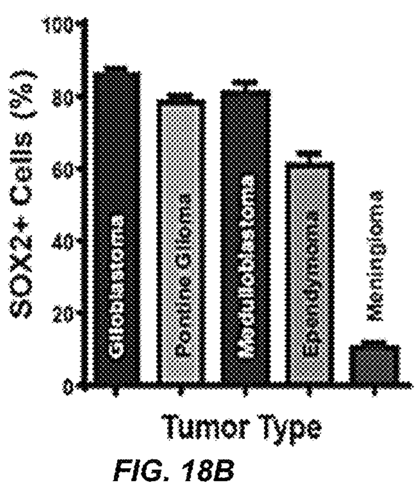

FIG. 18A-B shows that ZIKV attenuates growth of pontine glioma. medulloblastoma, and ependymoma models in vitro with lesser effect against meningioma. (A) Patient-derived cultures from glioblastoma (387 and 3565), pontine glioma (3752 and 007), meningioma (CHL-157, LEE), and ependymoma (EP-1), as well as medulloblastoma cell lines (DAOY, D283, HDMB03, D341) were infected with ZIKA-PRV (MOI: 5). Cell viability after 72 hours was measured by CellTiter-Glo. Data were pooled from three technical replicates and performed in two biological repeats. Values represent mean±SD. ****, $p<0.0001$ by one-way ANOVA with Tukey's multiple comparison test. (B) Quantification of $SOX2^{+}$ cells in different brain tumor models used in (A) with two independent repeats.

Figure 19A:
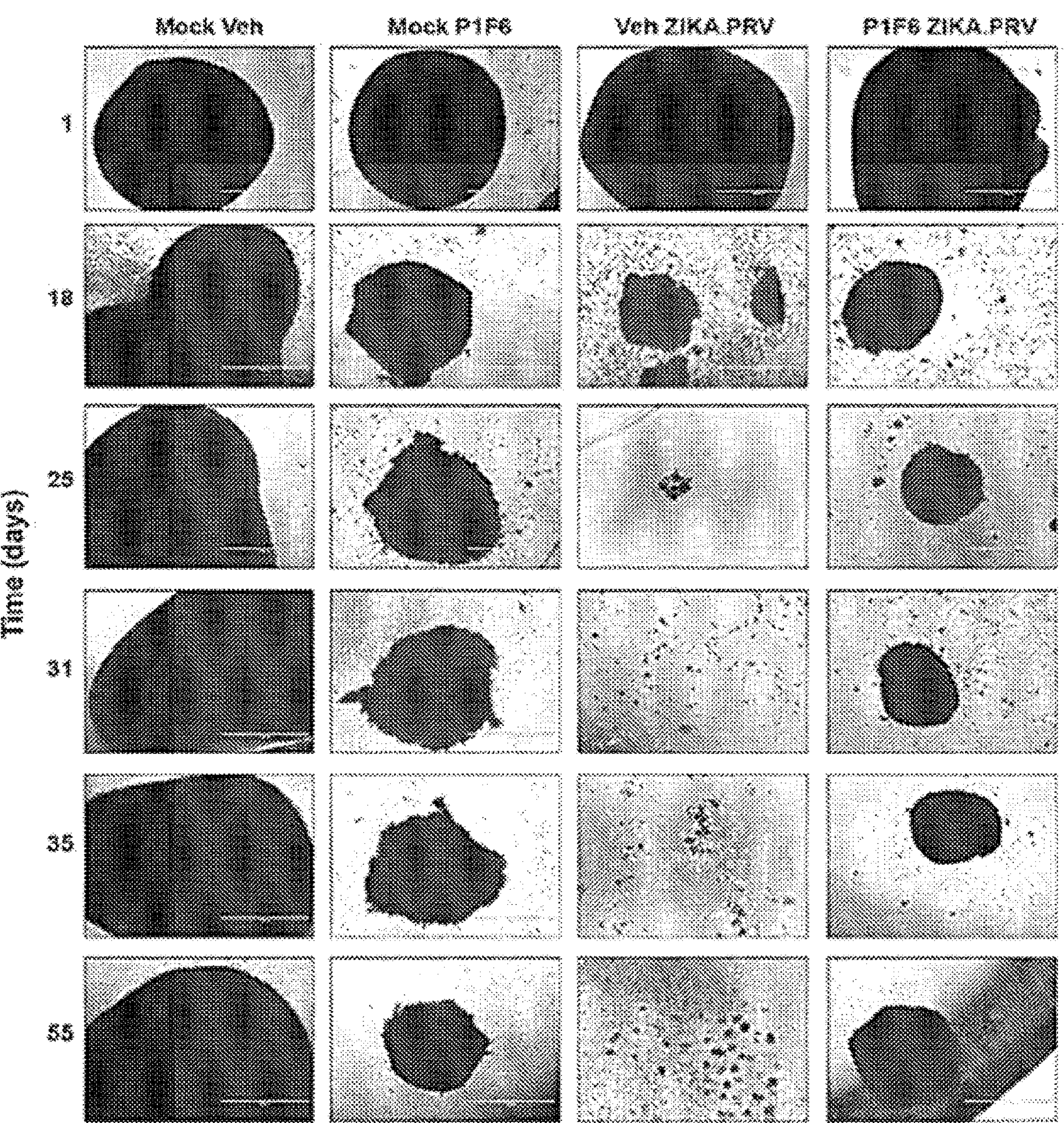
Figure 19B:
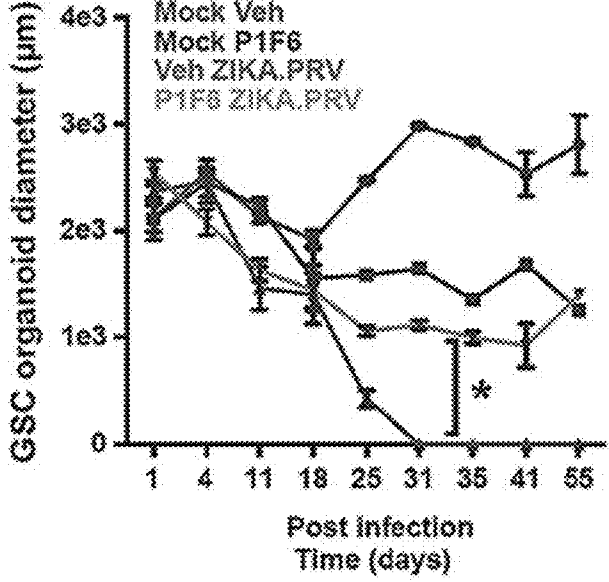

FIG. 19A-B demonstrates that GSC-derived organoids are ablated by ZIKV infection in an integrin $\alpha_v\beta_5$-dependent manner. (A) Organoids were derived from GSC3565 and subjected to treatment with mock conditions, a neutralizing antibody against integrin $\alpha_v\beta_5$ (P1F6 at 50 μg/mL twice a week), ZIKV.PRV infection (MOI: 5 FFU/cell), or the combined antibody and ZIKV treatment. Brightfield images were taken over a time course until day 55. N=5. Scale bars, 1 mm. (B) GSC-derived organoids from (A) were assayed for their diameter over a time course. *, $p<0.05$ by one-way ANOVA with Tukey's multiple comparison test.

Figure 20A:
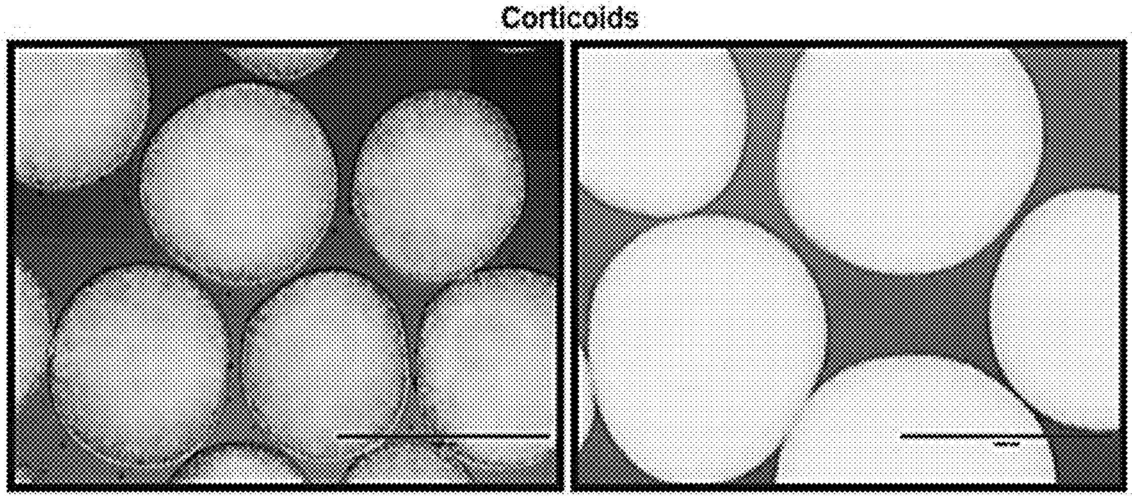
Figure 20B:
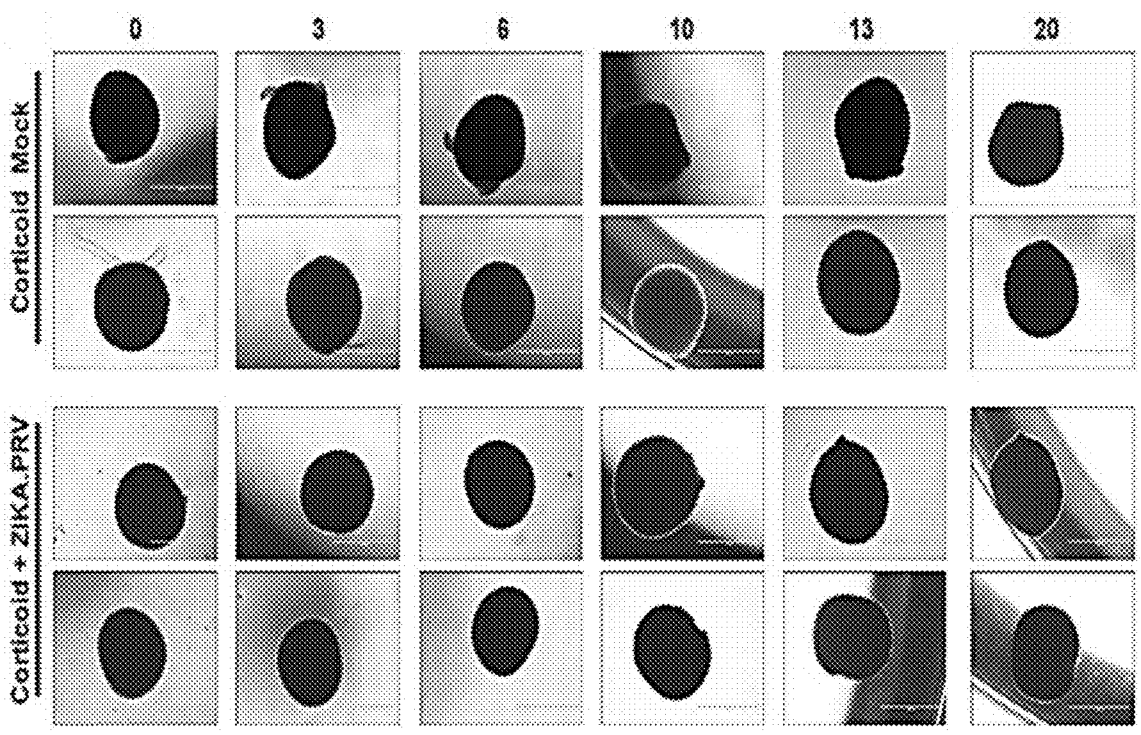
Figure 21A:
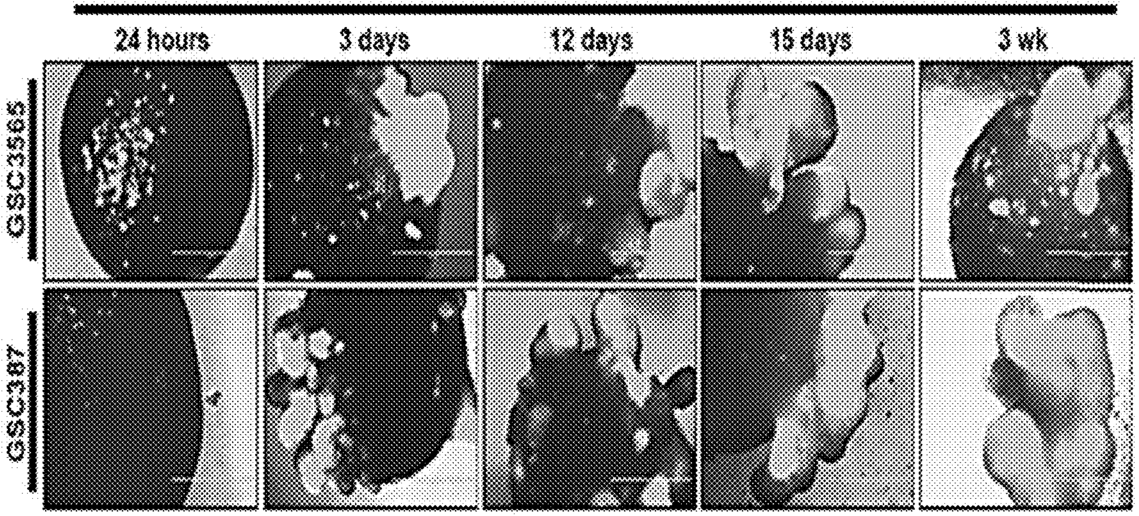
Figures 21B, 21C, 21D, 21E:
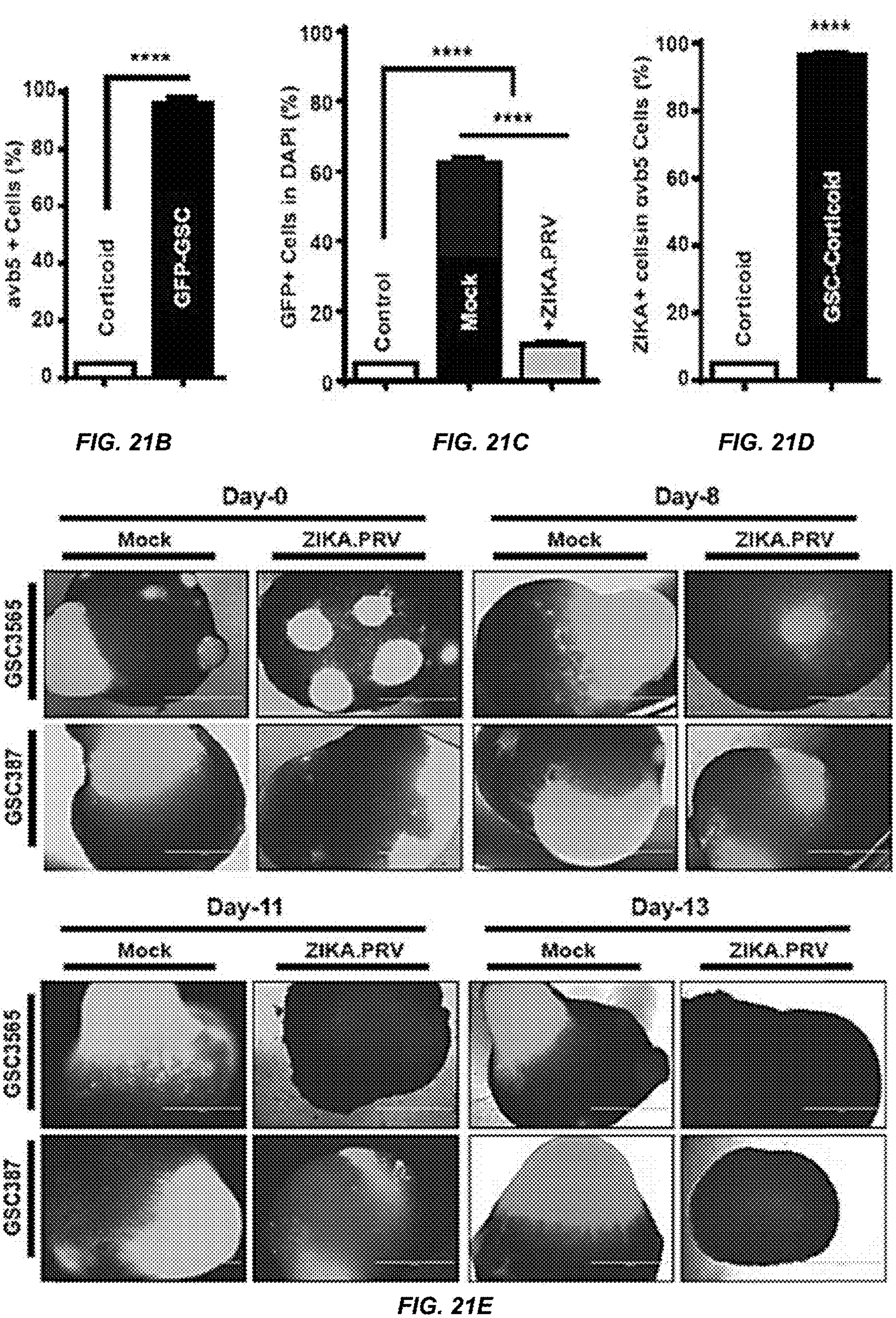
Figures 22A, 22B:
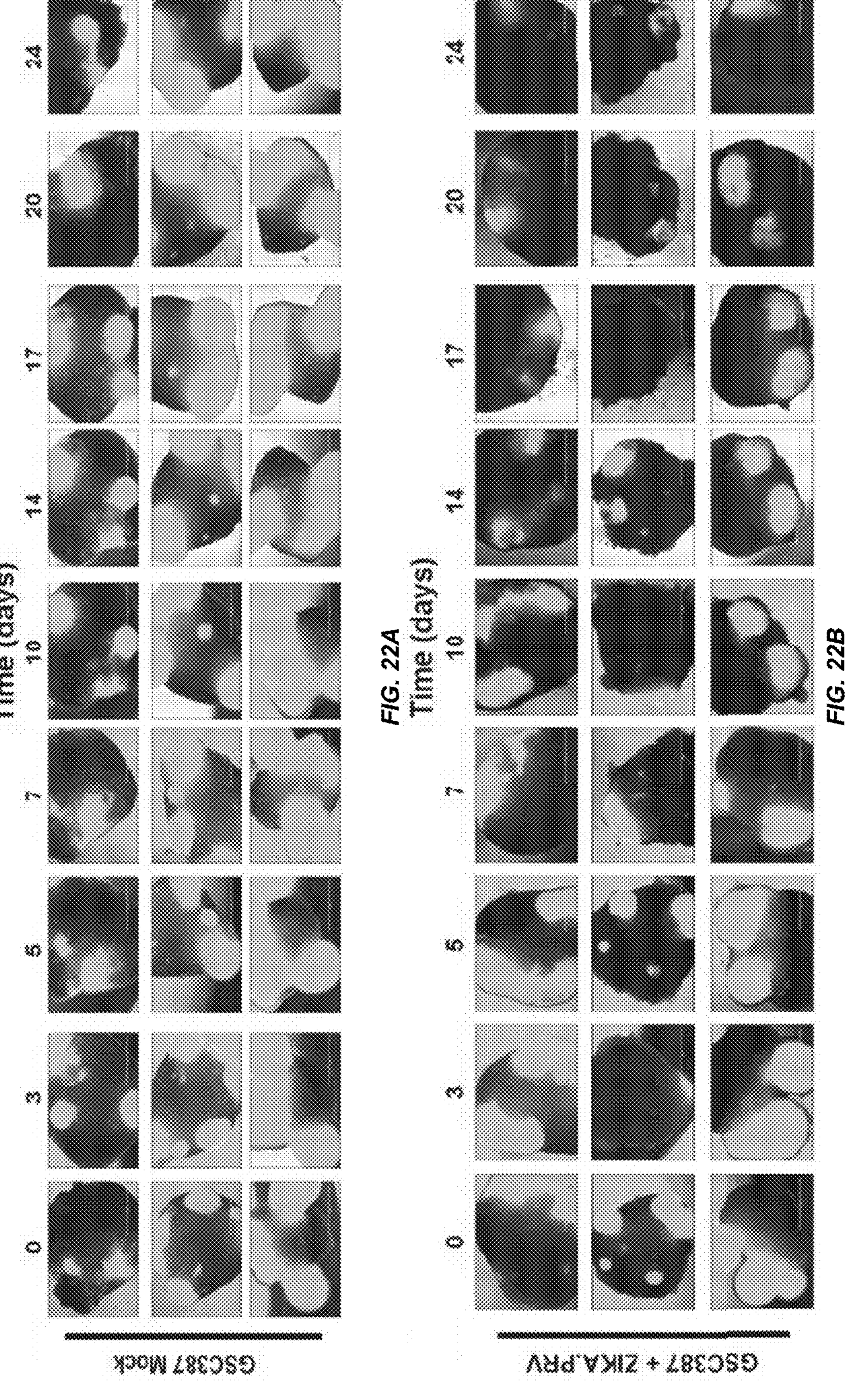
Figures 22C, 22D:
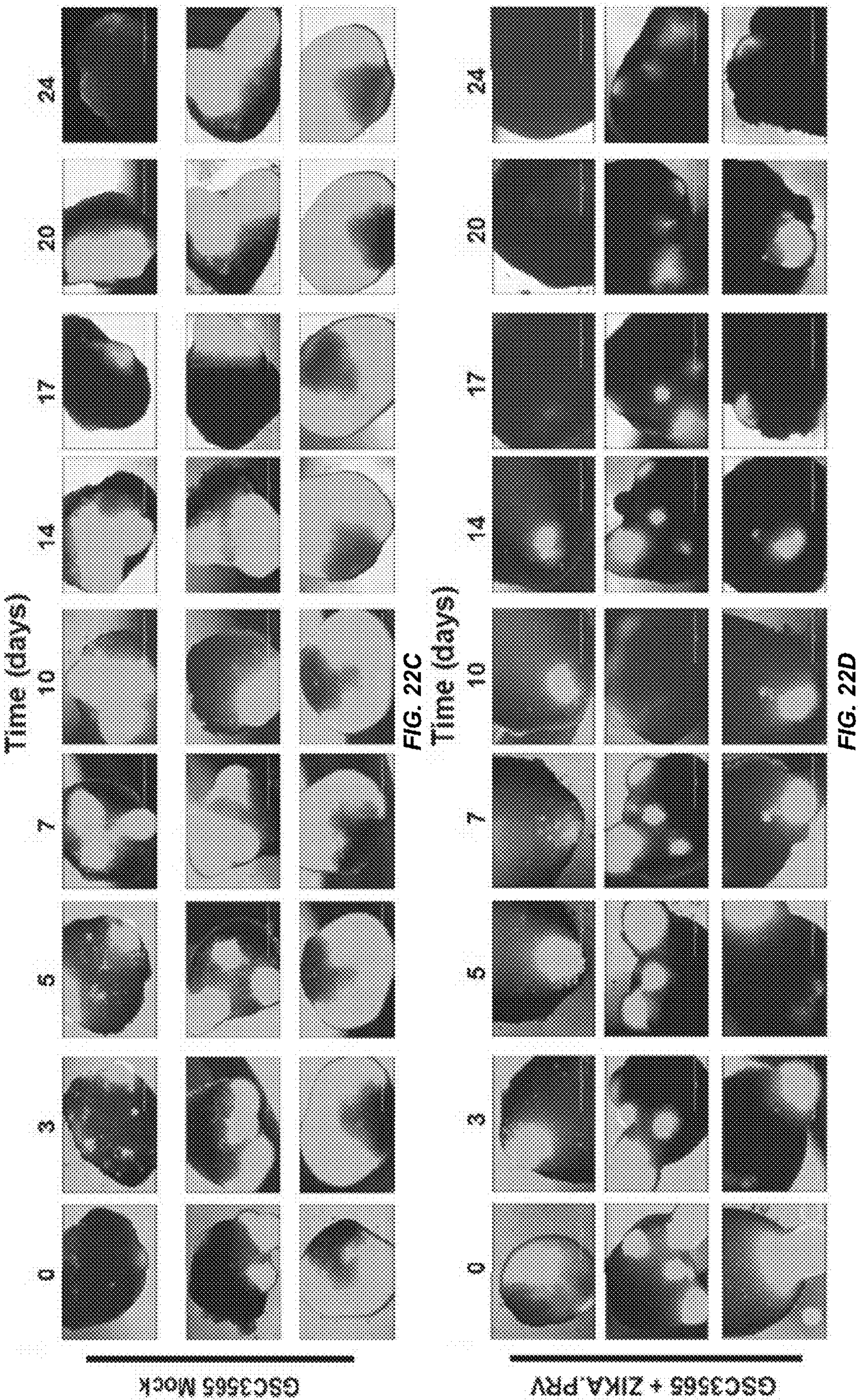
Figure 22E:
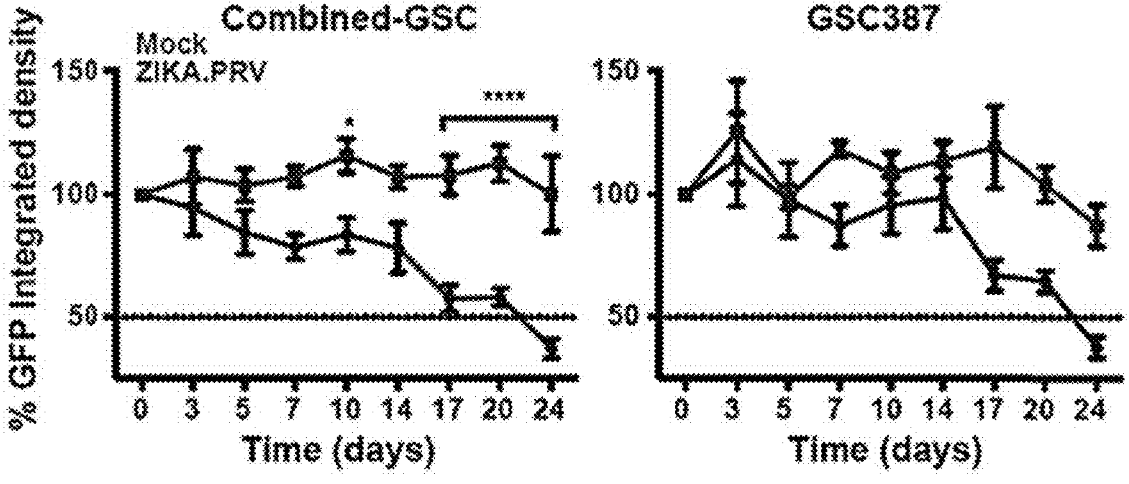
Figure 22E:
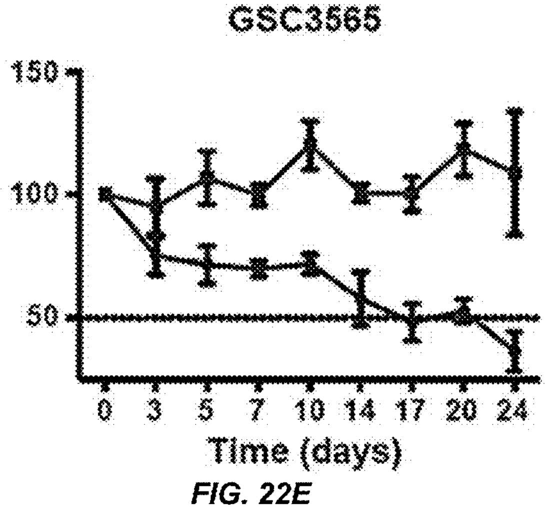

FIG. 20A-B demonstrates that ZIKV has limited toxicity against normal cortical organoids (corticoids). (A) Representative brightfield images of cortical organoids (corticoids) derived from induced pluripotent stem cells showing established corticoids (left, 1 month; right, two months). Scale bar, 1 mm. (B) Representative brightfield images of corticoids derived from induced pluripotent stem cells that were subjected to mock conditions or infected with ZIKA.PRV (MOI: 5 FFU/cell) over a time course until 20 days post infection. Scale bar, 1 mm.

FIG. 21A-E shows that Zika infection preferentially targets glioblastoma in glioblastoma-corticoid models. (A) Brightfield images of engraftment of two patient-derived glioma stem cell models (387 and 3565) transduced with GFP into human corticoids over a time course. Scale bar, 1 mm. (B) Quantification of integrin $\alpha_v\beta_5$-positive cells in normal corticoids or GSC-corticoids. Values represent mean±SD. N=6. **, $p<0.0001$ by Student's t-test. (C) GFP-labeled GSC-GFP brain corticoids were cultured under mock conditions or with ZIKV.PRV (MOI: 5 FFU/cell) for 2-4 weeks. The percentage of GFP-positive cells in DAPI-positive cells was quantified. Values represent mean≅SD. N=6, , $p<0.0001$ by two-way ANOVA with the Bonferroni multiple comparison test. (D) GFP-labeled GSC-GFP brain corticoids were cultured under mock conditions or with ZIKV.PRV (MOI: 5 FFU/cell) for 2-4 weeks. The percentage of ZIKV envelope protein positive in integrin $\alpha_v\beta_5$ cells was quantified. Values represent mean±SD. N=6. **, $p<0.0001$ by Student's t-test. (E) GFP-labeled GSC-GFP brain corticoids were cultured under mock conditions or with ZIKV.PRV (MOI: 5 FFU/cell) and monitored until 13 days after infection. Scale bar, 1 mm.

FIG. 22A-E ZIKV infection preferentially targets glioblastoma in glioblastoma-corticoid models. (A-D) shows cerebral organoids (corticoids) that were derived from induced pluripotent stem cells then confronted with GFP-labeled GSCs (387 or 3565), permitting integration. Brightfield images showing GSC-corticoids after being subjected to mock conditions or infection with ZIKA.PRV (MOI: 5 FFU/cell) were taken over a time course until day 24 (Scale bars, 1 mm): (A) 387 GSC-corticoids under mock conditions; (B) 387 GSC-corticoids with ZIKA.PRV infection (MOI: 5 FFU/cell): (C) 3565 GSC-corticoids under mock conditions; and (D) 3565 GSC-corticoids with ZIKA.PRV infection (MOI: 5 FFU/cell). (E) GFP integrated density was measured using Image J software. *, $p<0.05$; ***, $p<0.0001$ by one-way ANOVA with Tukey's multiple comparison test.

DETAILED DESCRIPTION

As used herein and in the appended claims, the singular forms "a," "an," and "the" include plural referents unless the context clearly dictates otherwise. Thus, for example, reference to "a neurosphere" includes a plurality of such neurospheres and reference to "the organoid" includes reference to one or more organoids and equivalents thereof known to those skilled in the art, and so forth.

Unless defined otherwise, all technical and scientific terms used herein have the same meaning as commonly understood to one of ordinary skill in the art to which this disclosure belongs. Although many methods and reagents are similar or equivalent to those described herein, the exemplary methods and materials are disclosed herein.

All publications mentioned herein are incorporated by reference in full for the purpose of describing and disclosing methodologies that might be used in connection with the description herein. The publications are provided solely for their disclosure prior to the filing date of the present application. Nothing herein is to be construed as an admission that the inventors are not entitled to antedate such disclosure by virtue of prior disclosure. Moreover, with respect to any term that is presented in one or more publications that is similar to, or identical with, a term that has been expressly defined in this disclosure, the definition of the term as expressly provided in this disclosure will control in all respects.

Development of functional human brain networks is an activity-dependent process guided by genetic and molecular programs and shaped by emerging cellular diversity. Neonate neural networks share many features with adult brains, despite the fundamental structural differences. Even though the chronological stages of the human cortical network formation are not well understood, it is suggested that emerging cognitive functions during infancy are a result of different brain regions and environmental cues. However, in uterus development is vital for the establishment of neuronal circuitry and healthy functioning of the brain. The second and third trimester of gestation are when the corticothalamic network is formed via transient connections of the subplate GABAergic neurons and the emergence of synchronized network activity. Thus, early cortical functional maturation follows an independent sensory-input pathway, guided by spontaneous activity and associated with synaptic regulating mechanisms.

For purposes of the disclosure the term "cancer" will be used to encompass cell proliferative disorders, neoplasms, precancerous cell disorders and cancers, unless specifically delineated otherwise. Thus, a "cancer" refers to any cell that undergoes aberrant cell proliferation that can lead to metastasis or tumor growth. Exemplary cancers include but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, including triple negative breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver)

cancer, Hodgkin lymphoma, hypopharyngeal cancer, intraocular melanoma, ocular cancer, islet cell tumors (endocrine pancreas). Kaposi Sarcoma, kidney cancer, renal cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma. Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, soft tissue sarcoma, uterine cancer, uterine sarcoma, skin cancer (non-melanoma), skin cancer (melanoma), papillomas, actinic keratosis and keratoacanthomas, merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor.

As used herein, the term "cancer cells" refers to cells that cells that divide uncontrollably, forming solid tumors or flooding the blood with abnormal cells. As used herein the term "cancer cells" includes cancer stem cells, unless indicated otherwise.

As used herein, the term "cancer stem cells" refers cancer cells (found within tumors or hematological cancers) that possess characteristics associated with normal stem cells, specifically the ability to give rise to all cell types found in a particular cancer sample. Cancer stem cells may generate tumors through the stem cell processes of self-renewal and differentiation into multiple cell types. Such cells are hypothesized to persist in tumors as a distinct population and cause relapse and metastasis by giving rise to new tumors.

As used herein, the term "cortical plate folding" refers to folding seem with an immature cortex, which enlarge the surface area of the cortex and are thought to create more space for higher functions including thought and action.

As used herein, the term "differentiation" refers to the process where a cell changes from one cell type to another, e.g., an NPC differentiates into a neuron or glial cell. Differentiation dramatically changes a cell's size, shape, membrane potential, metabolic activity, and responsiveness to signals. These changes are largely due to highly controlled modifications in gene expression.

As used herein, the term "functional cortical organoids" refers to artificially grown, in vitro, miniature organs that contain well-organized neural progenitor cell (NPC) layers and neuronal layers that are further characterized by producing nested oscillatory waves, e.g., oscillatory waves comparable electroencephalography (EEG)-like network activity upon differentiation. The "functional cortical organoids" can be further characterized by the gene expression profiles, electrophysiological features, and other characteristics presented herein in this disclosure. Compared with cerebral organoids, brain region-specific organoids, like cortical organoids, model individual brain regions of interest and generally result in more uniform and reproducible tissue, providing a platform for quantitative characterization.

As used herein, the term "high throughput screening" refers to a method for scientific experimentation especially used in drug discovery that can rapidly identify active compounds, antibodies, or genes that modulate a particular biomolecular pathway. High-throughput screening allows a researcher to quickly conduct thousands if not millions of chemical, genetic, or pharmacological tests. Typically, "high throughput screening" is automated by use of robotics, data processing/control software, liquid handling devices, and sensitive detectors.

As used herein, the term "neurodegenerative insult" refers to an action, such as by exposure to a chemical, microorganism, substance, or injury, etc., that leads to neurodegeneration. Examples of "neurodegenerative insults" include, but are not limited to, reperfusion injuries, protein aggregation (e.g., Alzheimer's or Parkinson associated proteins), reactions of free radicals, insufficient blood supply, glutamate excitotoxicity, and oxidative stress.

As used herein the term "neurological disease", "neurological disorder" or "neurological condition" refers to a disease of the brain, spine and nerves that connect them. There are more than 600 diseases of the nervous system, such as brain tumors, epilepsy, Parkinson's disease and stroke. Major types of neurological diseases, disorders or conditions include, but are not limited to, diseases caused by faulty genes (e.g., Huntington's disease and muscular dystrophy); problems with the way the nervous system develops (e.g., spina bifida); degenerative disease where nerve cells are damaged or die (e.g., Parkinson's disease or Alzheimer's disease); diseases of the blood vessels that supply the brain (e.g., stroke); injuries to the spinal cord or brain; seizure disorders (e.g., epilepsy); cancer (e.g., brain tumors); and infections (e.g., meningitis).

As used herein, the term "neuroprotective effect" refers to a compound or agent that has the effect of preserving neuronal structure and/or function. In the case of a neurodegenerative insult, the compound or agent provides for the relative preservation of neuronal integrity, such that the rate of loss of neural integrity is reduced in the presence of the compound or agent than without.

As used herein, the term, "nonessential amino acids" refers to amino acids that can be made by a subject and is therefore not essential to the subject's diet. For humans, there are 11 nonessential amino acids: alanine, arginine, asparagine, aspartic acid, cysteine, glutamic acid, glutamine, glycine, proline, serine, and tyrosine.

As used herein, the term "neural progenitor cells" or "NPCs" refers to cells capable of dividing a limited number of times and have the capacity to differentiate into a restricted repertoire of neuronal and glial cell types.

As used herein, the term "neurobasal media" refers to cell or organoid growing basal medium that is designed for long-term maintenance and maturation of pure pre-natal and embryonic neuronal cell populations without the need for an astrocyte feeder layer when supplemented. Neurobasal media is commercially available from a variety of vendors, including ThermoFisher Scientific, VWR, Sigma Aldrich, US Bio, and STEMCELL Technologies.

As used herein, the term "oscillatory waves" refers to rhythmic or repetitive patterns of neural activity.

As used herein, the term "pyramidally-shaped neurons" refers to a multipolar neuron that has a conic shaped cell body.

As used herein, the term "serum-free" refers to cell or organoid growing media that is animal component-free. Serum-free media has fewer undefined components that serum containing media and generally is lower in protein content than media which has supplemented with serum, such as fetal bovine serum.

As used herein, the term "stem cells" refers to an undifferentiated cell of a multicellular organism that is capable of giving rise to indefinitely more cells of the same type, and from which certain other kinds of cell arise by differentiation.

As used herein, the term "supplemented neurobasal media" refers to neurobasal media that has been supplemented with factors and growth agents that promote the survival, growth and differentiation of neuronal cells. Supplements for neurobasal media can be purchased from a variety of vendors, including B-27™ Plus, N-2 and GlutaMAX™ supplements from ThermoFisher Scientific, NeuroCult™ and STMdiff™ supplements from STEMCELL Technologies, GEM21 NeuroPlex™ and N2 NeuroPlex™ from Gemini Bio-Products, and NDiff™ supplements from Sigma Aldrich.

As used herein, the term "vehicle control" refers to substance that is used as a vehicle for a solution of the experimental compound or drug product, which is used alone and is administered in the same manner as it is used with the experimental compound or drug product. Typically, the "vehicle control" is innocuous and does not change the activity of the cells or functional cortical organoids disclosed herein.

It is reported herein the formation of small-scale functional electrophysiological networks in cortical organoids, similar to those observed in the developing brain. The generation of cerebral organoids from induced pluripotent stem cells (iPSCs) offers a three-dimensional framework to study the developing human brain. Organoids generated from induced pluripotent stem cells (iPSC) provide a scaled-down and three-dimensional model of the human brain, mimicking various developmental features at the cellular and molecular level. Despite recent advances in the understanding of their vast cellular diversity, there is no evidence that these organoids show complex and functional neural network activity that resembles early human brain formation. Therefore, researchers have not yet clearly determined whether organoids are a suitable model for studying brain activity.

The present disclosure describes the use of human iPSCs to generate an enriched pyramidal cortical population that self-assembles into functional network units over the span of several months. The method was designed (i) to provide a versatile organoid technology platform without the need for specialized equipment, (ii) to overcome structural and functional variability issues, (iii) to decrease the exposure to an excess of growth factors that would benefit for future disease modeling studies, and (iv) to develop a mature functional network system exhibiting EEG-like activity that would allow the direct interrogation of human cortical features. Further, investigations were directed to use of the organoids to study the molecular basis of human brain oscillatory activity formation, maintenance, and temporal control by targeting specific genes. Machine learning predictive analytics were applied to the organoids to evaluate the similarity between electrophysiological activity patterns of the in vitro model and human preterm neonatal electroencephalogram (EEG). Models based on organoids disclosed herein are suitable for investigating the physiological basis of network formation at early and late stages of the human brain development. The absence of spinning bioreactors, for instance, means that virtually any laboratory working with stem cells would be able to successfully generate thousands of cortical organoids, and this procedure would be efficient and at a low cost. Limiting the time of exposure to growth factors during neuronal maturation is especially advantageous when studying neurological disorders, since specific growth factors are able to rescue disease phenotypes. Needless to say, the ability to model the complex functional dynamics of the human brain for research and therapeutic purposes is paramount. The disclosure demonstrates that human neurons in vitro are able to generate neural activity comparable to in vivo human electrophysiology. Moreover, as further shown in the ZIKV studies presented herein, the cortical organoids can be used in integrated models to study developmental treatments for brain tumors. These cortical organoid integrated models do not suffer from any the limitations seen with other brain cancer models (e.g., immune rejection), and can additionally be used in high-throughput put studies which are clearly not possible with other brain cancer models.

Pluripotent stem cells are a type of cell that undergoes self-renewal while maintaining an ability to give rise to all three-germ layer-derived tissues and germ cell lineages. Although pluripotent human embryonic stem (hES) cells derived from human blastocysts are promising sources for cell-based therapies to treat diseases and disorders such as Parkinson's disease, cardiac infarction, spinal cord injury, and diabetes mellitus, their clinical potentials have been hampered by their immunogenicity and ethical concerns.

Induced pluripotent stem cells are described by Shinya Yamanaka's team at Kyoto University, Japan. Yamanaka had identified genes that are particularly active in embryonic stem cells and used retroviruses to transfect mouse fibroblasts with a selection of those genes. Eventually, four key pluripotency genes essential for the production of pluripotent stem cells were isolated: Oct-¾, SOX2, c-Myc, and Klf4. The same group published a study along with two other independent research groups from Harvard, MIT, and the University of California, Los Angeles, showing successful reprogramming of mouse fibroblasts into iPS and even producing a viable chimera. The methods of obtaining iPS cells are known and described in the literature (see, U.S. Pat. No. 9,005,966 and U.S. Pat. Publ. No. 2015/0159143A1, the disclosure of which are incorporated herein by reference). Briefly, terminally differentiated human fibroblast (e.g., human dermal fibroblasts) cells can be induced to de-differentiate. The disclosure contemplates the use of a variety of de-differentiation agents comprising KLF4, OCT4, SOX2, c-MYC or n-MYC, NANOG or any combination thereof (e.g., KLF4, OCT4, SOX2, c-MYC or n-MYC and optionally NANOG). Such de-differentiation agents include nucleic acids, peptides, polypeptides, small organic molecules, and antibodies that cause induction of any one or more of KLF4, OCT4, SOX2, c-MYC or n-MYC and NANOG. De-differentiation may be achieved by contacting a cell in vitro with one or more de-differentiation factors for a time sufficient to induce de-differentiation. In one aspect, the de-differentiation factors are transfected into a cell to be de-differentiated under the control of a constitutive or inducible promoter or as RNA replicons comprising multicistronic RNA molecule separated by cleavable peptides (e.g., 2A peptides and/or IRES domains).

Cell types that can be that can be used in the methods and organoids of the disclosure include stem cells derived from any mammalian species including humans, monkeys, and apes and include embryonic stem cells, embryonic germ cells, and iPS cells (see, e.g., Nature, 448:313-318, July 2007: and Takahashi et al., Cell, 131 (5): 861-872; which are incorporated herein by reference). Stem cells can be induced to differentiate down a desired lineage using a number of techniques known in the art including, but not limited to, physical stimuli, chemical/biological factor stimuli (e.g., growth factors, media conditions), co-culturing techniques and any combination of the foregoing.

The disclosure provides a method of generating cerebral organoids and uses thereof, such as screening various therapeutics, modulating developmental activity and screening and analyzing disease states. The method of the disclosure includes a number of steps including (i) inducing neural progenitor cells development from stem cells, (ii) expanding/proliferating the neuronal progenitor cells, (iii) inducing neural cell differentiation and (iv) stimulating neural cell maturation. For example, a general method includes neural induction of single-cell suspensions of feeder-free iPS cells through the inhibition of the bone morphogenetic protein (BMP) and transforming growth factor-β (TGF-β) pathways. During the stage of progenitor cell proliferation, developing cortical organoids were exposed to fibroblast and epidermal growth factors (FGF2 and EGF, respectively). The FGF2 and EGF were replaced by brain-derived neurotrophic factor (BDNF), glial cell-derived neurotrophic factor (GDNF) and neurotrophic factor 3 (NT3), in addition to ascorbic acid and dibutyryl-CAMP, to promote and accelerate neuronal differentiation. Maturation was completed in medium without the addition of growth factors. During this process, the newly formed cortical organoids grew in a robust and consistent manner.

As mentioned above, sources of stem cells useful in the disclosure are known and include induced pluripotent stem cells (iPSCs). Of particular advantage is that iPSCs can be obtained from subject with various neurological diseases and disorders cause by genetic abnormalities. Thus, iPSCs induced from cells from such subjects will contain the genetic abnormality. Moreover, cerebral organoids derived from such cells will include the abnormality. Such "abnormal" cerebral organoids can then be used to study the disease and screen for treatments. Additionally, iPSCs from normal patient can be gene edited to provide for "abnormal" cerebral organoids that can also be used to study and screen for treatments for neurological diseases, disorders or conditions. Examples of techniques for gene editing include, but are not limited to, gene therapy, meganuclease-based engineering, zinc finger nuclease-based engineering. TALEN, and CRISPR-Cas systems or the like.

The somatic cells used to obtain induced pluripotent stem cells can be isolated from any number of various tissues of the body. For example, cells may be obtained from bone marrow; fetal tissue (e.g., fetal liver tissue), peripheral blood, umbilical cord blood, pancreas, skin and the like. In one embodiment, the cells are fibroblasts and in a further embodiment, the cells are obtained from a subject having, or suspected of having, a mutation that causes a neurological disease or disorder. As is well known a somatic cell includes the genetic makeup of the individual and thus any induced pluripotent stem cell obtained from the somatic cell will include the same genetic makeup (e.g., same mutations found in the somatic cells obtained from the subject).

The methods of the disclosure may be applied to a procedure wherein differentiated (lineage committed) cells are removed from a subject, de-differentiated in culture, manipulated to re-differentiate along a specific differentiation pathway (e.g., neuronal cells) and then cultured and studied to (a) determine a mutations phenotypic result and/or (b) screen agents for their effect on the mutant dedifferentiated neuronal cell.

For example, fibroblasts can be removed from a subject, de-differentiated using de-differentiation factors (e.g., with a KLF4, OCT4, SOX2, c-MYC or n-MYC, NANOG agonists or any combination thereof) and optionally mitotically expanded and then differentiated with factors (including physical stimuli) known to cause differentiation of iPSCs down a lineage committed path. In one embodiment, the method comprises removing differentiated cells from an injured or diseased subject. Cells de-differentiated from cells harvested from a subject can then be studied to determine a suitable therapy and/or screened to identify drug/biological candidates of interest to treat the disease or disorder. In one embodiment, the "de-differentiated cells" are differentiated down a lineage committed path to study a particular disease. For example, the de-differentiated cells (e.g., iPSC) can be differentiated down a neuronal lineage to obtain cortical organoids.

The isolation of cells, such as fibroblasts, from a subject are known. For example, the isolation of fibroblasts may, for example, be carried out as follows: fresh tissue, e.g., a biopsy, samples are thoroughly washed and minced in Hanks balanced salt solution (HBSS) in order to remove serum. The minced tissue is incubated from 1-12 hours in a freshly prepared solution of a dissociating enzyme such as trypsin. After such incubation, the dissociated cells are suspended, pelleted by centrifugation and plated onto culture dishes. Fibroblasts cells will attach to the culture dish before other cells, therefore, appropriate stromal cells can be selectively isolated and grown.

Somatic cell (e.g., a population of somatic cells such as fibroblasts) are obtained from a subject are de-differentiated into induced pluripotent stem cells (iPSCs). For mutations having effects on neuronal processing and development, the iPSCs are then differentiated to neuronal cells (e.g., such as into cortical organoids). Because the genome of the iPSCs will carry any mutant gene present in the somatic cell, the differentiated neuronal cells will also carry the same mutation. In this way, the effect of the mutation on neuronal function can be studied. In addition, various factors or agents can be used to modulate the effect of the mutation on neuronal cell function, which may further be specific for the subject that was the source of the cells. In other words, the differentiated neuronal cells can be used to screen agents for effects on the biological function of the mutant neuronal cells. In this way, agents that show a beneficial effect on a particular mutation can then be advanced as potential therapeutics.

IPSCs can be cultured and expanded using number of known methods. In some embodiments the cells are cultured in a feeder free system. In yet another embodiment, the stem cells are culture in a feeder free animal free culture system (see, U.S. Pat. No. 8,609,417, which is incorporated herein by reference). The cultured stem cells (e.g., iPSCs) can be stored (i.e., "banked") using commonly known techniques.

For example, feeder-free iPSCs can be fed daily with mTeSR™1 media (STEMCELL Technologies, Seattle, WA. U.S.A.).

In one embodiment, a pluripotent stem cell (e.g., an iPSC) is differentiated into a neural progenitor cell (NPC) using one or more factors (e.g., a SMAD inhibitor molecule). Exemplary embodiments include differentiating iPSC in the presence of SB431542. Alternative factors (individually and/or in combination) could be used in the disclosed methods. Though these factors are sometimes referred to as "dual" SMAD inhibitors, more or fewer than two factors may be utilized within the scope of these methods. Other SMAD inhibitors are known such as, but not limited to, dorsomorphin.

To induce neuronal-like stem cells, colonies of iPSCs are dissociated with Accutase (Life Technologies, Carlsbad, CA, U.S.A.) in PBS (1:1) and resuspended in mTeSR™1 media supplemented with SB431542 and dosomorphin and cultured in the presence of a Rho kinase (ROCK) inhibitor under rotation and/or conditions to form free-floating spheres (sometimes referred to "neurospheres"). Exemplary ROCK inhibitors include Y-27632 (Calbiochem, Sigma-Aldrich, St. Louis, MO, U.S.A.) and fasudil, which bind to the kinase domain to inhibit its enzymatic activity in an ATP-competitive mechanism. Negative regulators of ROCK activation include small GTP-binding proteins such as Gem, RhoE, and Rad, which can attenuate ROCK activity. H-1152 dihydrochloride (H-1152P-2HCl; (S)-(+)-2-Methyl-1-[(4-methyl-5-isoquinolinyl)sulfonyl] homopiperazine) can also be used. Additional ROCK inhibitors include those described in International Application Publication Nos.: WO 01/56988; WO 02/100833; WO 03/059913; WO 02/076976; WO 04/029045; WO 03/064397; WO 04/039796; WO 05/003101; WO 02/085909; WO 03/082808; WO 03/080610; WO 04/112719; WO 03/062225; and WO 03/062227, for example. In some of these cases, motifs in the inhibitors include an indazole core; a 2-aminopyridine/pyrimidine core: a 9-deazaguanine derivative; benzamide-comprising; aminofurazan-comprising: and/or a combination thereof. For example. WO 03/080610 relates to imidazopyridine derivatives as kinase inhibitors, such as ROCK inhibitors, and methods for inhibiting the effects of ROCK1 and/or ROCK2. The disclosures of the applications cited above are incorporated herein by reference.

After neurosphere formation, mTeSR media is replaced with Neurobasal (Life Technologies) supplemented with GlutaMAX™ (ThermoFisher Scientific), Gem21 NeuroPlex™ (Gemini Bio-Products, West Sacramento, CA. U.S.A.), N2 NeuroPlex™ (Gemini Bio-Products), MEM nonessential amino acids (NEAA; Life Technologies), antibiotics (e.g., Pen/Strep), SB431542 and dorsomorphin and cultured for about 5-10 days (typically about 7 days). The cells are then maintained in Neurobasal (Life Technologies) supplemented with GlutaMAX™, Gem21 NeuroPlex™ (Gemini Bio-Products, West Sacramento, CA, U.S.A.), MEM nonessential amino acids (NEAA; Life Technologies), antibiotics, and FGF2 for 5-10 days (typically about 7 days) to induce neuro-progenitor cell proliferation. This is followed by an additional 5-10 days (e.g., about 7 days) in Neurobasal (Life Technologies) supplemented with GlutaMAX™, Gem21 NeuroPlex™ (Gemini Bio-Products, West Sacramento, CA, U.S.A.), MEM nonessential amino acids (NEAA; Life Technologies), antibiotics. FGF2 and EGF (PeproTech, Rocky Hill, NJ, U.S.A.).

Following induction and proliferation of neuronal-progenitor cells, the cells are switch to media that promoted differentiation to cortical organoids. In one embodiment, the cells are cultured in media containing BDNF, GDNF and NT-3. For example, the cells are cultured with Neurobasal media (Life Technologies) supplemented with GlutaMAX™. Gem21 NeuroPlex™ (Gemini Bio-Products, West Sacramento, CA, U.S.A.), MEM nonessential amino acids (NEAA; Life Technologies), antibiotics BDNF, GDNF, NT-3 (all from PeproTech), L-ascorbic acid and dibutyryl-cAMP. Following organoid development, the organoids can be maintained in Neurobasal (Life Technologies) supplemented with GlutaMAX™, Gem21 NeuroPlex™ (Gemini Bio-Products, West Sacramento, CA, U.S.A.), MEM nonessential amino acids (NEAA; Life Technologies) and antibiotics, with media change ever 3-4 days.

For example, in the exemplary experiments described herein neural induction of single-cell suspensions of feeder-free iPS cells was achieved by the inhibition of the bone morphogenetic protein (BMP) and transforming growth factor-β (TGF-β) pathways. During progenitor cell proliferation, developing cortical organoids were exposed to fibroblast and epidermal growth factors (FGF2 and EGF, respectively). Next, FGF2 and EGF were replaced by brain-derived neurotrophic factor (BDNF), glial cell-derived neurotrophic factor (GDNF) and neurotrophic factor 3 (NT3), in addition to ascorbic acid and dibutyryl-cAMP, to promote and accelerate neuronal differentiation. Further maturation was completed in neural medium without the addition of growth factors. During this process, the newly formed cortical organoids grew in a robust and consistent manner (e.g., see FIG. 1C-F and Table 1).

While the functional difference between the organoids and a full neonatal cortex is notable, the current results represent the first step towards an in vitro model that captures the complex spatiotemporal oscillatory dynamics of the human brain. Robust extracellular electrical activity was established at earlier stages and progressively developed into an organized oscillatory network similar to that observed in human EEG. As such, it was shown that features of early functional network dynamics (e.g., spontaneous activity transients) can be recapitulated by an in vitro model of the developing cortex, with no additional constraints other than structural and genetic similarities. Organoid activity shows delta-high gamma phase-amplitude coupling during network-synchronous events, a hallmark of inter-regional cortical communication. Further, a differential role of glutamate and GABA in initiating and maintaining functional oscillatory network activity of the cortical organoids was shown herein. Additionally, the disappearance of oscillatory activity in developmental impaired organoids (MECP2-KO organoids) was also shown herein. Organoid network electrophysiological signatures spontaneously mimic human preterm neonatal EEG features between 28 and 38 post-conception weeks. This offers strong evidence for a convergent experience-independent neurodevelopmental program prior to birth. Given the potential roles of synchronized and oscillatory network dynamics in coordinating information flow between developed cortical brain regions during human cognition, these results highlight the potential for cortical organoids to advance our understanding of functional electrophysiology, brain development, and neuro-genetic disorders. The cortical organoids presented herein offer an innovative link between microscale organoid physiology and cognitive neuroscience.

It should also be noted that the iPSCs and NPC and organoids obtained herein can be cultured, expanded and used as cell banks or tissue banks. For example, once human induced pluripotent stem cells, NPCs or organoids have been established in culture, as described herein, they may be maintained or stored in cell or tissue "banks" comprising either continuous in vitro cultures of cells or tissues (requiring regular transfer and passaging) or tissue or cells which have been cryopreserved.

Cryopreservation of stem cells, or functional cortical organoids of the disclosure, may be carried out according to known methods, such as those described in Doyle et al., (eds.), 1995, Cell & Tissue Culture: Laboratory Procedures, John Wiley & Sons, Chichester. For example, but not by way of limitation, cells or tissues may be suspended in a "freeze medium" such as, for example, culture medium further comprising 15-20% fetal bovine serum (FBS) and 10% dimethyl sulfoxide (DMSO), with or without 5-10% glycerol.

The functional cortical organoids of the disclosure can be used, for example, to screen in vitro for the efficacy and/or cytotoxicity of compounds, growth/regulatory factors, pharmaceutical compounds, and the like on the stem cells or a particular lineage of cells derived/differentiated from the stem cells, to elucidate the mechanism of certain diseases by determining changes in the biological activity. The functional cortical organoids disclosed herein can be used in a variety of applications. These include but are not limited to transplantation or implantation of a corticoid organoid disclosed herein in vivo; screening for neuroprotective agents, growth/regulatory factors, pharmaceutical compounds, etc., in vitro; elucidating the mechanism of certain diseases; studying the mechanism by which drugs and/or growth factors operate; diagnosing and monitoring cancer in a patient; gene therapy; and the production of biologically active products, to name but a few.

The functional cortical organoids disclosed herein may be used in vitro to screen a wide variety of compounds, such as cytotoxic compounds, growth/regulatory factors, pharmaceutical agents, etc. To this end, the functional cortical organoids disclosed herein are maintained in vitro and exposed to the compound to be tested. The activity of a neuroprotective agent can be measured, e.g., by its ability to prevent neurodegenerative damage to neurons of the cortical organoid. This may readily be assessed by vital staining techniques. The effect of growth/regulatory factors may be assessed by analyzing the cellular content of the cortical organoids, e.g., by total cell counts, by differential cell counts, or by increases/decreases in the size of the cortical organoids. This may be accomplished using standard cytological and/or histological techniques including the use of immunocytochemical techniques employing antibodies. It is envisaged that the functional cortical organoids of the disclosure can be used as 'test subjects' to study the effects of any number of drugs, agents, and therapies (e.g., radiation therapy). For example, drugs that exert a neuroprotective effect can be tested on the functional cortical organoids disclosed herein. Drugs that affect dopamine or acetylcholine levels, e.g., by increasing dopamine levels or decreasing the rate of acetylcholine degradation, could be tested with the functional cortical organoids of the disclosure. Accordingly, the functional cortical organoids of the disclosure are ideal 'test subjects' for testing the effects of therapies, experimental drug products, and the like for diseases, disorders, conditions or syndromes associated with neurological function and activity. Examples of such diseases, disorders, conditions or syndromes include, but are not limited to, brain tumors; memory disorders (e.g., Huntingdon's disease, Alzheimer's disease, vascular dementia, corticobasal degeneration, Creutzfeldt-Jakob disease, frontotemporal dementia. Lewy Body dementia, mild cognitive impairment, and progressive supranuclear palsy); movement disorders (e.g., multiple sclerosis, Parkinson's disease, ataxia, dystonia, essential tremor, multiple system atrophy, myoclonus, Rett Syndrome, secondary Parkinsonism, spasticity, tardive dyskinesia. Tourette syndrome, and Wilson's disease); stroke; headaches; epilepsy; brain aneurysms; amyotrophic lateral sclerosis (ALS); and sleep disorders (e.g., narcolepsy).

The functional cortical organoids of the disclosure can also be used as model systems to test whether an agent exerts a neuroprotective effect (e.g., minimize damage resulting from ischemic injury). Neuroprotection refers to the relative preservation of neuronal structure and/or function. In the case of an ongoing insult (a neurodegenerative insult) the relative preservation of neuronal integrity implies a reduction in the rate of neuronal loss over time, which can be expressed as a differential equation. It is a widely explored treatment option for many central nervous system (CNS) disorders including neurodegenerative diseases, stroke, traumatic brain injury, spinal cord injury, and acute management of neurotoxin consumption (i.e., methamphetamine overdoses). Neuroprotection aims to prevent or slow disease progression and secondary injuries by halting or at least slowing the loss of neurons. Despite differences in symptoms or injuries associated with CNS disorders, many of the mechanisms behind neurodegeneration are the same. Common mechanisms include increased levels in oxidative stress, mitochondrial dysfunction, excitotoxicity, inflammatory changes, iron accumulation, and protein aggregation. Of these mechanisms, neuroprotective treatments often target oxidative stress and excitotoxicity—both of which are highly associated with CNS disorders. Not only can oxidative stress and excitotoxicity trigger neuron cell death but when combined they have synergistic effects that cause even more degradation than on their own. Thus limiting excitotoxicity and oxidative stress is a very important aspect of neuroprotection. Common neuroprotective treatments include glutamate antagonists and antioxidants, which aim to limit excitotoxicity and oxidative stress respectively. Accordingly, it is envisaged that the functional cortical organoids disclosed herein can be ideal test subjects for the effectiveness of agents in preventing neurodegenerative damage.

As further shown herein, functional cortical organoids disclosed herein can be made which comprise cancerous tumors by culturing the cortical organoids with cancerous cells. Thus, progressive human brain tumor growth can be modeled using integration of cancerous cells with cerebral organoids disclosed herein. As such these cortical organoids may be used as model systems to test, for example, the efficacy of anti-tumor agents, chemotherapeutic agents, and anticancer agents. Examples of anti-tumor agents, chemotherapeutic agents, and anticancer agents that can be used with the functional cortical organoids disclosed herein, include but are not limited to, alkylating agents such as thiotepa and CYTOXAN® cyclosphosphamide; alkyl sulfonates such as busulfan, improsulfan and piposulfan: aziridines such as benzodopa, carboquone, meturedopa, and uredopa; ethylenimines and methylamelamines including altretamine, triethylenemelamine, trietylenephosphoramide, triethiylenethiophosphoramide and tiimethylolomelamine: acetogenins (e.g., bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin;

spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; vinca alkaloids; epipodophyllotoxins; antibiotics such as the enediyne antibiotics (e.g., calicheamicin, especially calicheamicin gammall and calicheamicin omegall; L-asparaginase; anthracenedione substituted urea; methyl hydrazine derivatives; dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN®; doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C. mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU): folic acid analogs such as denopterin, methotrexate, pteropterin, trimetrexate; purine analogs such as fludarabine, 6-mercaptopurine, thiamiprine, thioguanine: pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone: aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitiaerine; pentostatin; phenamet; pirarubicin; losoxantione; podophyllinic acid; 2-ethylhydrazide; procarbazine; PSK®; polysaccharide complex (JHS Natural Products, Eugene, Oreg.); razoxane; rhizoxin; sizofiran; spirogermanium; tenuazonic acid; triaziquone; 2,2 2"-trichlorotiiethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL®; paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® (docetaxel) (Rhone-Poulenc Rorer, Antony, France); chloranbucil; GEMZAR® (gemcitabine); 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DFMO); retinoids such as retinoic acid; capecitabine; leucovorin (LV); irenotecan; adrenocortical suppressant; adrenocorticosteroids; progestins; estrogens; androgens; gonadotropin-releasing hormone analogs; and pharmaceutically acceptable salts, acids or derivatives of any of the above.

The functional cortical organoids of the disclosure may be used as model systems for the study of physiologic or pathologic conditions. For example, in a specific embodiment of the invention, a cortical organoid of the disclosure may be used as a model to determine absorption rates of various substances by cortical tissue, or the toxicity of the substances on neural cells.

The functional cortical organoids of the disclosure may also be used in personalized medicine by generating cortical organoids using the methods of the disclosure using cells of a patient suspected of having a malignancy or disease (e.g., a neurodegenerative disease or disorder). The generation of such 'personalized' cortical organoids can then be used in vitro to screen therapeutic and/or pharmaceutical compounds in order to identify those that are most efficacious in treating the particular patient's disease or malignancy.

Depending upon the intended use for the functional cortical organoids disclosed herein, various specialized cells or biological agents may be cultured with the cortical organoids. It should be noted, that since there is no immune rejection, there is no requirement that the cells that are cultured with the cortical organoids be from a certain genetic background or be from a certain species. As shown in the examples, cortical organoids can be cultured with cancer cells, resulting in cortical organoids comprising cancerous tumors. It is envisaged herein, that additional specialized cells or biological agents can be used to model other disease or disorders, in particular neurodegenerative diseases and disorders, like Parkinson's disease and Alzheimer's disease. In such a case, commonly used in vivo or in vitro models for these diseases, can instead be performed with the functional cortical organoids disclosed herein, including the use of specific Parkinson's disease-related proteins or Alzheimer's disease-related proteins.

The functional cortical organoids disclosed herein may be used as test subjects, to determine the effects of introducing genes and gene products, or mutations thereof, into the cortical organoids. For example, using recombinant DNA techniques, a gene that expresses a product that is associated with disease or disorder can be placed under the control of a viral or tissue-specific promoter. The recombinant DNA construct containing the gene could be used to transform or transfect one or more cells of the cortical organoids. The cortical organoids which express the introduced gene or gene product can then be studied for disease or disorder progression or for the effectiveness of treatments against the particular disease or disorder. Additionally, gene editing techniques can be used to modify the genes and gene products made by the cortical organoids. For example, using CRISPR-Cas system one could transform the cortical organoids to model specific neurological diseases, like Alzheimer's and Parkinson's disease, by expressing proteins associated with said neurological disease. The introduction of genes and gene products, or mutations thereof, into the cortical organoids can happen at any stage of differentiation of the cortical organoids, e.g., the genes and gene products can be introduced into undifferentiated immature cortical organoids to very differentiated mature organoids, as is further taught herein For any of the methods disclosed herein the methods may be performed using high-throughput screening (HTS). For example, thousands of cortical organoids, including cortical organoids which comprise brain tumors, can be generated at the same time. HTS-amenable test systems that mimic the human tissue environment can be used to optimize preclinical selection of the most active molecules from a large pool of potential effectors, for example, against solid tumors. Indeed, it is recognized that 3-dimensional cell culture systems better reflect the in vivo behavior of most cell types. Analogous to the case with cellular assays, simple assays of total drug binding in individual cortical organoids in a multi-well format represent an easy system for screening drugs with different binding properties. Following drug uptake as a function of time in individual cortical organoids would allow kinetic analysis and perhaps even the extraction of effective diffusion coefficients. Analogous to the case with cellular assays, simple assays of total drug binding in individual cortical organoids in a multi-well format represent an easy system for screening drugs with different binding properties. Following drug uptake as a function of time in cortical organoids would allow kinetic analysis. In addition, it should be possible to develop simple staining methods for measuring the extent of necrosis in intact, individual cortical organoids, which would then provide an assay for drug effects on the viability of the inner-region of the cortical organoids. There are certainly other staining techniques available that could be applied to an imaging-based screening system for cortical organoids, such as measuring apoptosis, proliferation, and various metabolism markers.

The following examples are intended to illustrate but not limit the disclosure. While they are typical of those that might be used, other procedures known to those skilled in the art may alternatively be used.

EXAMPLES

Cell source. iPSC lines derived from control individuals have been previously characterized elsewhere. Human embryonic stem cell (ESC) and iPSC colonies were expanded on Matrigel-coated dishes (BD Biosciences, San Jose, CA, USA) with mTeSR1 medium (StemCell Technologies, Vancouver, Canada). The cells were routinely checked by karyotype and CNV arrays to avoid genomic alterations in the culture.

Teratoma formation. iPSC colonies were dissociated, re-suspended in PBS-Matrigel, and injected subcutaneously in NOD SCID mice. The tumor was dissected, fixed in and paraffin embedded after 8 weeks. Sections of 10 μm thickness were stained with hematoxylin and eosin and analyzed for the presence of the three germ layer tissues.

MECP2-KO cell line generation. MECP2-deficient cell lines were generated by inducing pluripotency in fibroblasts derived from a male patient. Additionally, H9 human ESC with the CRISPR/Cas9 genome-editing system were used to induce frameshift mutations in the MECP2 locus. This incorporation resulted in the creation of early stop codons rendering a non-functional MECP2 protein. Mutagenesis and off-targets were confirmed by exome sequencing techniques. The CRISPR-Cas protocol was as described in Thomas et al. (Cell Stem Cell (2017). Once the pluripotency state of the cellular models was confirmed, they were differentiated into 2D neuronal monolayer cultures and cortical organoids.

Tissue source. Human fetal brain tissue was obtained under a protocol approved by the Human Research Protections Program Committee of the UCSD Institutional Review Board. All patients provided informed consent for collection and use of these tissues.

Generation of cortical organoids. Feeder-free iPSCs were fed daily with mTeSR1 for 7 days. Colonies were dissociated using Accutase (Life Technologies, Carlsbad, CA, USA) in PBS (1:1) for 10-20 minutes at 37° C., and centrifuged for 3 minutes at 100×g. The cell pellet was re-suspended in mTeSR1 supplemented with 10 μM SB431542 (SB; Stemgent, Cambridge, MA, USA) and 1 μM Dorsomorphin (Dorso; R&D Systems, Minneapolis, MN, USA). Approximately $4\times10^6$ cells were transferred to one well of a 6-well plate and kept in suspension under rotation (95 rpm) in the presence of 5 μM ROCK inhibitor (Y-27632; Calbiochem, Sigma-Aldrich, St. Louis, MO, USA) for 24 hours to form free-floating spheres. After 2 or 3 days, mTeSR was substituted by Medial [Neurobasal (Life Technologies) supplemented with GlutaMAX™. 2% Gem21 NeuroPlex™ (Gemini Bio-Products, West Sacramento, CA, USA). 1% N2 NeuroPlex™ (Gemini Bio-Products), 1% MEM nonessential aminoacids (NEAA; Life Technologies). 1% penicillin/streptomycin (PS: Life Technologies). 10 μM SB and 1 μM Dorso] for 7 days. Then, the cells were maintained in Media2 [Neurobasal with GlutaMAX™. 2% Gem21 NeuroPlex™, 1% NEAA and 1% PS] supplemented with 20 ng/ml FGF2 (Life Technologies) for 7 days, followed by 7 additional days in Media2 supplemented with 20 ng/ml of FGF2 and 20 ng/ml EGF (PeproTech, Rocky Hill, NJ, USA). Next, cells were transferred to Media3 [Media2 supplemented with 10 μg/mL of BDNF, 10 μg/mL of GDNF, 10 μg/mL of NT-3 (all from PeproTech), 200 μM L-ascorbic acid and 1 mM dibutyryl-cAMP (Sigma-Aldrich)]. After 7 days, cortical organoids were maintained in Media2 for as long as needed, with media changes every 3-4 days.

Mycoplasma testing. All cellular cultures were routinely tested for mycoplasma by PCR. Media supernatants (with no antibiotics) were collected, centrifuged, and resuspended in TE buffer. Only negative samples were used in the study.

Immunofluorescence staining. Cortical organoids were fixed with 4% paraformaldehyde overnight at 4° C., and then transferred to 30% sucrose. After the 3D structures sink, they were embedded in O.C.T. (Sakura, Tokyo, Japan) and sliced in a cryostat (20 μm slices). Following air drying, the slides containing the sliced samples were permeabilized/blocked with 0.1% triton X-100 and 3% FBS in PBS for 2 hours at room temperature, and incubated with primary antibodies overnight at 4° C. Primary antibodies that were used: mouse anti-Nestin, Abcam (Cambridge, UK) ab22035, 1:250; rat anti-CTIP2, Abcam ab18465, 1:500; rabbit anti-SATB2, Abcam ab34735, 1:200; chicken anti-MAP2, Abcam ab5392, 1:2000; rabbit anti-Synapsin1, EMD-Millipore AB1543P, 1:500; mouse anti-NeuN, EMD Millipore MAB377, 1:500; rabbit anti-Ki67, Abcam ab15580, 1:1000; rabbit anti-SOX2, Cell Signaling Technology 2748, 1:500; rabbit anti-GFAP, DAKO Z033429, 1:1000; rabbit anti-TBR1, Abcam ab31940, 1:500; rabbit anti-TBR2, Abcam ab23345, 1:500; rabbit anti-beta-catenin. Abcam E247, 1:200); mouse anti-GABA. Abcam ab86186, 1:200; rabbit anti-PROX1, Abcam ab101651, 1:250. Next, the slices were washed with PBS and incubated with secondary antibodies (Alexa Fluor 488-, 555- and 647-conjugated antibodies. Life Technologies. 1:1000) for 2 hours at room temperature. The nuclei were stained using DAPI solution (1 μg/mL). The slides were mounted using ProLong Gold antifade reagent and analyzed under a fluorescence microscope (Z1 Axio Observer Apotome, Zeiss).

Synaptic puncta quantification. Pre-synaptic Syn1+puncta were quantified after 3D reconstruction of z-stacks of random images from randomly selected regions of all lines and from two independent experiments. Only puncta overlapping MAP2-positive processes were scored.

Immuno-gold electron microscopy (EM). Immuno-gold EM was performed at the CMM Electron Microscopy Facility at University of California San Diego. Four-month-old organoids were fixed using 4% paraformaldehyde in 0.1 M phosphate buffer (pH 7.4). Fixed cells were pelleted and washed with 0.15 M glycine/phosphate buffer, embedded in 10% gelatin/phosphate buffer and infused with 2.3 M sucrose/phosphate buffer. Blocks of cells with 1 $mm^3$ were mounted onto specimen holders and snap frozen in liquid nitrogen. Ultracryomicrotomy was carried out at −100° C. on a Leica Ultracut UCT with EM FCS cryoattachment (Leica, Bannockburn, IL) using a Diatome diamond knife (Diatome US, Hatfield, PA). 80 to 90 nm frozen sections were picked up with a 1:1 mixture of 2.3 M sucrose and 2% methyl cellulose (15 cp) and transferred onto Formvar and carbon-coated copper grids. Briefly, grids were placed on 2% gelatin at 37° C. for 20 min. rinsed with 0.15 M glycine/PBS and the sections were blocked using 1% cold water fish-skin gelatin. Grids were analyzed using a Tecnai G2 Spirit BioTWIN transmission electron microscope equipped with an Eagle 4k HS digital camera (FEI, Hilsboro, OR).

Targeted single cell qRT-PCR and analysis. Specific target amplification was performed in individual dissociated cortical organoids using C1 Single-Cell and BioMark HD Systems (Fluidigm, San Francisco, CA, USA), according to the manufacturer's and as described in Chailangkarn, T. et al., Nature 536, 338-343 (2016). Briefly, cortical organoids were mechanically dissociated after 30 minutes of incubation in Accumax (Innovative Cell Technologies, San Diego, CA. USA)) at 37° C. under rotation. After passing through 100-μm and 40-μm strainers, cells were centrifuged and resuspended in Media2 (as described above). Single cortical cells were captured on a C1 medium chip and cell viability was assessed using a LIVE/DEAD Cell Viability/Cytotoxicity kit (Life Technologies). The targeted single-cell qPCR was performed using DELTAgene primer pairs in the 96.96 Dynamic Array IFC chip. The results were analyzed using Fluidigm Real-time PCR Analysis software and Singular Analysis Toolset 3.0 (Fluidigm).

10 X genomics single-cell and analysis. After organoid dissociation. single cells were processed through the Chromium Single Cell Gene Expression Solution using the Chromium Single Cell 3' Gel Bead. Chip and Library Kits v2 (10 X Genomics, Pleasanton) as per the manufacturer's protocol. In brief, single cells were resuspended into 0.1% BSA in PBS. Five thousand cells were added to each channel with an average recovery rate of 1.746 cells. The cells were then partitioned into Gel Beads in Emulsion in the Chromium instrument, where cell lysis and barcoded reverse transcription of RNA occurred, followed by amplification, shearing and 5' adaptor and sample index attachment. Libraries were sequenced on an Illumina HiSeq 2500. Demultiplexing, alignment to the hg19 transcriptome and unique molecular identifier (UMI)-collapsing were performed using the Cellranger toolkit (version 2.0.1) provided by 10 X Genomics. total of 3.491 cells with approximately 53.000 reads per cell were processed. Analysis of output digital gene expression matrices was performed using the Seurat R package. Matrices for replicates were merged with the MergeSeurat function and all genes that were not detected in at least 5% of all single cells were discarded, leaving 10.594 genes for further analyses. Cells with fewer than 600 or more than 8.000 expressed genes as well as cells with more than 50,000 UMIs or 0.1% mitochondrial expressed genes were removed from analysis. Data were log normalized and scaled to 10.000 transcripts per cell. Variable genes were identified with the FindVariableGenes function. Principal components were evaluated for statistically significant gene expression signals using the JackStraw function. PCA was carried out, and the top 36 principal components were retained. With these principal components, t-SNE was applied with the RunTSNE function to visualize the cells in two dimensions and identified distinct cell clusters with the FindClusters function with resolution=0.30. Differential expression to identify cluster markers was performed using the FindAllMarkers function.

Calcium imaging. 2D neuronal monolayer culture and 2-month-old intact cortical organoids and 2D neuronal monolayer were plated, washed with PBS and incubated with 5 μM Fluo-4AM (Life Technologies) in Media2 for 60 minutes. Five thousand frames were acquired at 28 Hz using a Hamamatsu ORCA-ER digital camera (Hamamatsu Photonics K.K., Japan) with a 488 nm filter on a Z1 Axio Observer Apotome (Zeiss, Oberkochen, Germany). Images from different neurons were processed and analyzed using individual circular regions of interest (neuronal soma) on Matlab 7.2 (Mathworks, Natick, MA), which comprehended neurons on the surface of the organoids. The amplitude of signals was presented as relative fluorescence changes (AF/F) after background subtraction. The threshold for calcium spikes was set at the $95^{th}$ percentile of the amplitude of all events. Average frequency across all regions of interest were used to data analysis.

Multi-electrode array (MEA). Six-week-old cortical organoids were plated per well in 12-well MEA plates (Axion Biosystems, Atlanta, GA, USA). Each well contains 64 platinum microelectrodes with 30 μm of diameter spaced by 200 μm, yielding a total of 512 channels. The plate was previously coated with 100 μg/mL poly-L-ornithine and 10 μg/ml laminin, and four independent experiments were performed in duplicates. Cells were fed twice a week and measurements were collected 24 hours after the medium was changed, once a week, starting at two weeks after plating (8 weeks of organoid differentiation). Recordings were performed using a Maestro MEA system and AxIS software (Axion Biosystems) with a customized script for high band-pass filter (0.1-Hz and 5-KHz cutoff frequencies). Spikes were detected with AxIS software using an adaptive threshold set to 5.5 times the standard deviation of the estimated noise for each electrode (channel). The plate was first allowed to rest for three minutes in the Maestro device, and then four minutes of data were recorded. For the MEA analysis, the electrodes that detected at least 5 spikes/min were classified as active electrodes using Axion Biosystems' Neural Metrics Tool. Bursts were identified in the data recorded from each individual electrode using an inter-spike interval (ISI) threshold requiring a minimum number of 5 spikes with a maximum ISI of 100 ms. A minimum of 10 spikes under the same ISI with a minimum of 25% active electrodes were required for network bursts in the well. The synchrony index was calculated using a cross-correlogram synchrony window of 20 ms. Bright-field images were captured from each well to assess for neural density and electrode coverage over time.

Custom MEA analysis. Raw MEA recordings were converted to .mat files using Axion-provided functions and analyzed offline using custom MATLAB functions and scripts. Local field potential signals (LFP) from each of the 64 electrodes were generated by low-pass filtering (FIR filter) and downsampling raw signals from 12.500 Hz to 1.000 Hz (resample.m). Spikes were detected as follows: each channel was first referenced to the well median (64 channels). The median was used instead of the mean to avoid biasing the reference during high firing rate periods. Next, the re-referenced signal was bandpass filtered for 300-3,000 Hz with a 3rd-order Butterworth filter (butter.m). The spike threshold was set to be 5.5 standard deviations, where the standard deviation was estimated as previously described in Quiroga et al. Neural Comput. 16, 1661-87 (2004) to avoid biasing the threshold for channels with high firing rates (thus an artificially high threshold; see FIG. 6A for example spikes). Spike timestamps were taken as the peak time after the absolute value of the signal crossed the threshold, but at least 1 ms from another spike (findpeaks.m). Spike timestamps were then converted into binary vectors (1 ms bin size), summed across 64 channels, and smoothed (conv.m) with a normalized 100-point Gaussian window (gausswin.m) to create a population spiking vector for each MEA well. Note that spikes from each channel do not represent single-unit spikes as the spatial resolution of MEA electrodes were too sparse. Multi-unit spiking were not sorted since total population spiking (of well) was submitted for further analysis, rather than individual spike trains.

Figures 7B, 7C, 7D:
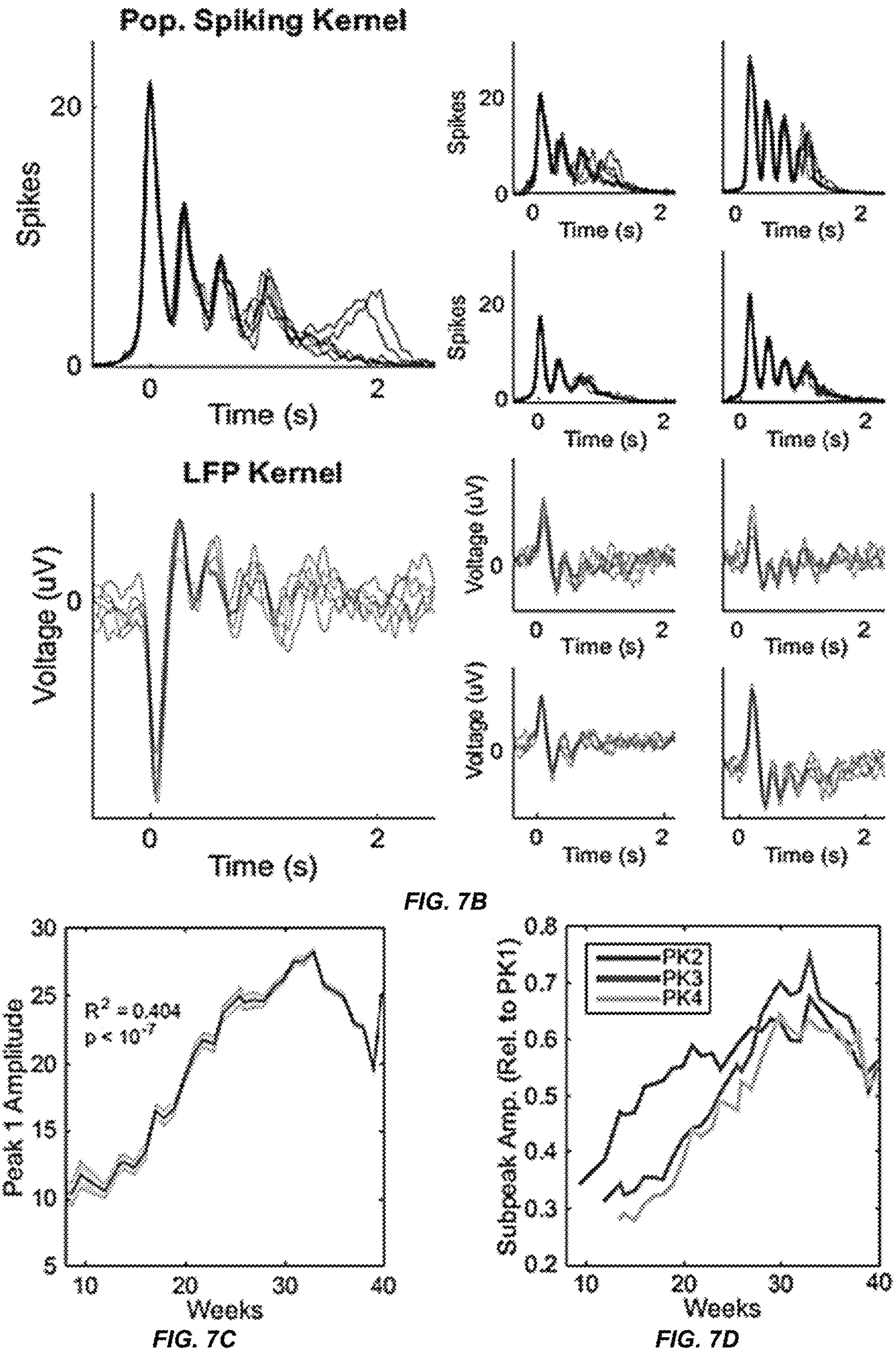
Figures 7E, 7F, 7G, 7H, 7I, 7J:
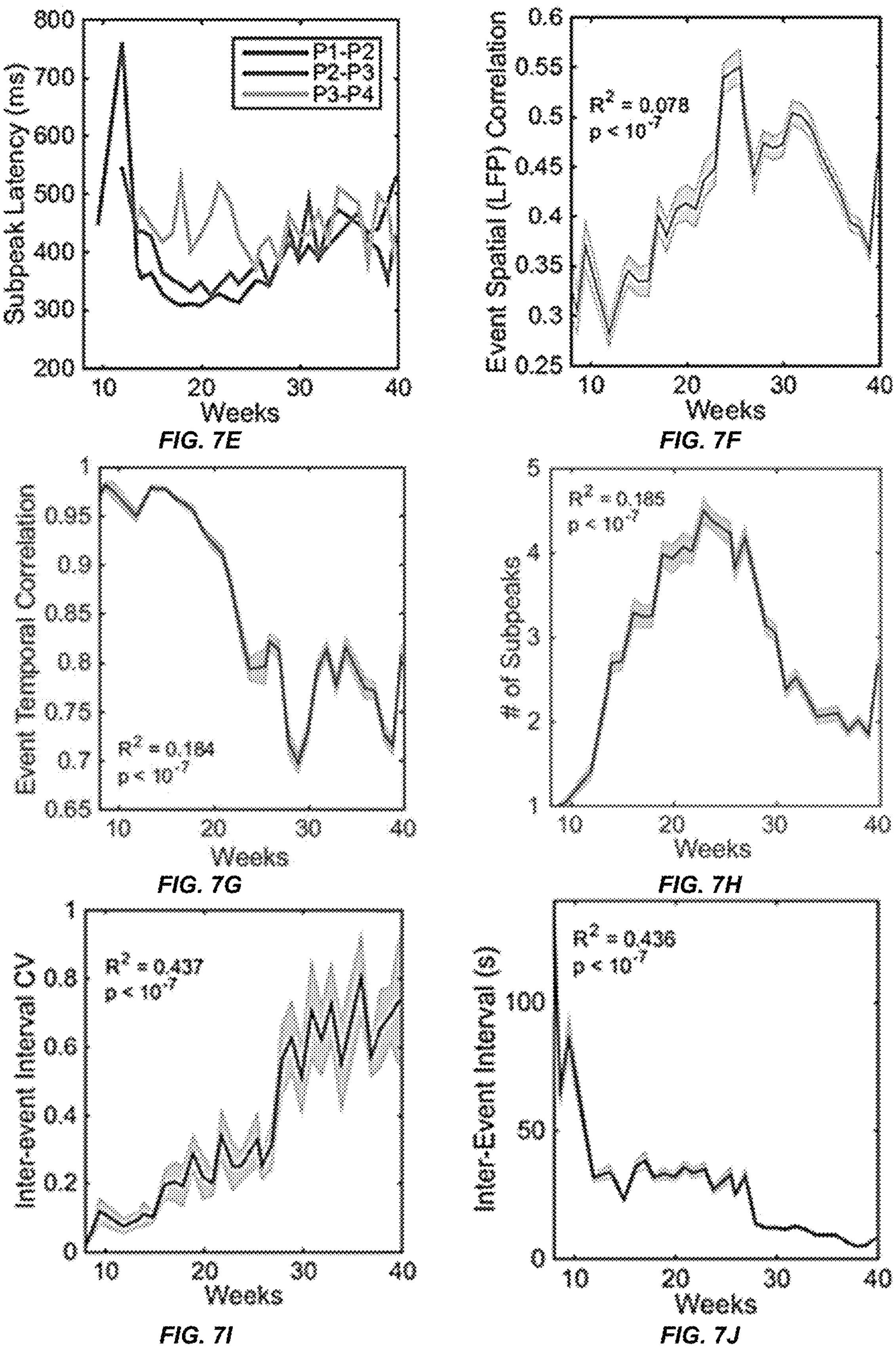

Network event analysis. A network event was detected when population spiking was (i) greater than 80% of the maximum spiking value over the length of the recording, (ii) at least 1 spike/s, and (iii) 1 second away from any other network events. The first peak after all 3 criteria were satisfied was marked as t=0, and the window of data, from 0.5 s before to 2.5 s after the peak was collected as the network event. LFP data from all 64 channels from the same timeframe were also collected for analysis. All events from different MEA wells obtained on the same recording day were aggregated for statistical analysis and plotting, as shown in FIGS. 4 and 7 (with the exception of FIG. 7I). Subpeaks within an event were identified using findpeaks.m, where a subpeak must satisfy the following: (i) peak height of at least 25% of the first peak, (ii) peak width of at least 50 ms, (iii) at least 200 ms away from the previous peak, and (iv) peak prominence of 1 over Peak 1 height. Subpeak time and the height relative to the initial peak were recorded. The inter-event interval coefficient of variation (IEI CV) (e.g., see FIG. 7I) was calculated as the standard deviation of the inter-event interval divided by its mean, where IEI is the time between consecutive network events within the same MEA well. Event temporal correlation was calculated as the mean Pearson correlation coefficient of population spiking vector during each network event with every other network event in the same MEA well across a single recording session. Event spatial correlation was calculated as the mean Pearson correlation coefficient between all pairs of 64 LFP channels during each 3-s network event.

Oscillatory spectral power analysis. Power spectral density (PSD) estimates were computed using Welch's method (pwelch.m), with a window length of 2 s and overlap of 1 s. Oscillatory power was defined as peaks in the PSD above the aperiodic $1/f$ power law decay. Thus, for each channel, a straight line was fit over the PSD in double-log space between 0.5-20 Hz using robust fit (robustfit.m), and oscillatory power was computed as the difference between the mean log PSD power and the mean log fitted power (baseline), over 2.5-4.5 Hz.

Regression models. For analysis in FIGS. 4H and I and FIGS. 7C, F, and G. simple regression models (LinearModel.fit,MALAB) was fit using organoid age (in days) as input and electrophysiological features as output. Order-1 (linear) models were fit for FIG. 4I and FIGS. 7C, G and I, and order-2 (quadratic) models were fit for FIG. 4H, FIGS. 7F and H and FIG. 9C. Reported $R^2$ and p values are model statistics over the entire dataset. With the exception of FIG. 7I, all events from different MEA wells on the same recording day were aggregated as samples drawn from the same distribution. To predict culture age, 3 electrophysiological features were used as input—event latency, event peak spiking, and oscillatory power—and their square roots to account for the nonlinear inverted-U features. These were used to build a regression model. Within-well models were fit over all data points of the same well, and goodness-of-fit was reported as the model $R^2$ and the RMSE. Across-well models were trained and evaluated using leave-1-out cross-validation, and goodness-of-fit is reported as the $R^2$ and the RMSE computed over the validation set, not the training set.

Phase Amplitude Coupling (PAC). LFP data from all 64 channels of each well was first lowpass/bandpass filtered (eegfilt.m. EEGLAB) for delta (0-4 Hz) and high-frequency, broadband gamma (200-400 Hz) activity. Delta phase was extracted by taking the phase angle of the bandpassed delta signal Hilbert transform (hilbert.m, angle.m), while gamma power was extracted by taking the squared magnitude of the filtered gamma. Gamma power was smoothed with the same delta-band filter for display purposes, but not for subsequent analysis. To compute PAC, instantaneous delta phase was binned into 20 equidistant bins between $-\pi$ and $\pi$, and gamma power was sorted based on the corresponding delta phase at the same sample time and averaged across the same phase bin. This procedure was performed separately for event and non-event indices, where event indices are the same 3-s windows as described above in Network Event Analysis. Well-average gamma was calculated by aligning the binned gamma vector for each channel such that the phase of maximum gamma power was $-\pi$ and was averaged across all 64 channels. The resultant well-averaged gamma power was normalized and PAC was calculated as the Kullback-Leibler divergence between the distribution of gamma power across phase bins and a uniform distribution (also known as Modulation Index).

Pharmacology. The pharmacological manipulation was performed using the following drugs: 10 μM bicuculline, 50 μM muscimol, 20 μM CNQX, 20 μM AP5, 25 μM baclofen and 1 μM TTX. In this assessment, baseline recordings were obtained immediately before and 15 min after the addition of the compound. Three washes with PBS for total removal of the drug were performed in washout experiments; fresh media was added and another recording was conducted after 2 hours.

Preterm neonatal EEG. The dataset includes 567 recordings from 39 preterm neonates (24-38 weeks old conception age), consisting of 23 EEG features computed from the entirety of each recording, as well as during "low-activity periods" (46 features in total), and the post-conception age in weeks.

Neonate-organoid age prediction model. To compare the developmental trajectory of cortical organoids and the preterm human brain, an Elastic Net (L1- and L2-regularized) regression model was trained on only the preterm neonatal EEG features and used that model (with all parameters held the same) to generate an equivalent organoid "brain-age" for each recording time point over 40 weeks in culture. Specifically, the training dataset consists of a subset of the preterm EEG data; of the 46 included features; all "low-activity-period" features were discarde since there was no equivalent period for organoid recordings, as well as features that could not sensibly compute from organoid LFPs, such as interhemispheric synchrony. This selection was done a priori, and 13 features remained, including 4 features for relative spectral power in distinct frequency bands, which were further discarded due to frequency-dependent filtering properties of the skull and difference in spatial integration of currents in macroscopic EEG electrodes compared to microscopic planar MEA electrodes. The remaining 9 features correspond to aspects of spontaneous activity transient (SAT) timing, such as SATs per hour and SAT duration, which were similarly computed on organoid LFPs after network event detection described earlier (see Table 3 for a full list of included and rejected features). This latter organoid LFP test dataset was never seen by the regression model until prediction time. Training was performed using scikit-learn linear model module (ElasticNetCV), with K-Group shuffle split cross-validation on regularization hyperparameters, where K=25% of groups, N=200 shuffles. In other words, the best regularized linear model possible for predicting the conception age of preterm neonates was found using those 9 precomputed EEG features. This model was directly applied on organoid LFP features to determine the corresponding "brain age" of the organoids during 40 weeks in culture. 1-sample t-tests were performed from every time point to test whether the mean predicted "brain age" was significantly different from the organoid culture age.

Resampled feature correlation. Pearson's correlation coefficient was computed between neonate age and each of the 9 EEG features, after a leave-K-groups-out resampling procedure N times, where K is the number of neonates from whom all recordings were left out in computing the correlation (50% of all neonates, resampling N=100). An identical procedure was performed to compute the correlation between organoid culture age and LFP features (K=4 out of 8, 50%, N=100). Mean and standard deviation were then computed over all resampled draws in order to compare between organoid LFP and neonatal EEG.

Statistical analysis for organoids. Data are presented as mean±s.e.m., unless otherwise indicated, and it was obtained from different samples. No statistical method was used to predetermine the sample size, and no adjustments were made for multiple comparisons. The statistical analyses were performed using Prism software (GraphPad, San Diego, CA, USA). Student's t-test, Mann-Whitney-test, or ANOVA with post hoc tests were used as indicated. Significance was defined as $P<0.05$(*), $P<0.01$(), or $P<0.001$ (*). Blinding was used for comparing affected and control samples.

Culture of glioblastoma stem cells, differentiated tumor cells, and nonmalignant brain cultures. Glioblastoma stem cell models and derivation of cultures were performed as reported Flavahan et al. *Nat Neurosci.* 16 (10): 1373-1382 (2013)) and Wang et al. *Nat Neurosci.* 2017. To prevent culture-induced drift in glioblastoma models, patient-derived subcutaneous xenografts were generated in NOD-scid IL2Rgnull mice (Jackson Laboratory) and maintained as a recurrent source of tumor cells for study. Upon venograft removal, a papain dissociation system (Worthington Biochemical) was used to dissociate tumors according to the manufacturer's instructions. Cells were then cultured in Neurobasal complete media (Neurobasal Medium; Life Technologies) supplemented with 1× B27 without vitamin A (Thermo Fisher), 2 mM l-glutamine (Thermo Fisher), 1 mM sodium pyruvate (Thermo Fisher), 10 ng/ml basic fibroblast growth factor (bFGF), and 10 ng/mL epidermal growth factor (EGF; R&D Systems). The GSC phenotype was validated by OLIG2 and SOX2 expression, functional assays of self-renewal (serial neurosphere passage), and tumor propagation using in vivo limiting dilution. All cells were incubated at 37° C.in humidified incubators supplemented with 5% $CO_2$ and tested to ensure that they were negative for mycoplasma.

Proliferation and sphere formation assay. Cell viability was measured using CellTiter-Glo (Promega) according to the manufacturer's instructions. All data were normalized to day 0, prior to infection with ZIKV, and expressed as a relative cell number. Neurosphere formation was measured as described in Flavahan et al. *Nat Neurosci.* 16 (10): 1373-1382 (2013)) and Wang et al. *Nat Neurosci.* 2017. Briefly, decreasing numbers of cells per well (50, 20, 10, 5, and 1) were plated into 96-well plates. Seven days after plating, the presence and number of neurospheres in each well were recorded. Extreme limiting dilution analysis was performed using software available at bioinf.wehi.edu au/software/elda.

Brightfield images. GFP-GSC, GSC and corticoid images were acquired on an EVOS cell imaging microscope (Thermo Fisher). Images were acquired using an ImageXpress Micro automated microscope (Molecular Devices) and exported using MetaXpress 5.3 (Molecular Devices).

ZIKV preparation. ZIKV human isolate H/PAN/2016/BEI-259634 (BEI Resources, NR-50210) from Panama and human isolate PRVABC59 (BEI Resources, NR-50240) from Puerto Rico were acquired from ATCC, distributed by BEI. Both were expanded on Vero cells to amplify titers, totaling 2-3 serial passages of the original viral stock. Infected cell supernatants were concentrated through a 30% sucrose cushion, and concentrated virus was re-suspended in neural maintenance medium base (50% DMEM/F12 GlutaMAX™. 50% Neurobasal medium, 1× N-2 Supplement, 1× B-27 Supplement (all from Life Technologies) supplemented with 1% DMSO and 5% FBS and stored at −80° C. Viral stock titers were determined by plaque assay on Vero cells and were greater or equal to $2\times10^8$ plaque forming units/mL. Mock medium was prepared by concentrating uninfected Vero cell supernatant as above.

ZIKV titration. Viral titers (plaque forming units (PFU)/mL) were calculated by plaque-forming assays on Vero cells. Vero cells were seeded at a density of $7.5\times10^4$ cells per well in standard 24-well plates and incubated at 5% $CO_2$, 37° C. for 48 hours before infection. Serial dilutions of supernatants collected from ZIKV-infected NPCs and GSCs after infection with ZIKV at MOI 0.01 were added to Vero cells for 1 hour. Cells were covered with an agarose overlay and further incubated for 72 hours. 4% formaldehyde was added on top of overlays for 24 hours to fix monolayers, overlays were removed, and cell monolayers were stained with crystal violet to visualize plaques.

In vitro viral infection. GSCs were plated at 5.000 cells/well in 96-well tissue culture treated plates (TPP) and allowed to attach overnight. For viral infection and growth inhibition assays. ZIKA-HPAN and ZIKA-PRV at a range of MOI 0.1, 1. and 5 FFU/cell.

Human induced pluripotent stem cells (iPSCs), NPCs and corticoid generation. Human iPSCs cell lines obtained from healthy patients were generated as described in Marchetto et al., *Cell.* 143 (4): 527-539 (2010) and Chailangkarn et al., *Nature.* 536(7616):338-343 (2016). by reprogramming fibroblasts from healthy donors. The iPSC colonies were plated on Matrigel-coated (BD Biosciences) plates and maintained in mTESR media (Stem Cell Technologies). hiPSC-derived NPCs were obtained and maintained as described Marchetto et al., *Cell.* 143 (4): 527-539 (2010) and Chailangkarn et al., *Nature.* 536 (7616): 338-343 (2016). The iPSCs lines maintained in mTSER media were switched to N2 media (DMEM/F12 media supplemented with 1× N2 NeuroPlex™ Serum-Free Supplement (Gemini)) supplemented with the dual SMAD inhibitors 1 μM of dorsomorphin (Tocris) and 10 μM of SB431542 (Stemgent) daily, for 48 hours. After two days, colonies were scraped off and cultured under agitation (95 rpm) as embryoid bodies (EB) for seven days using N2 media with dorsomorphin and SB431542. Media was changed every other day. EBs were then plated on Matrigel-coated dishes and maintained in DMEM/F12 supplemented with 0.5× of N2 supplement. 0.5× Gem21 NeuroPlex™ Serum-Free Supplement (Gemini), 20 ng/ml basic fibroblast growth factor (bFGF, LifeTechnologies) and 1% penicillin/streptomycin (P/S). After seven days in culture, rosettes arising from the plated EBs were manually picked, gently dissociated with StemPro Accutase (LifeTechnologies) and plated onto poly-L-ornithine (Sigma)/Laminin-coated (LifeTechnologies) plates. NPCs were maintained in DMEM/F12 with 0.5× N2, 0.5× Gem21, 20 ng/ml bFGF and 1% P/S. The medium was changed every other day. NPCs were split as soon as confluent using StemPro Accutase for 5 min at 37° C. centrifuged and replated with NGF with a 1:3 ratio in poly-L-ornithine/Laminin-coated plates.

Human iPSC-derived cortical organoids were obtained as described above, with minor modifications. Briefly, iPSC colonies were gently dissociated using Accutase in PBS (1:1) (Life Technologies). Cells were then transferred to 6-well plates and kept under suspension. For neural induction, media containing DMEM/F12. 15 mM HEPES. 1× GlutaMAX™. 1× N2 NeuroPlex™ (Gemini), 1× MEM-NEAA. 1 μM dorsomorphin (R&D Systems), 10 μM SB431542 (Stemgent) and 100 U/mL penicillin-streptomycin was used for six days. NPC proliferation was obtained in the presence of Neurobasal media supplemented with 2× Gem21 NeuroPlex™, 1× NEAA, 1× GlutaMAX™, 20 ng/ml EGF and 20 ng/ml bFGF. The cells were kept in the same media thereafter in the absence of growth factors for neuronal maturation.

GSC-corticoid formation. 100-100K 3565, 387 or 1517 GFP-labeled GSCs were added per brain corticoid and allowed to proliferate. GFP-labeled GSCs were present inside corticoids as early as 24 hours post-addition. The experiments were conducted 2-3 weeks after adding GSCs onto the corticoids. Neurobasal media supplemented with 1× GEM21 (Gemini), 1% NEAA (Life Technologies), 1% GlutaMAX™ (ThermoFisher Scientific) and 1% penicillin/streptomycin (Life Technologies) was used throughout the experiment.

GSC organoid formation. Between $1\times10^5$- and $2\times10^5$ of 3565, 387 or 1517 GSCs were put per well in a 24-well plate under constant agitation at 95 rpm at 37° C. in Neurobasal media supplemented with 1× X GEM21 (Gemini), 1% NEAA (Life Technologies), 1% GlutaMAX™ (ThermoFisher Scientific) and 1% penicillin/streptomycin (Life Technologies). The organoids started forming as early as 2 days after being put in suspension but were allowed to grow for 2-4 weeks before performing subsequent experiments were performed.

Organoid and corticoid in vitro ZIKV infection. GSC-corticoid and GSC organoids were infected with H/PAN/2016/BEI-259634, Panama 2016 and PRVABC59, Puerto Rico 2015 ZIKV strains for 2 hours at 37° C. at a MOI of 5 and then the media containing the virus was removed and fresh media was added (Neurobasal media supplemented with 1× GEM21 (Gemini), 1% NEAA (Life Technologies), 1% GlutaMAX™ (ThermoFisher Scientific) and 1% penicillin/streptomycin (Life Technologies)).

Anti-integrin αvβ5 antibody treatment of glioblastoma organoids. Two- to 4-week-old GSC organoids were incubated with 50 μg/mL of integrin αvβ5 antibody for 2-4 hours, then infected with PRVABC59 ZIKV strain for 2 hours at 37° C. at a MOI of 5. The media was then removed and fresh media containing 50 μg/mL of integrin αvβ5 antibody was added. The integrin αvβ5 antibody was added twice a week and GSC organoids were monitored for a month.

Image analysis. To calculate the integrated density of GFP in GSC-brain corticoids, Image J software was used. Briefly, the channels were split and the integrated density of the GFP channel was measured by the software.

ZIKV statistical analysis. All statistical analysis was performed using Prism 7.0 software (GraphPad). The number of animals and replicate experiments is specified in each figure legend. Sample size is similar to those reported in previous publications. All grouped data were presented as mean±SD or SEM as indicated in the figure legends. Student's t test. one-way ANOVA with Tukey multiple comparison correction, and two-way ANOVA with the Bonferroni multiple comparison test were used to assess the significance of differences between groups. These tests were performed when the sample size was large enough to assume that the means were normally distributed or that the distribution of residuals was normal. For groups being statistically compared, variances in data were similar. For animal survival analysis, Kaplan-Meier curves were generated and the log-rank test was performed to assess statistical significance between groups. Correlation between gene expression and patient survival was performed through analysis of The Cancer Genome Atlas (TCGA) and brain tumor datasets downloaded from the TCGA data portal or NCBI GEO database. Raw data from enhancer profiling of primary glioma tissues were deposited at GSE101148. ChIP-seq data were accessed from the NCBI GEO database at GSE54792 and GSE17312.

Figure 1A:
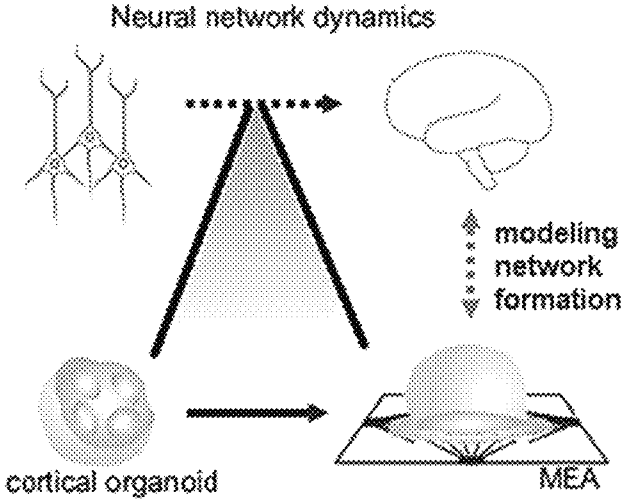
FIG. 1A-N provides for the cellular and molecular development of human cortical organoids. (A) Overview of human neural network formation and dynamics evaluation using organoids. (B) Schematic of the protocol used to generate cortical organoids. Scale bar, 200 μm. (C) Organoid growth during different developmental stages. (D) Cryosections at early differentiation stages. Cortical organoids are composed of small ventricular zone-like regions organized around the lumen with abundant proliferating NPCs. Scale bar, 50 μm. (E) At two months, the proliferative region is surrounded by intermediate progenitor cells ($TBR2^+$) and deep cortical layer markers ($TBR1^+$ and $CTIP2^+$). Cortical plate folding is observed in the organoids. (F-G), At later stages of maturation, a concentric multi-layer structure is observed in the organoid that includes superficial cortical neurons ($SATB2^+$). A radial-tangential neuronal migration pattern is established and the amount of glial cell increases. Scale bar, 50 μm. (H) Population analysis of specific markers indicating stages of maturation and multiple neuronal subtypes. The data are shown as mean±s.e.m. (n=8, 4 independent experiments). (I) Principal component analysis (PCA) of cells projected onto the first two components. Overlaid populations of 2- and 10-month-old cortical organoids are compared to 2-month-old 2D monolayer neurons. All timelines for this and the subsequent experiments consider the iPSC stage as day 0 (n=2 independent cell lines for each cortical culture; n=3 for 2D monolayer neurons). (J) Heatmap of average expression for representative gene markers by cluster and cell-type. (K-L) Violin plots illustrate the differences in single-cell expression of target genes in cortical organoids and 2D neurons. (M) Reproducibility of organoid size at 2 months of maturation (n=20 independent experiment, 7 different cell lines). (N) Violin plots showing transcript levels for representative markers of each cluster.
Figure 1B:
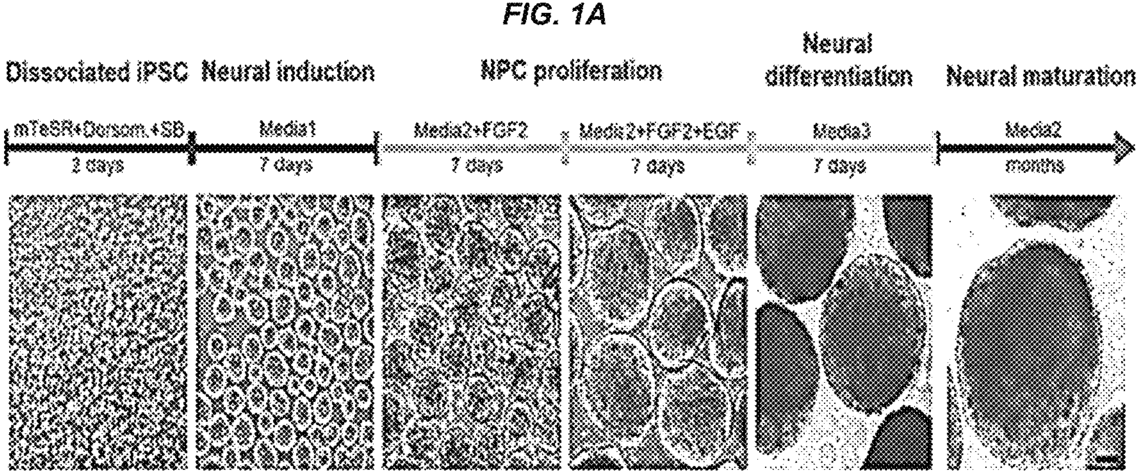
Figures 1C, 1D, 1E, 1F:
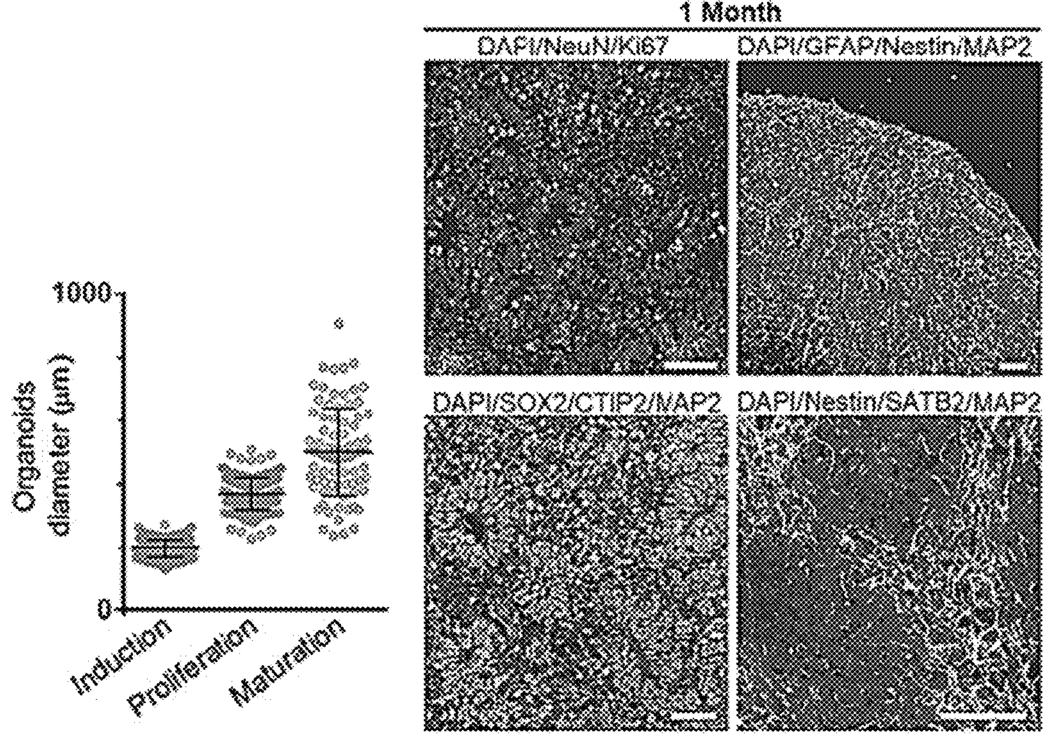
Figure 1G:
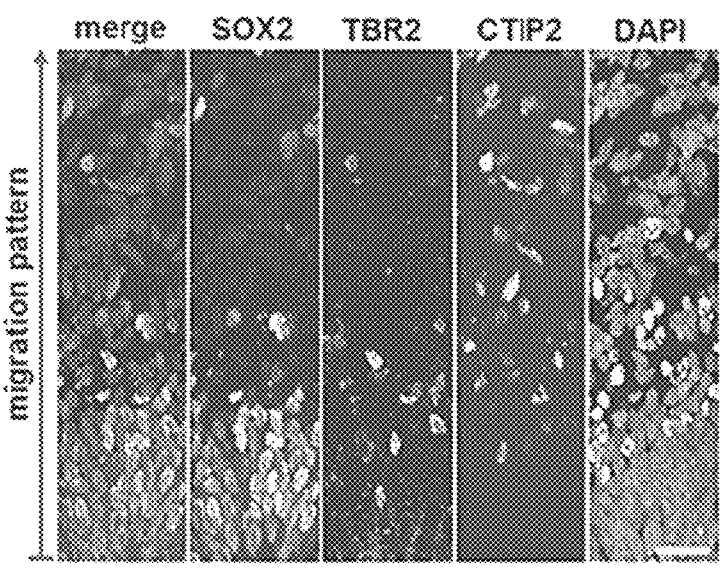
Figure 1H:
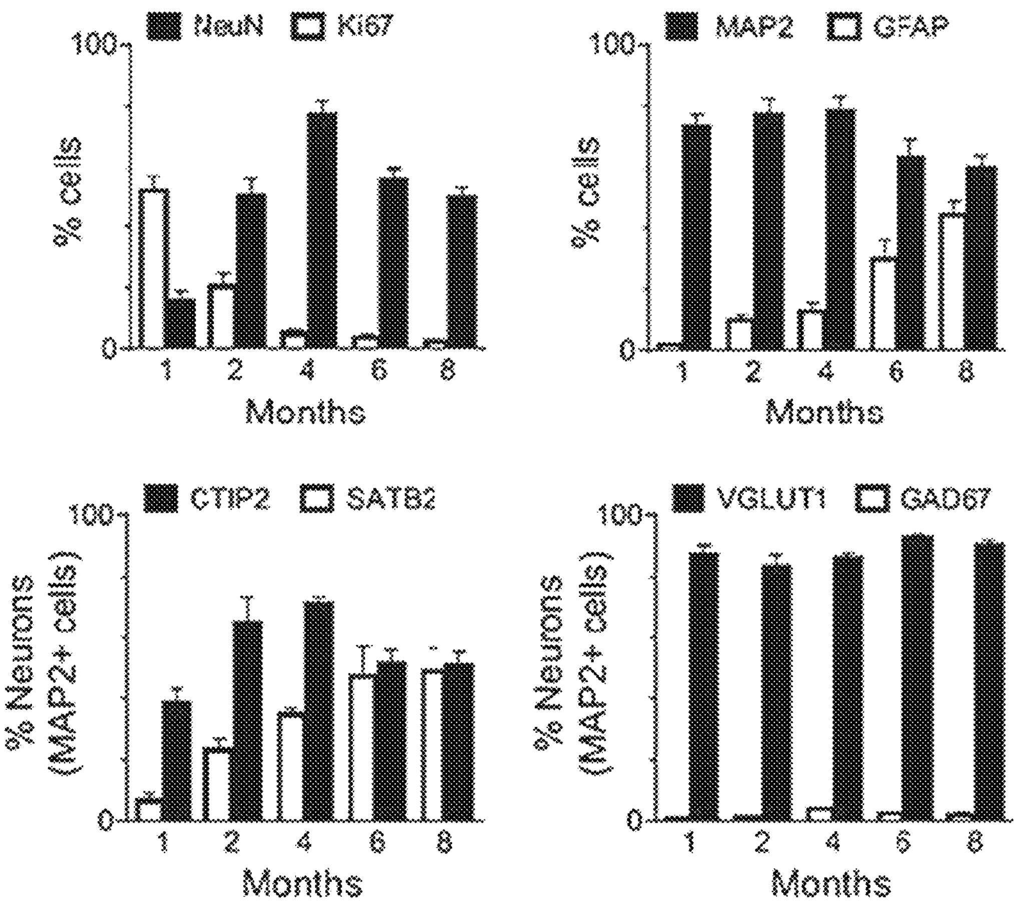
Figures 1I, 1J, 1K:
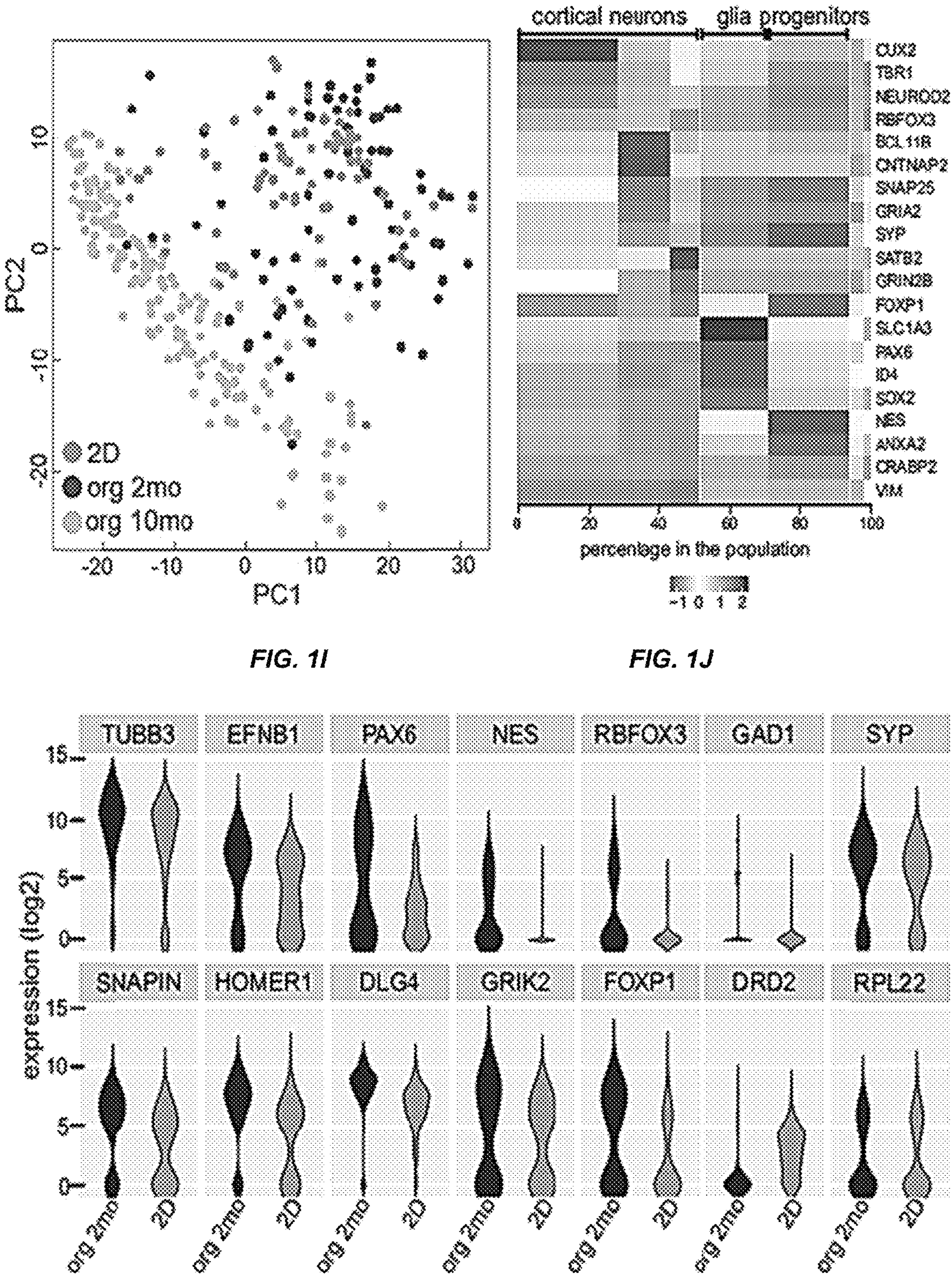
Figure 1L:
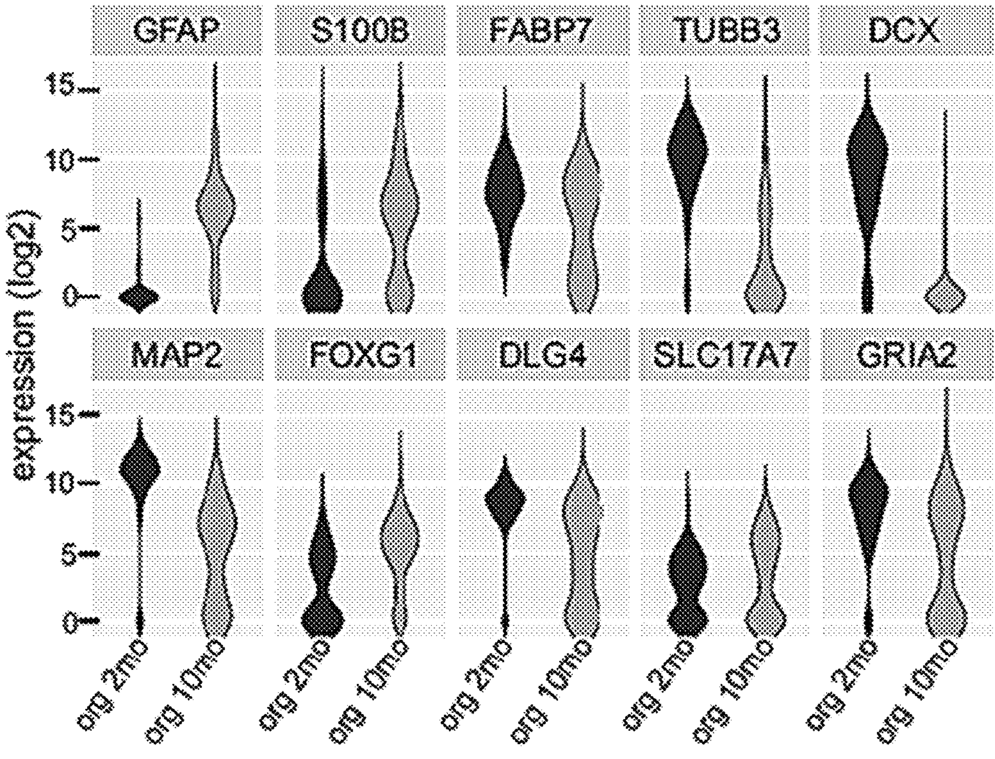
Figure 1M:
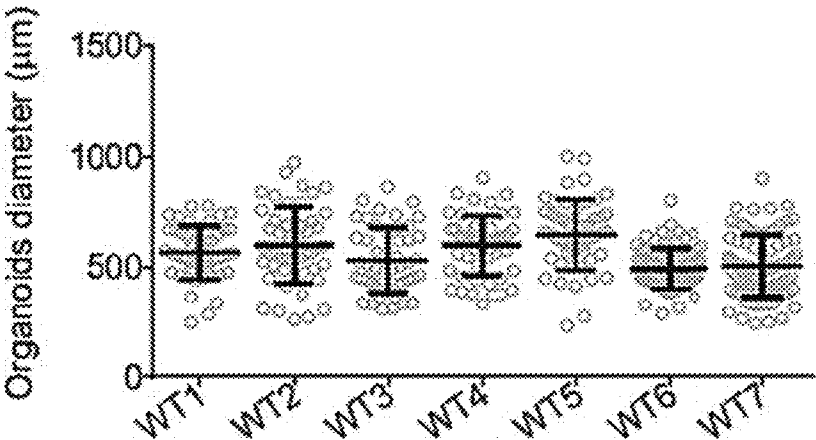

Development of functional cortical organoids. Despite the structural and transcriptional similarities between brain organoids and the developing nervous system, the emergence of higher-level complex network activity comparable to the living human brain remains largely untested (e.g., see FIG. 1A). In order to investigate the formation of a functional network, cortical specification was promoted by modifying previously described protocols (e.g., see FIG. 1B). At the beginning of the differentiation, an abundance of proliferative neural progenitor cells (NPCs) ($Ki67^+$, $SOX2^+$ and $Nestin^+$) that self-organized into a polarized neuroepithelium-like structure was observed (e.g., see FIG. 1D). Similar to cortical development in vivo, the proliferative zone around a lumen delimited by β-$catenin^+$ cells were surrounded by progenitor cells (e.g., see FIG. 1E). At this stage, the natural folding of the cortical plate was observed. Progressively, the organoids increased in size and in the proportion of mature neurons ($NeuN^+$ and $MAP2^+$) to ultimately develop into concentric multi-layer structures composed of NPCs, intermediate progenitors, lower ($TBR2^+$ and $CTIP2^+/TBR1^+$) and upper ($SATB2^+$) cortical layer neurons (e.g., see FIG. 1B-H and FIG. 1M). Although the initial fraction of glial cells was less than 5%, this population increased to about 30-40% after 6 months of differentiation (e.g., see FIG. 1D-I, and FIG. 1K-L). Comparable results were observed with different iPSC lines, confirming the reproducibility and consistency of this protocol. The single-cell gene expression profile of cortical organoids was assessed and compared to 2D monolayer differentiation. After 2 months of maturation, cortical organoids expressed higher levels of maturation and synaptic markers, while at 10 months, glial populations increased substantially, consistent with the immunostainings (e.g., see FIGS. 1I, K, and L). The maturation level of the cells is reflected by the presence of pyramidally-shaped neurons, formation of dendritic spines and structurally defined synapses.

TABLE 1

Comparison among different organoid protocols.

| | Lancaster et al. 2013 | Pasca et al. 2015 | Qian et al. 2016 | Birey et al. 2017 | Quadrato et al. 2017 | Lancaster et al. 2017 | Present Data |
|---|---|---|---|---|---|---|---|
| Feeder-free iPSCs culture conditions | — | — | — | — | x | — | x |
| Early-stage cortical neural induction | — | — | x | — | — | — | x |
| Small molecules neural induction | — | x | x | x | — | x | x |
| Extended exposure to growth factors | — | x | x | x | — | — | — |
| Long-term maturation with growth factors and/or small molecules | x | — | x | — | x | — | — |
| Generation of a high number of organoids per batch | — | — | — | — | — | — | x |
| Intermediate state with Matrigel-embedded organoids | x | — | x | — | x | x | — |
| Cortical-enriched neural differentiation | — | x | x | x | — | — | x |
| Defined media during neural differentiation (FBS) | x | x | x | x | — | x | x |
| Low variability of size among organoids and between batches | — | n/a | x | n/a | — | — | x |
| Use of microfilaments | — | — | — | — | — | x | — |
| Use of specialized equipment (spinning bioreactor) | x | — | x | — | x | x | — |
| Low variability at functional level | n/a | x | n/a | n/a | — | n/a | x |
| Complex functional neural activity (network oscillations) | — | — | — | — | — | — | x |

n/a: not available

Figures 1N, 2A, 2B:
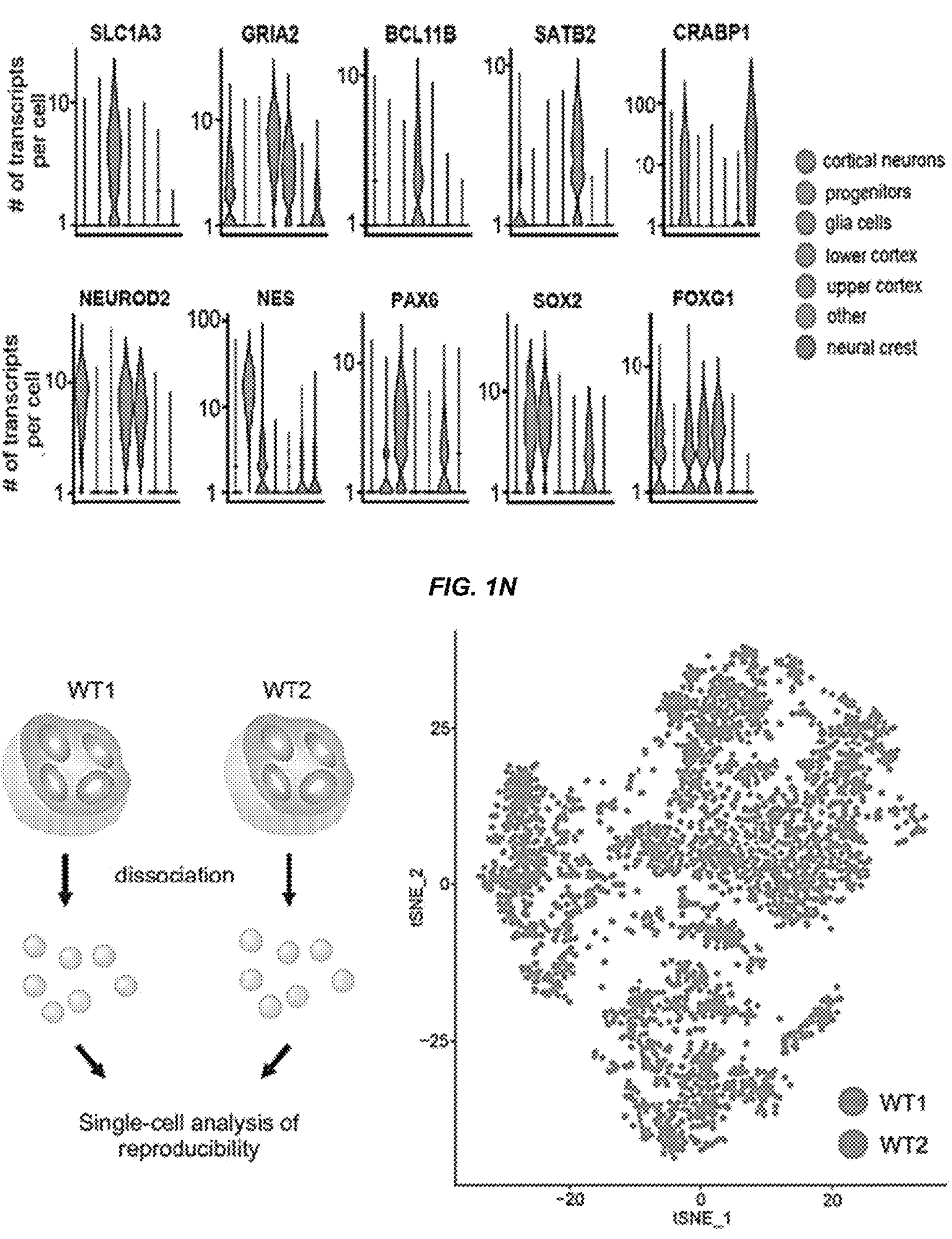
Figures 3C, 3D, 4A:
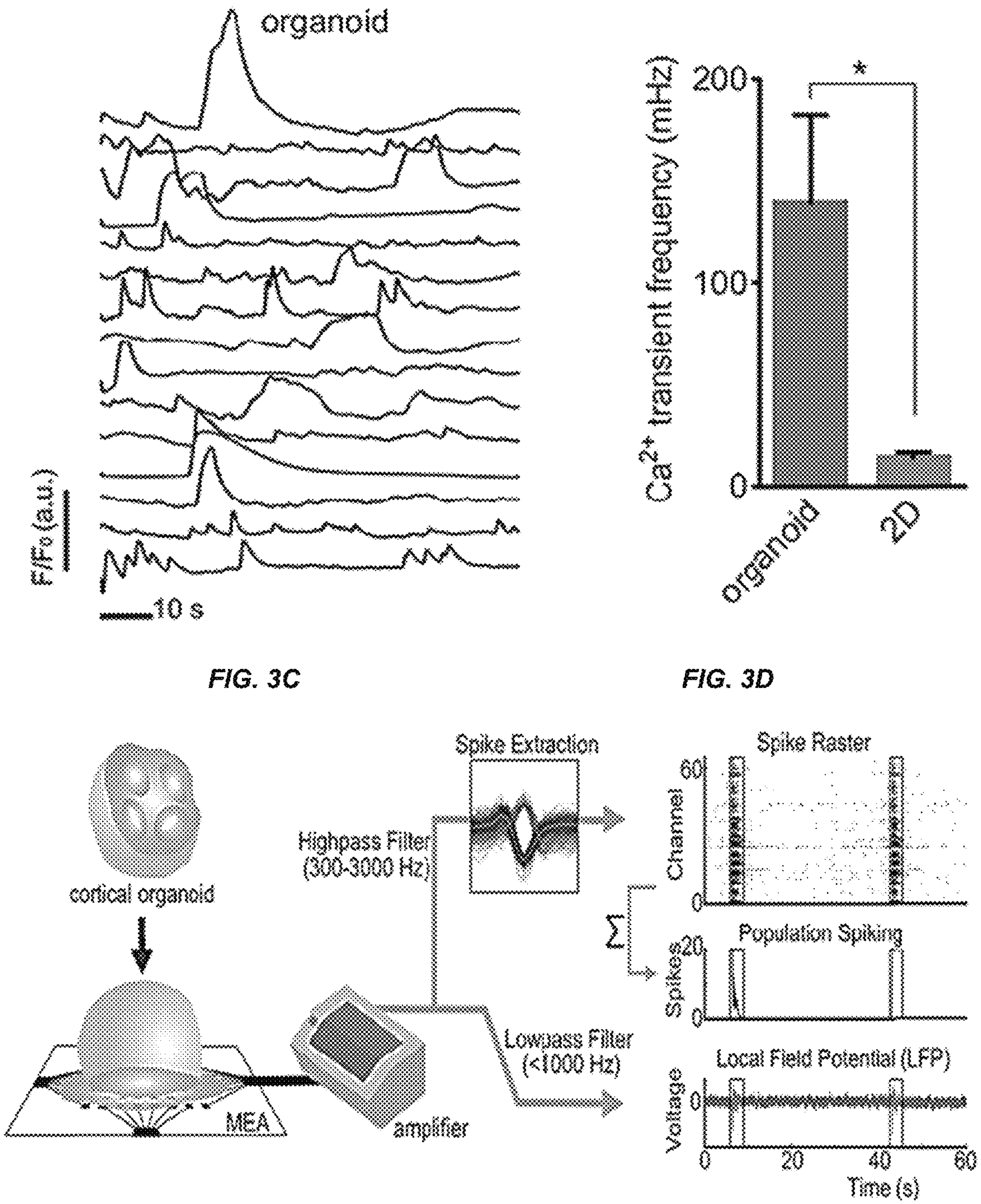
Figures 4B, 4C, 4D:
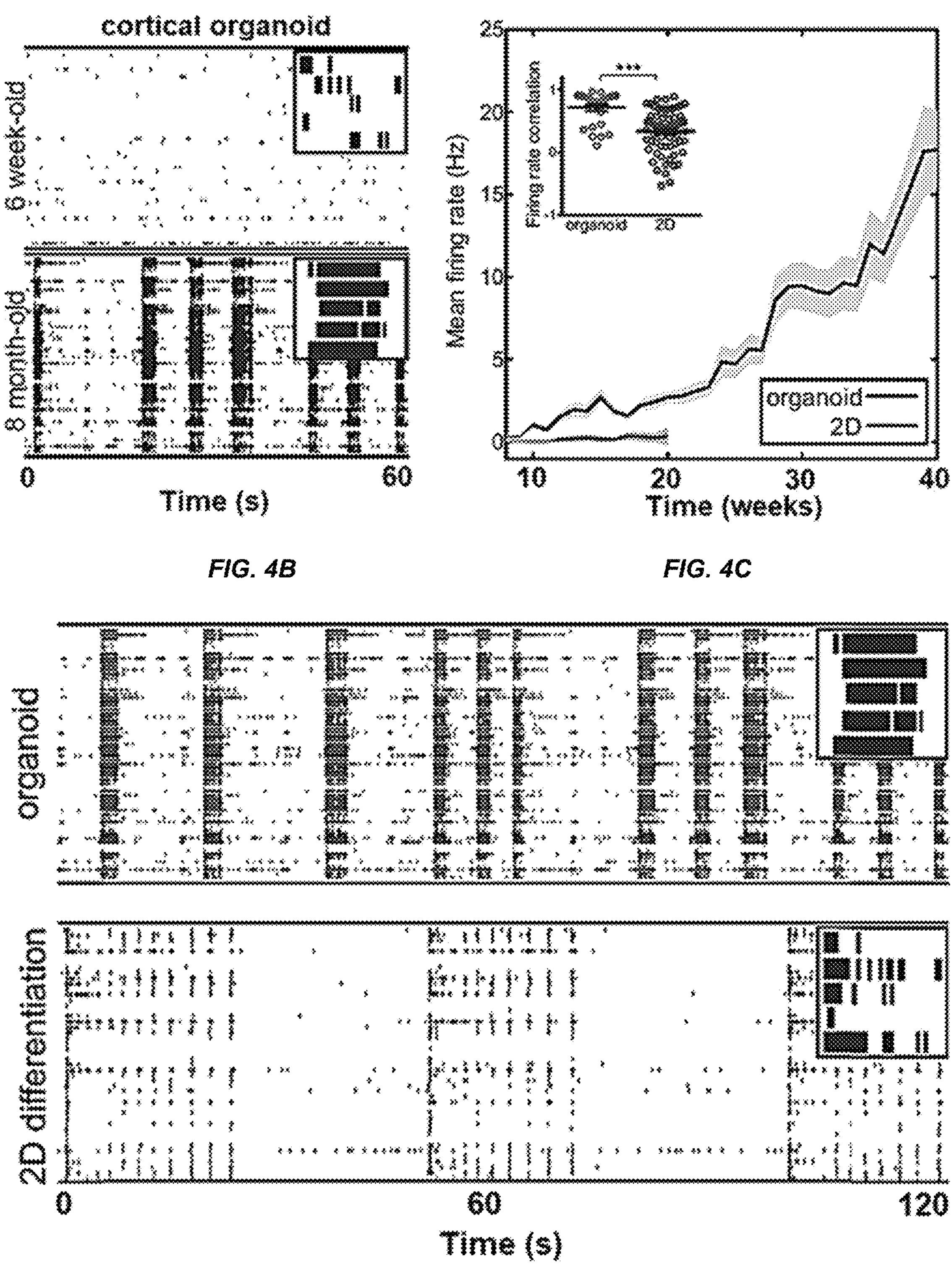
Figure 4G:
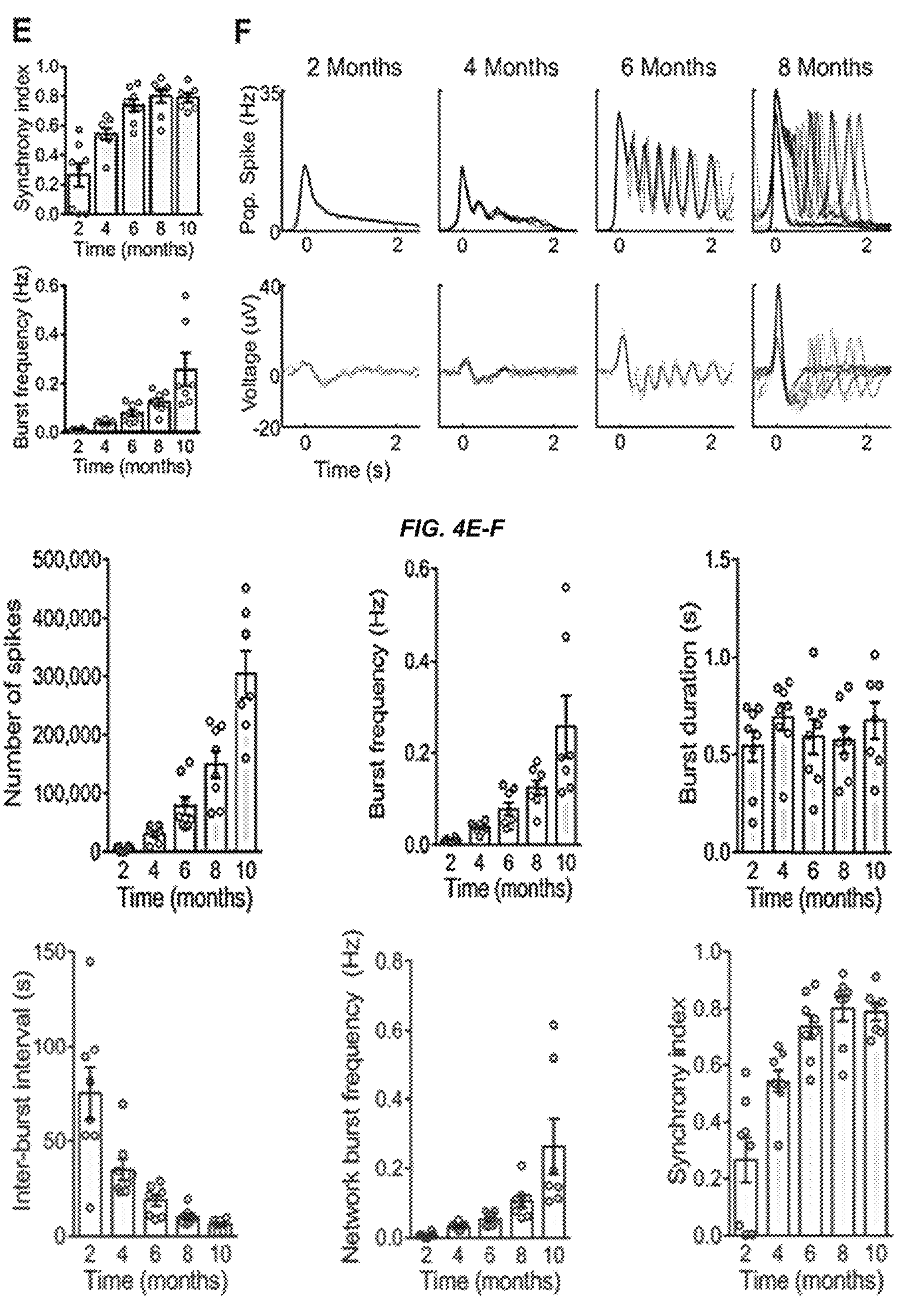
Figures 4H, 4I, 4J, 4K, 5A:
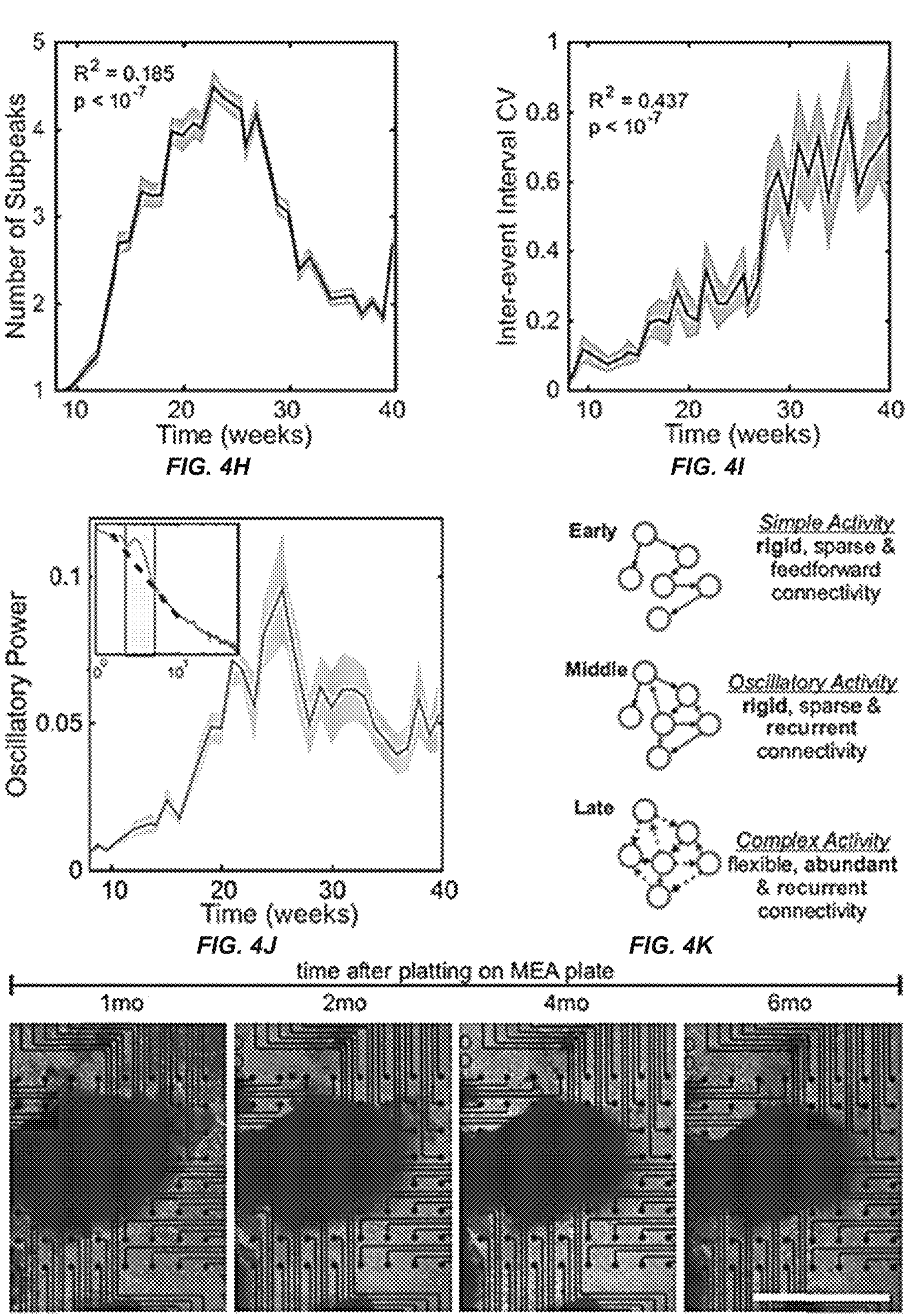

To further characterize the cellular diversity of a cortical organoid, single-cell gene expression profiling was performed in 6-month-old organoids and used unbiased clustering to classify the main existing cell types. From two independent differentiation replicates (e.g., see FIG. 2), seven distinct clusters were characterized based on their differential gene expression patterns (Table 2) including: progenitors, glia, and cortical neurons, which could be further subdivided into lower and upper layer based on the expression of the layer-specific markers CTIP2 and SATB2, respectively (e.g., see FIG. 1J and FIG. 1N). These data suggested that cortical organoids can accelerate neuronal maturation and ultimately generate greater neural diversity.

TABLE 2

Top Expressed genes of each cell cluster

| Cluster | Gene | myAUC | avg_diff | power | avg_logFC | pct. 1 | pct. 2 |
|---|---|---|---|---|---|---|---|
| Cortical neurons | SOX11 | 0.889 | 1.29996 | 0.778 | 1.29996 | 0.996 | 0.864 |
| Cortical neurons | NEUROD2 | 0.886 | 1.366603 | 0.772 | 1.366603 | 0.944 | 0.382 |
| Cortical neurons | GPM6A | 0.885 | 1.12235 | 0.77 | 1.12235 | 0.992 | 0.679 |
| Cortical neurons | SOX4 | 0.879 | 0.985057 | 0.758 | 0.985057 | 1 | 0.965 |
| Cortical neurons | MLLT11 | 0.856 | 0.916514 | 0.712 | 0.916514 | 0.998 | 0.869 |
| Cortical neurons | CCNI | 0.843 | 0.707003 | 0.686 | 0.707003 | 1 | 0.994 |
| Cortical neurons | SLA | 0.833 | 1.424488 | 0.666 | 1.424488 | 0.821 | 0.303 |
| Cortical neurons | MARCKSL1 | 0.832 | 0.578678 | 0.664 | 0.578678 | 0.999 | 0.981 |
| Cortical neurons | DCX | 0.806 | 0.81224 | 0.612 | 0.81224 | 0.969 | 0.576 |
| Progenitors | NES | 0.976 | 1.785855 | 0.952 | 1.785855 | 0.997 | 0.303 |
| Progenitors | ANXA2 | 0.972 | 2.407607 | 0.944 | 2.407607 | 0.976 | 0.149 |
| Progenitors | GYPC | 0.963 | 1.587675 | 0.926 | 1.587675 | 0.954 | 0.065 |
| Progenitors | SPARC | 0.958 | 1.745727 | 0.916 | 1.745727 | 0.978 | 0.24 |
| Progenitors | SDC2 | 0.944 | 1.388854 | 0.888 | 1.388854 | 0.924 | 0.08 |
| Progenitors | CRABP2 | 0.942 | 1.564316 | 0.884 | 1.564316 | 0.939 | 0.11 |
| Progenitors | NTRK2 | 0.941 | 1.61904 | 0.882 | 1.61904 | 0.912 | 0.057 |
| Progenitors | CCND1 | 0.941 | 1.505771 | 0.882 | 1.505771 | 0.909 | 0.046 |
| Progenitors | LGALS1 | 0.938 | 2.0633 | 0.876 | 2.0633 | 0.94 | 0.17 |
| Progenitors | SERF2 | 0.934 | 0.95158 | 0.868 | 0.95158 | 1 | 0.903 |
| Progenitors | MDK | 0.933 | 1.279235 | 0.866 | 1.279235 | 0.996 | 0.832 |
| Progenitors | VGLL3 | 0.931 | 1.237999 | 0.862 | 1.237999 | 0.887 | 0.032 |

TABLE 2-continued

| Top Expressed genes of each cell cluster | | | | | | | |
|---|---|---|---|---|---|---|---|
| Cluster | Gene | myAUC | avg_diff | power | avg_logFC | pct. 1 | pct. 2 |
| Progenitors | S100A13 | 0.917 | 1.839522 | 0.834 | 1.839522 | 0.893 | 0.12 |
| Progenitors | PDLIM7 | 0.916 | 1.185298 | 0.832 | 1.185298 | 0.94 | 0.25 |
| Progenitors | ANXA5 | 0.902 | 1.221643 | 0.804 | 1.221643 | 0.926 | 0.184 |
| Progenitors | PRSS23 | 0.901 | 1.501512 | 0.802 | 1.501512 | 0.836 | 0.06 |
| Progenitors | RPL41 | 0.897 | 0.625131 | 0.794 | 0.625131 | 1 | 0.999 |
| Progenitors | NPC2 | 0.895 | 1.182853 | 0.79 | 1.182853 | 0.951 | 0.407 |
| Progenitors | SEC11A | 0.894 | 0.828695 | 0.788 | 0.828695 | 0.98 | 0.64 |
| Progenitors | PRDX6 | 0.892 | 0.981071 | 0.784 | 0.981071 | 0.98 | 0.555 |
| Progenitors | TPM1 | 0.887 | 1.731952 | 0.774 | 1.731952 | 0.938 | 0.518 |
| Progenitors | RHOC | 0.887 | 0.962424 | 0.774 | 0.962424 | 0.907 | 0.206 |
| Progenitors | NEAT1 | 0.883 | 1.352256 | 0.766 | 1.352256 | 0.948 | 0.285 |
| Progenitors | RPL12 | 0.882 | 0.706881 | 0.764 | 0.706881 | 0.999 | 0.992 |
| Progenitors | RPL7A | 0.881 | 0.613375 | 0.762 | 0.613375 | 1 | 0.997 |
| Progenitors | EEF1A1 | 0.879 | 0.651914 | 0.758 | 0.651914 | 1 | 1 |
| Progenitors | RPL28 | 0.876 | 0.592999 | 0.752 | 0.592999 | 1 | 0.995 |
| Progenitors | RPS6 | 0.871 | 0.711767 | 0.742 | 0.711767 | 0.997 | 0.994 |
| Progenitors | RPL23A | 0.867 | 0.568383 | 0.734 | 0.568383 | 0.999 | 0.994 |
| Progenitors | TIMP1 | 0.865 | 0.772749 | 0.73 | 0.772749 | 0.895 | 0.173 |
| Progenitors | RPL8 | 0.864 | 0.572428 | 0.728 | 0.572428 | 0.999 | 0.997 |
| Progenitors | METRN | 0.863 | 0.835332 | 0.726 | 0.835332 | 0.907 | 0.229 |
| Progenitors | WLS | 0.859 | 0.916782 | 0.718 | 0.916782 | 0.736 | 0.023 |
| Progenitors | RPL27A | 0.858 | 0.534803 | 0.716 | 0.534803 | 1 | 0.998 |
| Progenitors | CTGF | 0.857 | 1.335629 | 0.714 | 1.335629 | 0.727 | 0.017 |
| Progenitors | RCN1 | 0.857 | 0.806462 | 0.714 | 0.806462 | 0.967 | 0.377 |
| Progenitors | PFN1 | 0.857 | 0.738107 | 0.714 | 0.738107 | 0.99 | 0.844 |
| Progenitors | PMP22 | 0.855 | 1.601169 | 0.71 | 1.601169 | 0.778 | 0.101 |
| Progenitors | ITGB8 | 0.855 | 1.138802 | 0.71 | 1.138802 | 0.868 | 0.201 |
| Progenitors | SERPINH1 | 0.854 | 0.713982 | 0.708 | 0.713982 | 0.846 | 0.143 |
| Progenitors | VIM | 0.853 | 1.146246 | 0.706 | 1.146246 | 1 | 0.77 |
| Progenitors | NME4 | 0.852 | 0.813408 | 0.704 | 0.813408 | 0.945 | 0.457 |
| Progenitors | RPS7 | 0.852 | 0.558045 | 0.704 | 0.558045 | 0.999 | 0.997 |
| Progenitors | MYL12A | 0.85 | 0.739735 | 0.7 | 0.739735 | 0.84 | 0.157 |
| Progenitors | RPS20 | 0.849 | 0.558658 | 0.698 | 0.558658 | 1 | 0.991 |
| Progenitors | RPS2 | 0.848 | 0.524557 | 0.696 | 0.524557 | 0.999 | 1 |
| Progenitors | RPLP1 | 0.848 | 0.514123 | 0.696 | 0.514123 | 1 | 0.998 |
| Progenitors | RAB13 | 0.846 | 0.808108 | 0.692 | 0.808108 | 0.86 | 0.204 |
| Progenitors | TUBB6 | 0.845 | 0.757197 | 0.69 | 0.757197 | 0.806 | 0.121 |
| Progenitors | CRNDE | 0.843 | 0.802352 | 0.686 | 0.802352 | 0.954 | 0.472 |
| Progenitors | TTYH1 | 0.84 | 0.971997 | 0.68 | 0.971997 | 0.963 | 0.416 |
| Progenitors | RPL23 | 0.84 | 0.546833 | 0.68 | 0.546833 | 1 | 0.997 |
| Progenitors | RPS19 | 0.84 | 0.516859 | 0.68 | 0.516859 | 1 | 1 |
| Progenitors | RPL29 | 0.84 | 0.464037 | 0.68 | 0.464037 | 1 | 0.997 |
| Progenitors | RPS14 | 0.839 | 0.462974 | 0.678 | 0.462974 | 1 | 0.999 |
| Progenitors | RPL3 | 0.838 | 0.497988 | 0.676 | 0.497988 | 1 | 0.998 |
| Progenitors | SLC25A6 | 0.835 | 0.71474 | 0.67 | 0.71474 | 0.995 | 0.891 |
| Progenitors | SPATS2L | 0.831 | 0.9606 | 0.662 | 0.9606 | 0.811 | 0.193 |
| Progenitors | QPRT | 0.83 | 0.651751 | 0.66 | 0.651751 | 0.855 | 0.198 |
| Progenitors | RPL35 | 0.83 | 0.470972 | 0.66 | 0.470972 | 0.999 | 0.993 |
| Progenitors | RPS18 | 0.828 | 0.49256 | 0.656 | 0.49256 | 1 | 1 |
| Progenitors | CLIC1 | 0.827 | 0.723496 | 0.654 | 0.723496 | 0.937 | 0.427 |
| Progenitors | RPS3 | 0.827 | 0.526597 | 0.654 | 0.526597 | 1 | 0.997 |
| Progenitors | RPL10A | 0.827 | 0.523565 | 0.654 | 0.523565 | 1 | 0.994 |
| Progenitors | RPS28 | 0.825 | 0.506021 | 0.65 | 0.506021 | 1 | 0.993 |
| Progenitors | CD63 | 0.824 | 0.710828 | 0.648 | 0.710828 | 0.991 | 0.76 |
| Progenitors | PDPN | 0.824 | 0.65191 | 0.648 | 0.65191 | 0.699 | 0.046 |
| Progenitors | ACTG1 | 0.824 | 0.488252 | 0.648 | 0.488252 | 1 | 1 |
| Progenitors | CCNG1 | 0.823 | 0.727443 | 0.646 | 0.727443 | 0.924 | 0.38 |
| Progenitors | CD99 | 0.82 | 0.68859 | 0.64 | 0.68859 | 0.953 | 0.405 |
| Progenitors | B2M | 0.817 | 0.787786 | 0.634 | 0.787786 | 0.947 | 0.392 |
| Progenitors | CHCHD10 | 0.817 | 0.645222 | 0.634 | 0.645222 | 0.84 | 0.211 |
| Progenitors | RPLP0 | 0.817 | 0.469741 | 0.634 | 0.469741 | 1 | 0.997 |
| Progenitors | RPS27L | 0.816 | 0.744701 | 0.632 | 0.744701 | 0.995 | 0.664 |
| Progenitors | COL1A2 | 0.815 | 0.896012 | 0.63 | 0.896012 | 0.647 | 0.019 |
| Progenitors | PFN2 | 0.815 | 0.622861 | 0.63 | 0.622861 | 0.991 | 0.763 |
| Progenitors | UBB | 0.813 | 0.783749 | 0.626 | 0.783749 | 0.978 | 0.588 |
| Progenitors | RPL37 | 0.813 | 0.465752 | 0.626 | 0.465752 | 1 | 0.995 |
| Progenitors | CRABP1 | 0.811 | 1.087669 | 0.622 | 1.087669 | 0.737 | 0.133 |
| Progenitors | RPL7 | 0.811 | 0.467728 | 0.622 | 0.467728 | 1 | 0.998 |
| Progenitors | FSTL1 | 0.81 | 0.761788 | 0.62 | 0.761788 | 0.737 | 0.123 |
| Progenitors | RPL36 | 0.81 | 0.434708 | 0.62 | 0.434708 | 1 | 0.992 |
| Progenitors | RPL19 | 0.81 | 0.401045 | 0.62 | 0.401045 | 1 | 1 |
| Progenitors | FGFR1 | 0.809 | 0.608769 | 0.618 | 0.608769 | 0.839 | 0.204 |
| Progenitors | ENO1 | 0.808 | 0.582772 | 0.616 | 0.582772 | 0.996 | 0.869 |
| Progenitors | RPS15 | 0.806 | 0.381154 | 0.612 | 0.381154 | 1 | 0.999 |
| Progenitors | MYL6 | 0.805 | 0.530039 | 0.61 | 0.530039 | 1 | 0.986 |
| Progenitors | GSTP1 | 0.804 | 0.634369 | 0.608 | 0.634369 | 0.996 | 0.92 |

TABLE 2-continued

Top Expressed genes of each cell cluster

| Cluster | Gene | myAUC | avg_diff | power | avg_logFC | pct. 1 | pct. 2 |
|---|---|---|---|---|---|---|---|
| Progenitors | PODXL | 0.804 | 0.622402 | 0.608 | 0.622402 | 0.67 | 0.06 |
| Progenitors | CNN3 | 0.804 | 0.616921 | 0.608 | 0.616921 | 0.992 | 0.669 |
| Progenitors | GNG11 | 0.803 | 0.751478 | 0.606 | 0.751478 | 0.668 | 0.064 |
| Progenitors | RPS4Y1 | 0.803 | 0.680093 | 0.606 | 0.680093 | 0.963 | 0.62 |
| Progenitors | AHNAK | 0.803 | 0.651782 | 0.606 | 0.651782 | 0.64 | 0.036 |
| Progenitors | CST3 | 0.802 | 0.645478 | 0.604 | 0.645478 | 0.963 | 0.567 |
| Progenitors | RPS23 | 0.801 | 0.419435 | 0.602 | 0.419435 | 1 | 0.998 |
| Progenitors | RPL13A | 0.801 | 0.409875 | 0.602 | 0.409875 | 1 | 1 |
| Glia | SFRP1 | 0.94 | 2.001041 | 0.88 | 2.001041 | 0.952 | 0.385 |
| Glia | SOX2 | 0.909 | 1.356804 | 0.818 | 1.356804 | 0.946 | 0.321 |
| Glia | Clorf61 | 0.893 | 1.500525 | 0.786 | 1.500525 | 0.984 | 0.749 |
| Glia | FABP7 | 0.887 | 1.707591 | 0.774 | 1.707591 | 0.985 | 0.736 |
| Glia | SLC1A3 | 0.88 | 1.56662 | 0.76 | 1.56662 | 0.807 | 0.119 |
| Glia | SYNE2 | 0.876 | 1.218806 | 0.752 | 1.218806 | 0.919 | 0.445 |
| Glia | PAX6 | 0.871 | 1.251984 | 0.742 | 1.251984 | 0.83 | 0.186 |
| Glia | HMGN3 | 0.866 | 0.91378 | 0.732 | 0.91378 | 0.978 | 0.849 |
| Glia | ID4 | 0.851 | 1.407158 | 0.702 | 1.407158 | 0.875 | 0.381 |
| Glia | MYO10 | 0.85 | 1.025069 | 0.7 | 1.025069 | 0.857 | 0.338 |
| Glia | DBI | 0.842 | 1.242287 | 0.684 | 1.242287 | 0.958 | 0.709 |
| Glia | PTN | 0.836 | 1.579917 | 0.672 | 1.579917 | 0.948 | 0.752 |
| Glia | QKI | 0.83 | 0.909655 | 0.66 | 0.909655 | 0.891 | 0.502 |
| Glia | LINC01158 | 0.818 | 0.903364 | 0.636 | 0.903364 | 0.901 | 0.546 |
| Glia | ZFHX4 | 0.817 | 1.004117 | 0.634 | 1.004117 | 0.707 | 0.132 |
| Glia | HES1 | 0.812 | 1.171994 | 0.624 | 1.171994 | 0.718 | 0.17 |
| Glia | HMGB2 | 0.809 | 1.270445 | 0.618 | 1.270445 | 0.921 | 0.594 |
| Glia | LHX2 | 0.806 | 0.931067 | 0.612 | 0.931067 | 0.846 | 0.398 |
| Lower cortex | SNAP25 | 0.942 | 1.540645 | 0.884 | 1.540645 | 0.987 | 0.415 |
| Lower cortex | GRIA2 | 0.892 | 1.185847 | 0.784 | 1.185847 | 0.96 | 0.352 |
| Lower cortex | CNTNAP2 | 0.88 | 1.447084 | 0.76 | 1.447084 | 0.876 | 0.272 |
| Lower cortex | CELF4 | 0.863 | 1.071334 | 0.726 | 1.071334 | 0.886 | 0.265 |
| Lower cortex | NSG2 | 0.851 | 1.031537 | 0.702 | 1.031537 | 0.96 | 0.403 |
| Lower cortex | SYT1 | 0.85 | 0.985569 | 0.7 | 0.985569 | 0.983 | 0.61 |
| Lower cortex | YWHAH | 0.841 | 0.785308 | 0.682 | 0.785308 | 0.973 | 0.805 |
| Lower cortex | SNCA | 0.839 | 0.953942 | 0.678 | 0.953942 | 0.914 | 0.451 |
| Lower cortex | BASP1 | 0.838 | 0.734567 | 0.676 | 0.734567 | 1 | 0.943 |
| Lower cortex | DOK6 | 0.831 | 1.000188 | 0.662 | 1.000188 | 0.814 | 0.264 |
| Lower cortex | RTN1 | 0.823 | 0.898627 | 0.646 | 0.898627 | 0.985 | 0.519 |
| Lower cortex | RUNX1T1 | 0.82 | 0.94366 | 0.64 | 0.94366 | 0.852 | 0.281 |
| Lower cortex | FAM49A | 0.817 | 0.920672 | 0.634 | 0.920672 | 0.821 | 0.28 |
| Lower cortex | MAP1B | 0.817 | 0.603691 | 0.634 | 0.603691 | 1 | 0.995 |
| Lower cortex | SYT4 | 0.816 | 0.939245 | 0.632 | 0.939245 | 0.821 | 0.262 |
| Lower cortex | B3GALT2 | 0.815 | 1.017411 | 0.63 | 1.017411 | 0.757 | 0.2 |
| Lower cortex | GABRB2 | 0.815 | 0.991632 | 0.63 | 0.991632 | 0.675 | 0.062 |
| Lower cortex | LMO3 | 0.814 | 1.36195 | 0.628 | 1.36195 | 0.688 | 0.101 |
| Lower cortex | SCG3 | 0.811 | 0.757346 | 0.622 | 0.757346 | 0.939 | 0.415 |
| Lower cortex | UCHL1 | 0.809 | 0.66339 | 0.618 | 0.66339 | 0.99 | 0.906 |
| Lower cortex | VAMP2 | 0.809 | 0.606955 | 0.618 | 0.606955 | 0.994 | 0.939 |
| Lower cortex | TMEM161B-AS1 | 0.808 | 0.816917 | 0.616 | 0.816917 | 0.941 | 0.63 |
| Lower cortex | LY6H | 0.806 | 0.807691 | 0.612 | 0.807691 | 0.88 | 0.34 |
| Lower cortex | MAPT | 0.805 | 0.73704 | 0.61 | 0.73704 | 0.962 | 0.486 |
| Lower cortex | CDKN2D | 0.802 | 0.762383 | 0.604 | 0.762383 | 0.878 | 0.4 |
| Lower cortex | RAB3A | 0.801 | 0.697869 | 0.602 | 0.697869 | 0.924 | 0.413 |
| Upper cortex | MEF2C | 0.954 | 2.051853 | 0.908 | 2.051853 | 0.986 | 0.369 |
| Upper cortex | STMN2 | 0.885 | 1.043931 | 0.77 | 1.043931 | 1 | 0.644 |
| Upper cortex | NSG2 | 0.883 | 1.126043 | 0.766 | 1.126043 | 1 | 0.441 |
| Upper cortex | ARPP21 | 0.88 | 1.115469 | 0.76 | 1.115469 | 0.883 | 0.189 |
| Upper cortex | STMN4 | 0.874 | 0.982886 | 0.748 | 0.982886 | 1 | 0.696 |
| Upper cortex | MAPT | 0.87 | 0.908315 | 0.74 | 0.908315 | 1 | 0.518 |
| Upper cortex | GRIN2B | 0.869 | 1.002716 | 0.738 | 1.002716 | 0.9 | 0.246 |
| Upper cortex | CALM1 | 0.868 | 0.733117 | 0.736 | 0.733117 | 1 | 0.988 |
| Upper cortex | NELL2 | 0.861 | 0.95751 | 0.722 | 0.95751 | 0.973 | 0.409 |
| Upper cortex | SCD5 | 0.855 | 0.913699 | 0.71 | 0.913699 | 0.931 | 0.478 |
| Upper cortex | SATB2 | 0.853 | 0.902036 | 0.706 | 0.902036 | 0.811 | 0.125 |
| Upper cortex | PKIA | 0.849 | 0.808509 | 0.698 | 0.808509 | 0.952 | 0.445 |
| Upper cortex | MAP1B | 0.849 | 0.669352 | 0.698 | 0.669352 | 1 | 0.995 |
| Upper cortex | INA | 0.847 | 0.831367 | 0.694 | 0.831367 | 0.966 | 0.437 |
| Upper cortex | STMN1 | 0.845 | 0.783568 | 0.69 | 0.783568 | 1 | 0.979 |
| Upper cortex | NEUROD6 | 0.843 | 1.007963 | 0.686 | 1.007963 | 0.986 | 0.502 |
| Upper cortex | VAMP2 | 0.843 | 0.689091 | 0.686 | 0.689091 | 0.993 | 0.943 |
| Upper cortex | DOK5 | 0.841 | 0.93379 | 0.682 | 0.93379 | 0.935 | 0.559 |
| Upper cortex | RASL11B | 0.841 | 0.930199 | 0.682 | 0.930199 | 0.821 | 0.209 |
| Upper cortex | SNCA | 0.841 | 0.896556 | 0.682 | 0.896556 | 0.952 | 0.482 |
| Upper cortex | R3HDM1 | 0.84 | 0.924861 | 0.68 | 0.924861 | 0.89 | 0.386 |
| Upper cortex | TTC9B | 0.84 | 0.868857 | 0.68 | 0.868857 | 0.959 | 0.435 |
| Upper cortex | RAC3 | 0.83 | 0.70783 | 0.66 | 0.70783 | 0.945 | 0.624 |
| Upper cortex | CXADR | 0.827 | 0.785512 | 0.654 | 0.785512 | 0.993 | 0.719 |

TABLE 2-continued

| Top Expressed genes of each cell cluster | | | | | | | |
|---|---|---|---|---|---|---|---|
| Cluster | Gene | myAUC | avg_diff | power | avg_logFC | pct. 1 | pct. 2 |
| Upper cortex | HN1 | 0.827 | 0.602815 | 0.654 | 0.602815 | 1 | 0.961 |
| Upper cortex | CAMK2B | 0.822 | 0.749623 | 0.644 | 0.749623 | 0.897 | 0.279 |
| Upper cortex | RTN1 | 0.819 | 0.807888 | 0.638 | 0.807888 | 1 | 0.553 |
| Upper cortex | CHL1 | 0.819 | 0.775621 | 0.638 | 0.775621 | 0.918 | 0.374 |
| Upper cortex | NSG1 | 0.818 | 0.708593 | 0.636 | 0.708593 | 0.997 | 0.528 |
| Upper cortex | TUBB2A | 0.817 | 0.659235 | 0.634 | 0.659235 | 1 | 0.946 |
| Upper cortex | GABBR2 | 0.815 | 0.777596 | 0.63 | 0.777596 | 0.79 | 0.182 |
| Upper cortex | RBFOX2 | 0.814 | 0.677032 | 0.628 | 0.677032 | 0.99 | 0.662 |
| Upper cortex | CRMP1 | 0.813 | 0.666121 | 0.626 | 0.666121 | 0.979 | 0.79 |
| Upper cortex | GAP43 | 0.811 | 0.737576 | 0.622 | 0.737576 | 0.997 | 0.816 |
| Upper cortex | UCHL1 | 0.809 | 0.645161 | 0.618 | 0.645161 | 1 | 0.911 |
| Upper cortex | CDKN2D | 0.808 | 0.694482 | 0.616 | 0.694482 | 0.935 | 0.43 |
| Upper cortex | NCAM1 | 0.805 | 0.694452 | 0.61 | 0.694452 | 0.955 | 0.551 |
| Upper cortex | MSRA | 0.804 | 0.734229 | 0.608 | 0.734229 | 0.814 | 0.288 |
| Upper cortex | GPR85 | 0.801 | 0.76111 | 0.602 | 0.76111 | 0.766 | 0.189 |
| Upper cortex | DAAM1 | 0.801 | 0.628961 | 0.602 | 0.628961 | 0.993 | 0.776 |
| Other | ALDOA | 0.917 | 1.757415 | 0.834 | 1.757415 | 0.963 | 0.838 |
| Other | EIF1 | 0.888 | 0.999198 | 0.776 | 0.999198 | 1 | 0.999 |
| Other | FTL | 0.883 | 1.541462 | 0.766 | 1.541462 | 1 | 0.997 |
| Other | BNIP3 | 0.87 | 1.504624 | 0.74 | 1.504624 | 0.844 | 0.345 |
| Other | FAM162A | 0.857 | 1.366057 | 0.714 | 1.366057 | 0.881 | 0.459 |
| Other | ARF4 | 0.848 | 1.242187 | 0.696 | 1.242187 | 0.889 | 0.715 |
| Other | ENO1 | 0.845 | 1.199331 | 0.69 | 1.199331 | 0.978 | 0.894 |
| Other | P4HA1 | 0.832 | 1.239505 | 0.664 | 1.239505 | 0.741 | 0.175 |
| Other | TRMT112 | 0.825 | 0.918451 | 0.65 | 0.918451 | 0.926 | 0.735 |
| Other | RPS13 | 0.822 | 0.756328 | 0.644 | 0.756328 | 0.993 | 0.998 |
| Other | TPT1 | 0.817 | 0.840456 | 0.634 | 0.840456 | 0.993 | 0.998 |
| Other | SEC61G | 0.812 | 0.841716 | 0.624 | 0.841716 | 0.963 | 0.881 |
| Other | PGK1 | 0.809 | 1.333477 | 0.618 | 1.333477 | 0.881 | 0.803 |
| Other | GADD45A | 0.802 | 1.332596 | 0.604 | 1.332596 | 0.741 | 0.3 |
| Other | ST13 | 0.801 | 0.866714 | 0.602 | 0.866714 | 0.963 | 0.878 |
| Neural crest | TAGLN3 | 0.922 | 1.681741 | 0.844 | 1.681741 | 1 | 0.686 |
| Neural crest | PBX3 | 0.917 | 1.457984 | 0.834 | 1.457984 | 0.878 | 0.154 |
| Neural crest | CRABP1 | 0.886 | 2.63702 | 0.772 | 2.63702 | 0.892 | 0.257 |
| Neural crest | MEG3 | 0.872 | 2.436136 | 0.744 | 2.436136 | 0.824 | 0.289 |
| Neural crest | ACTG1 | 0.851 | 0.573491 | 0.702 | 0.573491 | 1 | 1 |
| Neural crest | MIAT | 0.82 | 1.008958 | 0.64 | 1.008958 | 0.932 | 0.671 |
| Neural crest | KCNQ1OT1 | 0.818 | 1.242528 | 0.636 | 1.242528 | 0.905 | 0.547 |
| Neural crest | NEAT1 | 0.806 | 0.991861 | 0.612 | 0.991861 | 0.865 | 0.427 |
| Neural crest | ELAVL2 | 0.806 | 0.728978 | 0.612 | 0.728978 | 0.932 | 0.464 |
| Neural crest | RGMB | 0.804 | 1.190676 | 0.608 | 1.190676 | 0.703 | 0.168 |

Figure 5B:
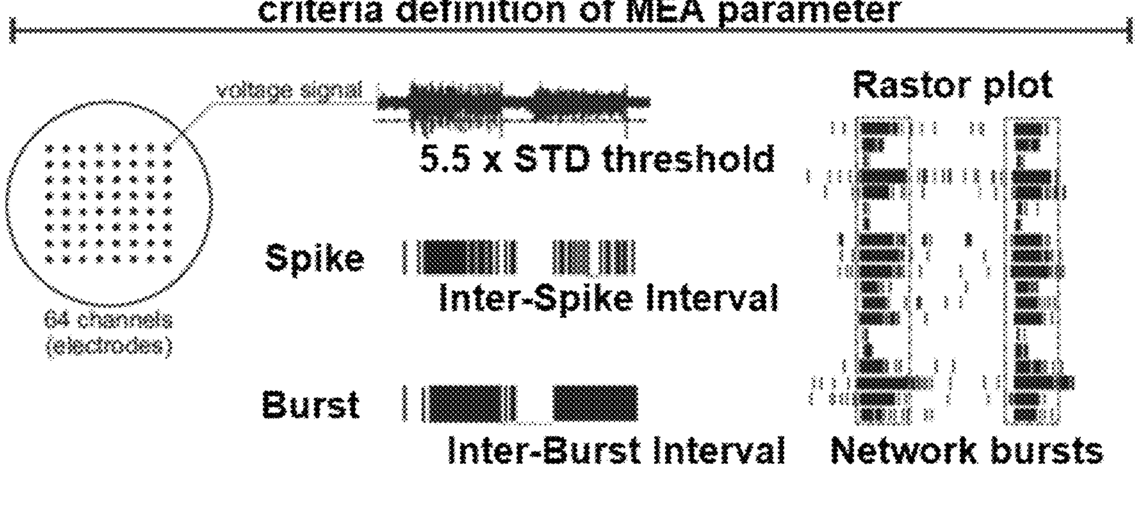
Figure 5C:
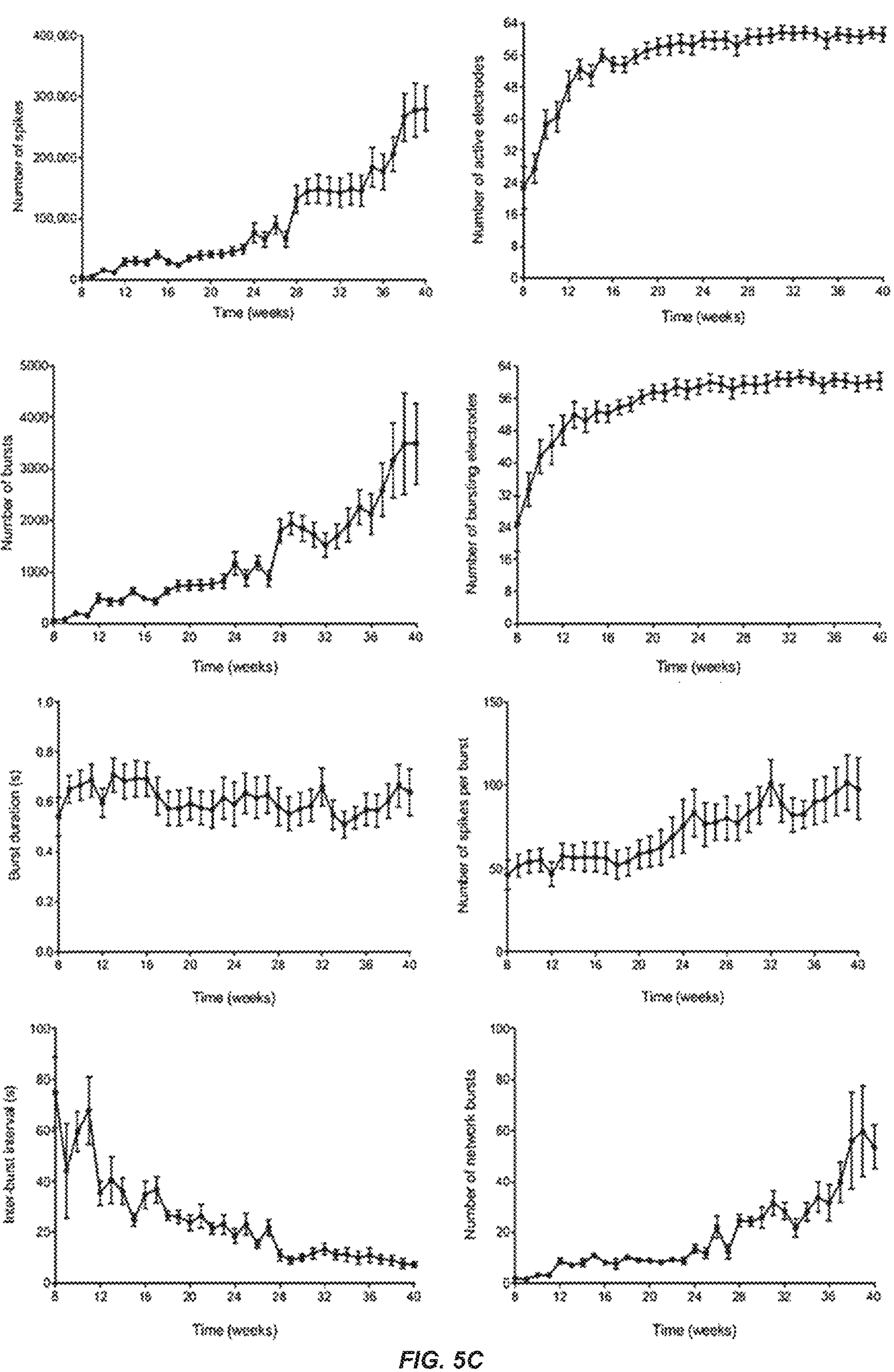
Figure 5C:
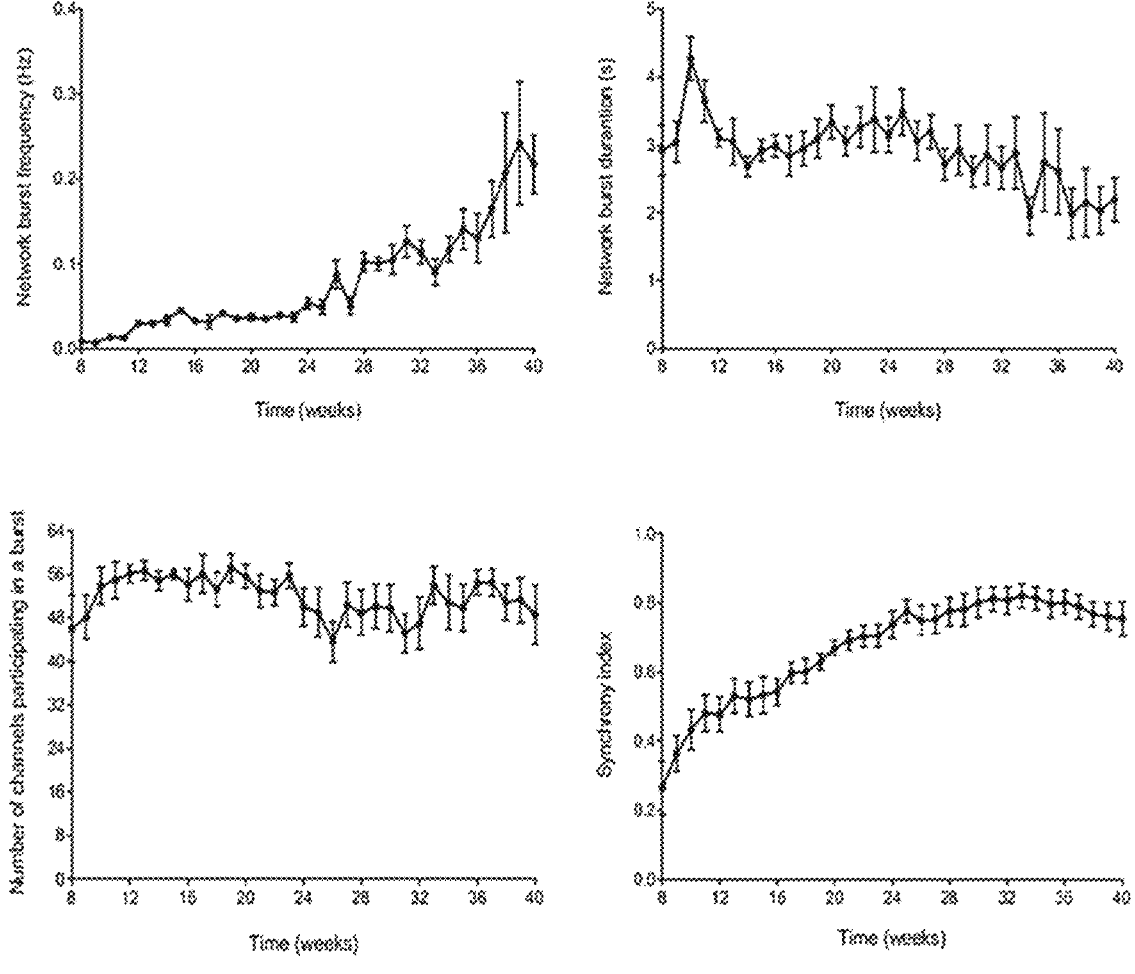
Figure 5D:
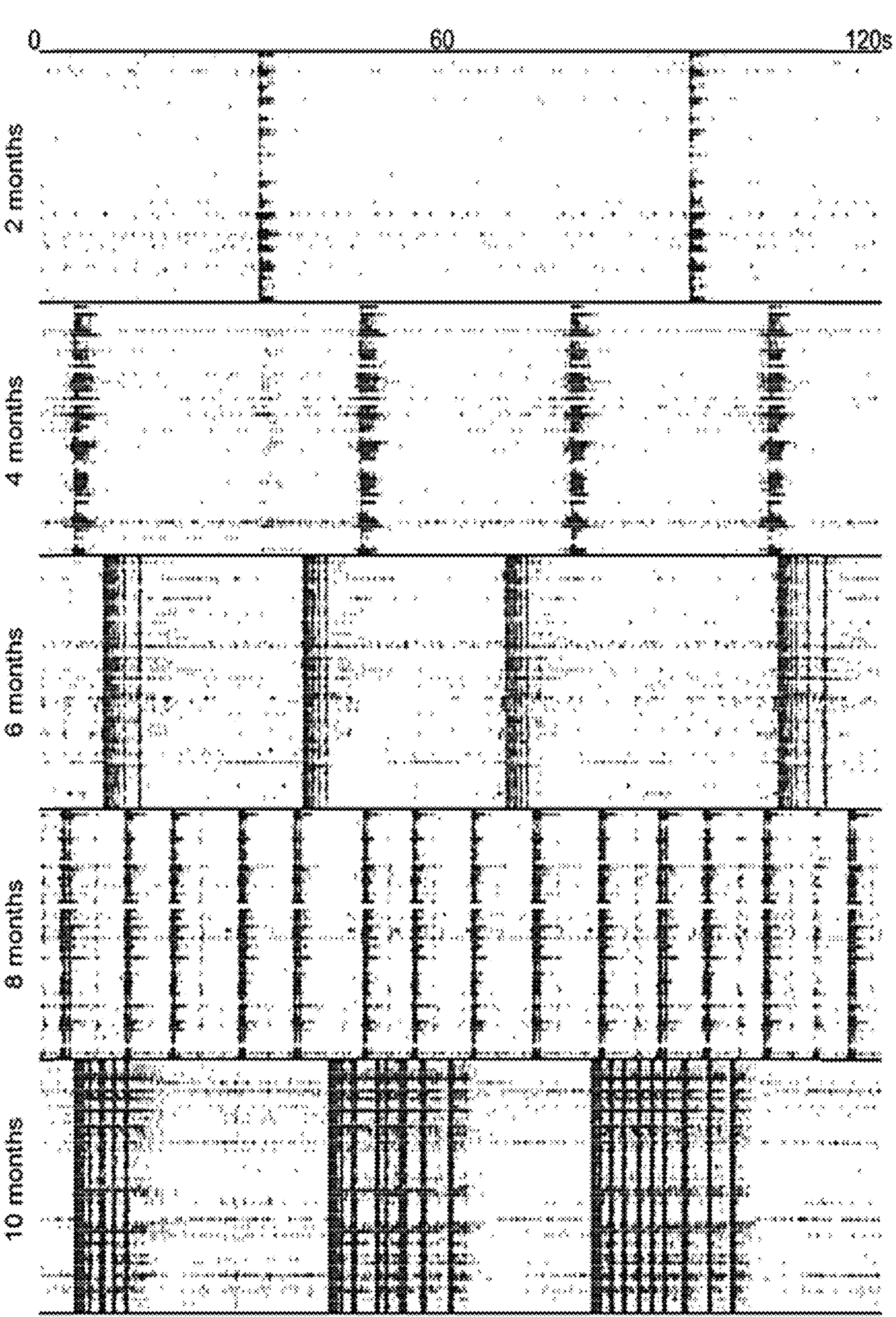
Figure 5E:
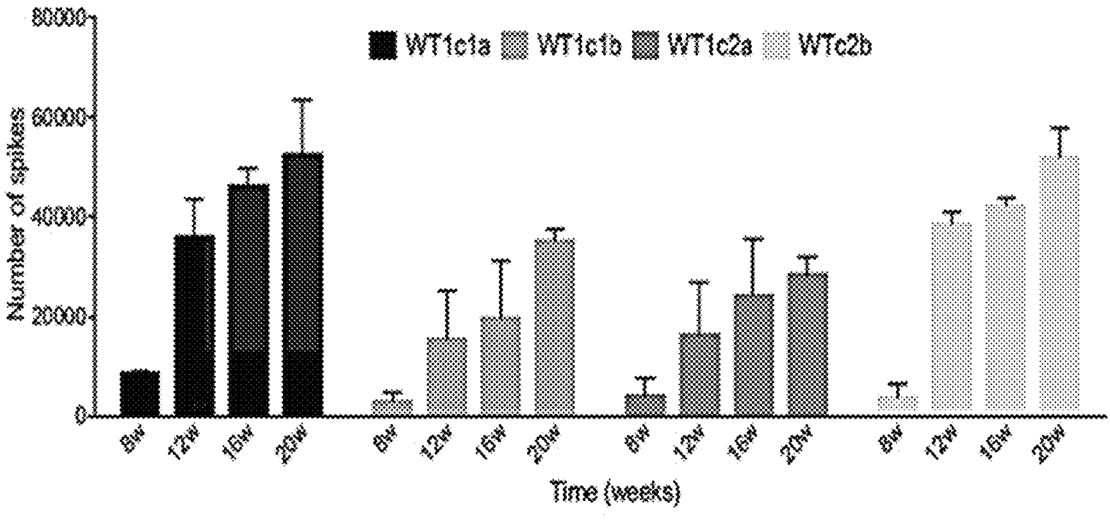
Figure 5E:
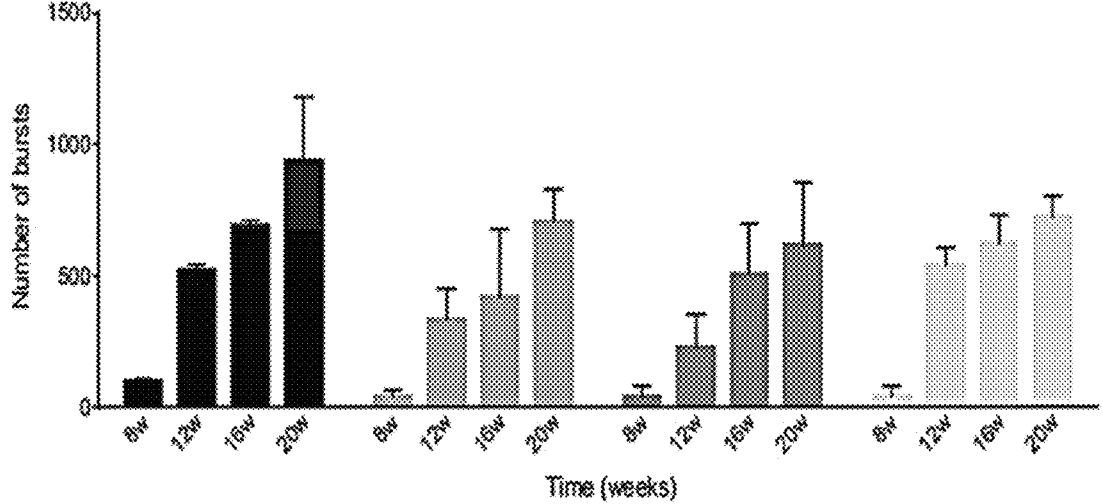
Figure 5E:
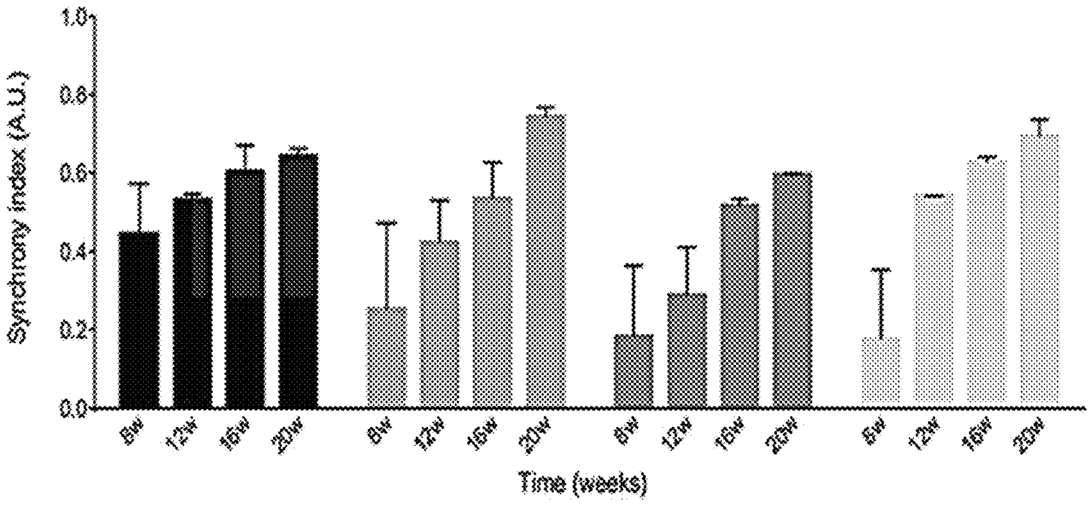

Emergence of complex oscillatory network activity. Considering the observed cellular diversity, increased expression of synaptic markers, and enhanced maturity of the generated neurons, the presence of functional network activity was further interrogated (e.g., see FIG. 3A). Neuronal activity was first evaluated by live calcium imaging, measured directly in the whole organoid. Neurons in the intact organoid showed a higher frequency of spontaneous calcium transients compared to neurons in 2D monolayer cultures (e.g., see FIG. 3B-D). Single-cell neural activity was evaluated by live calcium imaging in 6-week-old organoids. The neurons showed sparse activity with a higher frequency of spontaneous calcium transients compared to monolayer cultures (e.g., see FIG. 3). Concurrently, weekly extracellular recordings of spontaneous electrical activity using multi-electrode arrays (MEA) were performed. Single-channel and population (whole-well, n=8) firing characteristics derived from channel-wise spike times were separately analyzed, as well as the local field potential (LFP); a measure of aggregate synaptic currents and other slow ionic exchanges (e.g., see FIG. 4A). Over the course of 10 months, organoids exhibited consistent increases in electrical activity, as parametrized by channel-wise firing rate, burst frequency, and spike synchrony, which indicates a continually-maturing neural network (e.g., see FIG. 4B-E and FIG. 5). Organoid firing rates were far higher than previously observed in studies using iPSC-derived neurons or brain organoids and were ultimately comparable to rodent and primate brain activity (e.g., see FIG. 6). Additionally, the variability between replicates over 40 weeks of differentiation was significantly lower compared to iPSC-derived neurons in monolayer cultures (e.g., see FIG. 4C (inset) and FIG. 5E).

A single action potential in the presynaptic terminal often fails to evoke a postsynaptic response. Bursts of spikes increase the reliability of communication between neurons due to transmitter release facilitation, and have a special role in synaptic plasticity, neural signaling and information processing. In the cortical organoids, the increase of firing rate was accompanied by higher burst frequencies. Although bursts exhibited similar durations, the inter-burst interval was reduced over time. Synchronized events encompassing the entire network, occurring repetitively with stable spatiotemporal firing patterns, progressively changed during the maturation process (e.g., see FIG. 4G). Therefore, the reduced variability and improvement in reproducibility among cortical organoids, compared to monolayer neuronal cultures and other cerebral organoids, were evident not only at the cellular and morphological levels, but also functionally. Distinct cell lines exhibited similar patterns of differentiation and electrical activity over time (e.g., see FIG. 1B, FIG. 5E and Table 1). Additional network electrophysiological parameters are detailed in FIG. 5B.

Next, the population-level signals, typically observed in in vivo electrophysiology. were observed to further probe the functional network properties of the cortical organoid cultures. Specifically, in addition to the total network population firing rate derived from channel-wise spike times, the LFP was analyzed, a measure of aggregate synaptic currents and other slow ionic exchanges. During individual recordings, cultures displayed robust patterns of activity, switching between long periods of quiescence and short bursts of spontaneous network-synchronized spiking (hereafter referred to as "network events").

Early in the cortical organoid development (~2 months), network events rarely occurred and decayed monotonically after the initial onset; which was also reflected in the small-amplitude bipolar deflection in the LFP waveform (e.g., see FIG. 4F, left panel). From 4-months onwards, a secondary peak emerged 300-500 ms after the initial network activation, leading to the presence of a fast oscillatory (2-3 Hz) pattern up to 6-months in culture (e.g., see FIG. 4H and FIG. 7). Previous studies using rodent primary neuronal cultures observed the existence of slow periodic network events (sub-1 Hz), sometimes referred to as Giant Depolarizing Potentials (GDPs), that are indicative of single-cell bursting. Notably, this fast timescale oscillation was not observed in 3D neurospheres, and the overall activity was reduced and less sustained compared to organoids, suggesting that the spherical arrangement of neurons is not sufficient for the development of oscillations (e.g., see FIG. 8). The regular oscillatory activity during network events transitioned to stronger, yet more variable, oscillations over time. To quantify this network complexity, the regularity (coefficient of variation, CV) and the spatial and temporal correlation between spontaneous network events were tracked. The inter-event interval CV consistently increased over 10 months of differentiation (e.g., see FIG. 4I), from extremely regular latencies (CV≅0) at 2 months to irregular. Poisson-like (CV≅1) at 10 months. This indicates increased variability between consecutive network events initiation. Additionally, spatial and temporal irregularity on a shorter time-scale (within-event) also increased with development, suggesting a breakdown of deterministic population dynamics from the onset of network events.

Up to 25 weeks, the number of subpeaks steadily increased over time (e.g., FIG. 7H), along with higher amplitudes and more frequent occurrences of network events (e.g., see FIG. 7), denoting a strengthening of the oscillatory network. The primary peak that marks the onset of network events remained the time of maximum population firing and increased for up to 30 weeks. The subsequent peaks continued to increase in amplitude relative to the first peak during the course of development, indicating a continued recruitment of downstream neurons into the oscillatory network (e.g., FIG. 7D). Remarkably. at 4 months, consistent and self-similar oscillatory structures in both population firing and LFP were observed, which was robust across replicates (e.g., FIG. 7B).

Total and oscillatory activity increased in cortical organoids, which also displayed an augment in the complexity of network activity. After 6 months, robust and invariant oscillatory activity during network events transitioned to become stronger and more variable over time (e.g., FIG. 4F). The number of peaks in the oscillatory event decreased, but the amplitude of each peak continued to increase. As a measure of network complexity, the regularity of spontaneous network events (coefficient of variation, CV, of inter-event intervals) were tracked along with the spatial and temporal correlation between network events over time. The CV of the inter-event interval increased consistently, indicating greater variability of network event initiation (e.g., FIG. 7I). Across all pairs of the 64 LFP channels, the spatial event similarity (mean absolute value of the pair-wise channel correlation coefficient during network events) showed an initial increase for up to 24 weeks (e.g., FIG. 7F). This observation likely reflects the increased connectivity and physical growth of the network over the electrode array. However, the spatial similarity of the LFP decreased in the subsequent weeks, indicating that it was not simply a measure of increased extracellular ionic diffusion. Instead, this finding suggests spatially varying patterns of activity within the same network event.

When comparing the population spiking waveform of one event to another (temporal similarity) within the same recording, a remarkable consistency during early development was observed (e.g., see FIG. 7G). Namely, each time a network event occurred. it occurred in an extremely similar way (e.g., see FIG. 4F). Unlike spatial similarity, the temporal similarity of the firing pattern reliably decreased with development, suggesting a breakdown of deterministic dynamics from the onset of network events. Taken together, the electrophysiological data revealed the development of the cortical organoid cultures across different network states: from a simple network with extreme rigidity and regularity, to one that acquires repetitive, perhaps overly-regular oscillatory patterns, until it finally reaches a stage of higher spatiotemporal complexity and variability that is more similar to the network observed in developed cortical tissue (e.g., see FIG. 7G).

Based on the detection of slow extracellular signals in the LFP, network-level dynamics in the organoids to human brain tissue in vitro and in vivo were compared (e.g., see FIG. 12A). At this stage, the organoid LFP does not exhibit the full temporal complexity observed in human electrocorticography (e.g., see FIG. 12A, 4th panel), but notable resemblances do exist. In particular, EEG from extremely preterm infants (<30 months conceptional age) has been shown to display an electrophysiological signature known as trace discontinu, where quiescent periods are punctuated by brief high-amplitude fluctuations in the 1-4 Hz range. These quiescent periods quickly disappear as the child ages (with the exception of "burst suppression" during general anesthesia), but brief bursts of oscillatory activity are still a prominent feature in adult electrophysiology and are distinctly visible in the data trace. Similar bouts of bursting activity were observed between silent periods in a culture of human fetal brain tissue (e.g., see FIG. 12A. 3rd panel). Additionally, the time-frequency representation of network events in organoids resembled that of oscillatory bursts in fetal tissue and adult ECoG traces, with power localized to the low frequencies and often concentrating within a narrow oscillatory band (e.g., see FIG. 12C).

Periodic oscillatory activity is often defined as a "bump" over the characteristic $1/f$ background noise in the power spectral density (PSD) of extracellular signals above-and-beyond the aperiodic $1/f$ signal. In organoid LFPs, both prominent oscillatory peaks in the low-frequency range (1-4 Hz), as well as the aperiodic signal characteristic of neural recordings were observed. The development of oscillatory activity in cortical organoids over time was quantified by computing the PSD for each LFP recording (e.g., see FIG. 4J and FIG. 12B). Oscillatory power in the delta range (1-4 Hz) increased for up to 24 weeks in culture, tapering off slightly in subsequent recordings and plateauing during the last 10 weeks. This inverted-U trajectory reflects the network's initial acquisition of oscillatory modes at steady frequencies and the dispersion of this regularity at later time points. Using only event latency, event peak spiking, and oscillatory power, and their respective square roots, a linear regression model achieved an extremely good fit for individual organoids ($R^2$=0.919±0.017. root mean square error (RMSE)=18.2±1.8 days. mean±s.e.m.). Furthermore, regression models trained on the same unnormalized features across all organoids achieved high prediction accuracy ($R^2$=0.849±0.025, RMSE=41.3±6.1 days, leave-one-out cross-validation), indicating the consistent development of network electrophysiological features across organoids. The LFP results reveal the development of the cortical organoid cultures across different network states: from sparse activity with extreme rigidity and regularity, to one that acquires repetitive, perhaps overly-regular oscillatory patterns, until it finally reaches a stage of higher spatiotemporal complexity and variability that is more similar to the oscillatory networks observed in the human electrophysiology (e.g., see FIG. 4K and FIG. 7C-G).

Oscillatory coordination of neural ensembles and its synaptic mechanisms. Oscillatory dynamics in the functioning brain have been postulated to coordinate spiking across neural ensembles. In the LFP and other mesoscopic brain signals, this manifest as a phenomenon known as cross-frequency phase-amplitude coupling (PAC), wherein the high-frequency content of the LFP is entrained to the phase of slow oscillations. PAC in the neocortex and hippocampus has been shown to be functionally relevant in a range of behaviors and neurological disorders. In the organoids, greater PAC between oscillatory delta (1-4 Hz) and broadband gamma activity (200-400 Hz) during network events was observed in comparison to quiescent periods (e.g., see FIG. 9A-C). This result suggests that oscillations in the organoid mimic dynamics relevant for the intact brain and may serve as a model to understand the fundamental mechanisms behind the emergence of oscillatory networks in the developing human brain.

The role of glutamatergic and GABAergic synaptic transmission in forming oscillations by pharmacological intervention were further evaluated. Neuronal network activity in the absence of external stimulation suggests the presence of intrinsically active neurons in the cortical organoids. In order to evaluate the functionality of chemical synapses. 8-month-old organoids were exposed to selected compounds. Similar to primary cultures, the neuronal networks were susceptible to both glutamate receptor antagonists (AP5 and CNQX; NMDA and AMPA/kainate, respectively) and GABA receptor agonists (muscimol. GABAA; baclofen, GABAB) by significantly reducing the number of bursts, with a subsequent extinction of synchronous activity. In contrast, the GABA receptor antagonist bicuculline increased burst activity with no impact on synchrony indexes. The effect of pharmacological treatments on network activity was reversed after the drug washout (e.g., see FIG. 9E). Neuronal electrical activity was blocked in the presence of tetrodotoxin (TTX) (e.g., see FIG. 9D-E). Notably, blockade of GABAergic transmission by bicuculline increased the number of network-synchronized events and did not affect peak population firing rates, but abolished oscillatory activity by erasing subsequent reverberant peaks (e.g., FIG. 9F). Therefore, the main excitatory and inhibitory neurotransmitter systems of the human cortex are present and involved in the establishment of a synchronized network in cortical organoids. Further, the data suggests that GABA transmission is crucial for the maintenance, but not the initiation of oscillatory activity. This is consistent with accounts of inhibition rhythmically coordinating pyramidal populations activity during early development.

The data demonstrate the in vitro electrophysiological dynamic formation in cortical organoids compared to the developed human brain. The current results suggest that cortical organoids represent a first step towards an in vitro model that captures the complex spatiotemporal and oscillatory dynamics of the human brain. Different from other studies, a robust neural activity was stablished at earlier stages and progressively culminate in a complex EEG-like oscillatory network. Given the potential roles of synchronized oscillations in coordinating the information flow between developed cortical brain regions during human cognition, these results illustrate the potential to advance future studies in functional electrophysiology, brain development, and genetic neural disorders by leveraging the natural, emergent development of complex neural activity in cortical organoids.

MECP2 is important for the timely emergence of network oscillations. In addition to modeling the typically-developing brain, cortical organoids can also shed light on the mechanism behind functional deficits in neurodevelopmental disorders. Normal oscillatory network dynamics in the brain are often shown to break down in psychiatric and neurological conditions. However, the mechanisms by which that happens and its impact on the circuit are difficult to elucidate. Thus, whether cortical organoids could be used to model oscillatory network defects was next investigated since previous work evidenced that patients with autism spectrum disorder exhibit reduced alpha oscillation power (8-12 Hz) and evoked gamma (40-60 Hz) response, as well as reduced PAC. Mutations in the Methyl-CpG-binding protein 2 (MECP2) gene lead to a severe disruption in cortical development that account for many symptoms of Rett syndrome, autism, schizophrenia and other neurological disorders. MECP2 is involved in the epigenetic regulation of target genes by binding to methylated CpG dinucleotides promoter regions, acting as a transcriptional modulator (e.g., see FIG. 10A).

To model MECP2 deficiency during neurodevelopment, a pluripotent cell model was generated using two different cell lines, each carrying a distinct MECP2 mutation that lead to a nonfunctional protein (e.g., see FIG. 13). Human MECP2-mutant neurons in vitro exhibit fewer synapses, smaller soma size, altered calcium signaling and electrophysiological defects compared to controls. Based on the observed reduction in the number of layer V neurons in Mecp2-mutant mice and documented clinical data of microcephaly in Rett syndrome patient, transcriptomics, cellular and structural differences using MECP2-KO cortical organoids were examined. The delay in the maturation process was accompanied by a significant decrease in the diameter of MECP2-KO organoids, spine density and synaptic puncta at later stages of differentiation (e.g., see FIG. 10B-D). Additionally, a significant reduction in the proportion of CTIP2+ and SATB2+ neurons was observed by targeted single-cell analysis (e.g., see FIG. 10E-G) and corroborated by immunostaining (e.g., see FIG. 10H). MECP2-KO cortical organoids also showed reduced neural activity leading to an absence of network oscillations, which supports a delay in the maturation process (e.g., see FIG. 10I-J). The inability to entrain into a functionally connected network at early stages of development might underlie the core deficits found in MECP2-deficient related disorders. More importantly, these results highlight the contribution of specific genes in the formation of a network circuitry and the emergence of oscillatory activity.

Organoid network development recapitulates preterm EEG. Despite similarities between the complex oscillatory network activity in organoids and the in vivo brain, it is unclear whether the spontaneous developmental trajectory observed is representative of programmed early human neurodevelopment. While network activity from organoids do not exhibit the full temporal complexity seen in adults, the pattern of alternating periods of quiescence and network-synchronized events is similar to human electrophysiological signatures present in preterm infant EEG (See Table 3). During trace discontinu, quiescent periods are punctuated by high-amplitude oscillations (spontaneous activity transients, SATs) lasting a few seconds. Intervals of complete quiescence disappear as infants become of term, and the EEG is dominated by continuous and low-amplitude desynchronized activity in adult brains (e.g., see FIG. 14A). The time-frequency representation of network events in organoids also resembled the oscillatory bursts in preterm EEG, with power localized in the low frequencies and often accentuated within a narrow oscillatory band (e.g., see FIG. 15A-B).

TABLE 3

Electrophysiological features in preterm neonatal EEG dataset and analogous features computed in organoid LFP.

| Neonatal EEG features | Computed organoid LFP features |
|---|---|
| Envelope (50%) | None |
| Envelope (5%) | None |
| Envelope (95%) | None |
| rEEG (50%) | None |
| rEEG (5%) | None |
| rEEG (95%) | None |
| SATs per hour | Network Events per hour |
| RMS SAT duration | RMS network event duration |
| SAT duration (50%) | Network event duration (50%) |
| SAT duration (5%) | Network event duration (5%) |
| SAT duration (95%) | Network event duration (95%) |
| RMS Inter-SAT Duration | RMS Inter-event Duration |
| Inter-SAT duration (50%) | Inter-event duration (50%) |
| Inter-SAT duration (5%) | Inter-event duration (5%) |
| Inter-SAT duration (95%) | Inter-event duration (95%) |
| Temporal Theta Power | None |
| Activation Synchrony Index | None |
| Interhemispheric Correlation | None |
| Total Spectral Power | None |
| Relative Delta Power | Relative Delta Power |
| Relative Theta Power | Relative Theta Power |
| Relative Alpha Power | Relative Alpha Power |
| Relative Beta Power | Relative Beta Power |

Shaded cells indicate features used in the age-prediction model.

In order to quantitatively compare network activity in cortical organoids to preterm human EEG, a machine learning model (ElasticNet) was trained (with cross-validation) on a dataset of 567 neonates EEGs. A subset of features relating to SATs were computed from preterm neonatal EEGs (24-38 post-conception weeks, PCW). After training, 9 analogous features computed from organoid LFPs were submitted to the model and those features were asked with predicting organoid "brain age" over time (e.g., see FIG. 14B). Notably, the mean model-generated organoid "brain age" was indistinguishable from its "true age" (in vitro) after 28 weeks (e.g., see FIG. 14C). In other words, organoids past 28 weeks in culture share similar developmental trajectories of electrophysiological features to preterm neonates. Next, the similarities between organoids and preterm humans were examined by looking at each specific feature (e.g., see FIG. 14C-D). Of the 9 features, "SATs per hour" ("events per hour" in organoids) showed strikingly similar values and growth, while "root-mean-square SAT duration" showed a similar decline (but not in absolute value) over 25 to 38 weeks in both datasets (e.g., see FIG. 14E and FIG. 15A-B). Therefore, while the developmental trajectory of cortical organoids is not identical to the fetal brain, a machine learning model trained only on neonatal EEG features was able to predict organoid culture age, demonstrating that the observed network electrophysiological features may indeed be representative of genetically programmed developmental timelines.

Zika virus preferentially infects and kills brain tumor stem cells. The potential of using ZIKV to achieve preferential anti-tumor efficacy against GSCs was investigated. Using human iPSC-derived neural stem/progenitor cells (hereafter called NPCs) and patient-derived GSCs, it was found that ZIKV infected both normal and neoplastic stem-like neural cells, but GSCs were more likely to be infected than normal NPCs, as quantified by both ZIKV envelope protein immunofluorescence (e.g., see FIG. 16A) and ZIKV viral RNA by PCR (e.g., see FIG. 16B). Although the infection of GSCs was moderately higher than normal NPCs, ZIKV induced potent cell death in GSCs relative to normal NPCs (e.g., see FIG. 16D-E). ZIKV induced differences in cell number through induction of apoptotic cell death, as measured by cleaved CASPASE 3 (e.g., see FIG. 16E). These results were validated in a panel of five GSC cultures and five NPC cultures from different genetic backgrounds (e.g., see FIG. 17).

Glioblastomas represent the brain cancer for which the tumor hierarchy is most clearly delineated, but other brain tumors, especially pediatric brain tumors, contain stem-like tumor cells. Therefore, the anti-tumor efficacy of ZIKV was interrogated against a panel of brain tumor cells—two pediatric pontine gliomas, four medulloblastomas, an ependymoma, and two meningiomas—grown under serum-free conditions to enrich for stem-like populations. For all models except the meningiomas. ZIKV induced potent apoptotic cell death (e.g., see FIG. 18). Of note, unlike the other tumor types tested, meningioma is not intrinsic to the brain parenchyma; it is posited to arise from the arachnoid granulations. Collectively, these results support preferential killing of stem-like brain tumor cells, supporting its potential utility as a platform for an oncolytic virus.

ZIKV preferentially targets glioblastoma organoid growth more than cerebral organoids. Leveraging the generation of cerebral organoids, a system to study glioblastoma heterogeneity was developed. To avoid species differences, the relative effects of ZIKV infection on glioblastoma and normal cerebral organoids was determined. Glioblastoma organoids progressively grow over time, as measured by organoid diameter (e.g., see FIG. 19). Supporting the functional importance for integrin $\alpha_v\beta_5$ in glioblastoma growth, glioblastoma organoids incubated with an integrin $\alpha_v\beta_5$ blocking antibody displayed stasis or reduced size over time. In contrast, glioblastoma organoids infected with ZIKV were obliterated upon ZIKV infection, an effect that was lost upon treatment with the integrin $\alpha_v\beta_5$ blocking antibody (e.g., see FIG. 19). As normal comparisons, mature cerebral organoids from human pluripotent stem cells were generated, as previously described, which displayed substantially lower expression of integrin $\alpha_v\beta_5$ than in the glioblastoma organoids (e.g., see FIG. 21B and FIG. 20A). ZIKV had little effect on the size of normal cerebral organoids over time (e.g., see FIG. 20B).

Generation of human glioblastoma-cerebral organoid models. To directly test the relative efficacy of ZIKV infection against human glioblastoma relative to toxicity to normal human brain, grown in mature (6-month-old) human cerebral organoids (corticoids) were implanted with human glioblastoma tumors. After six months, most of the NPCs have differentiated into neurons and astrocytes. Two GFP-labeled patient-derived GSC cultures were independently fused with existing corticoids. Mimicking tumor growth, the GFP-positive glioblastoma cells invaded the corticoids and expanded over time (e.g., see FIG. 21A). Similar to the results above, the GFP-labeled glioblastoma cells preferentially expressed SOX2 and integrin $\alpha_v\beta_5$ relative to the normal corticoid cells (e.g., see FIG. 21B). These results demonstrate that fused glioblastoma-corticoid models preserve the differential expression profiles found in human tumors and normal brain and offer a platform to study human glioblastoma in a species-matched system.

ZIKV infection preferentially targets GSCs in glioblastoma-corticoid models. Using the glioblastoma-corticoid models to study the effects of ZIKV infection in a species matched background, the combined structures were infected and confirmed that ZIKV infected the integrin $\alpha_v\beta_5$ marked populations, as measured by ZIKV envelope protein immunohistochemistry. Comparing ZIKV infection of normal corticoids and glioblastoma-corticoids, ZIKV infected integrin $\alpha_v\beta_5$-positive combined glioblastoma-corticoids to a far greater degree (e.g., see FIG. 21D). ZIKV infection of the combined glioblastoma-corticoids greatly reduced the number of GFP-labeled tumor cells (e.g., see FIG. 21C). In two patient-derived GSC models fused with human corticoids, ZIKV showed a potent anti-tumor effect over time (e.g., see FIG. 21C, FIG. 21E and FIG. 22). In conclusion, these results demonstrate that Zika serves as an oncolytic virus with specific activity against glioblastoma stem cells in association with preferential expression of integrin $\alpha_v\beta_5$ in a fully humanized model system.

A number of embodiments have been described herein. Nevertheless, it will be understood that various modifications may be made without departing from the spirit and scope of this disclosure. Accordingly, other embodiments are within the scope of the following claims.

What is claimed is:

1. An in vitro method of generating functional cortical organoids from neural progenitor cells (NPCs) comprising:

culturing NPCs in serum-free supplemented neurobasal media comprising brain-derived neurotrophic factor (BDNF), glial cell-derived neurotrophic factor (GDNF), neurotrophin 3 (NT-3), a fibroblast growth factor, L-ascorbic acid, and dibutyryl-cAMP to generate functional cortical organoids, wherein the functional cortical organoids are able to produce periodic and regular spontaneous network events upon differentiation, and a frequency and an amplitude of the network events increases over time.

2. The method of claim 1, wherein the fibroblast growth factor is FGF2.

3. The method of claim 1, wherein the cortical organoids are comprised predominantly of proliferative neural progenitor cells (NPCs) that have self-organized into a polarized neuroepithelium-like structure.

4. The method of claim 1, wherein the method further comprises:

differentiating the functional cortical organoids in serum-free supplemented neurobasal media for at least 60 days.

5. The method of claim 4, wherein the functional cortical organoids comprise a proliferative region that is surrounded by intermediate progenitor cells expressing TBR2 and deep cortical layer markers TBR1 and CTIP2 and wherein cortical plate folding is observed in the cortical organoids.

6. The method of claim 1, wherein the method further comprises: differentiating the functional cortical organoids in serum free supplemented neurobasal media for at least 300 days and up to 2 years.

7. The method of claim 6, wherein the functional cortical organoids comprise pyramidally-shaped neurons, dendritic spines and structurally defined synapses.

8. The method of claim 1, wherein the NPCs are differentiated from stem cells comprising the steps of:

i) culturing stem cells in feeder-free media comprising inhibitors for bone morphogenetic protein (BMP) and transforming growth factor-β (TGF-β) pathways;

SEQUENCE LISTING

```
Sequence total quantity: 3
SEQ ID NO: 1            moltype = DNA  length = 30
FEATURE                 Location/Qualifiers
source                  1..30
                        mol_type = genomic DNA
                        organism = Homo sapiens
SEQUENCE: 1
tcccccaaac agcggcgctc catcatccgt                                   30

SEQ ID NO: 2            moltype = DNA  length = 30
FEATURE                 Location/Qualifiers
source                  1..30
                        mol_type = other DNA
                        organism = synthetic construct
SEQUENCE: 2
tcccccaaat agcggcgctc catcatccgt                                   30

SEQ ID NO: 3            moltype = DNA  length = 29
FEATURE                 Location/Qualifiers
source                  1..29
                        mol_type = other DNA
                        organism = synthetic construct
SEQUENCE: 3
tcccccaaca gcggcgctcc atcatccgt                                    29
```

(ii) subculturing the stem cells of (i) in suspension under rotation in the presence of a ROCK inhibitor to form free-floating spheres;

(iii) culturing the free-floating spheres in serum-free supplemented neurobasal media comprising inhibitors for BMP and TGF-β pathways to obtain neuronal progenitor cells (NPCs); and (iv) expanding/proliferating the NPCs by first culturing the NPCs in serum-free supplemented neurobasal media comprising a fibroblast growth factor (FGF) in the absence of epidermal growth factor (EGF) and then culturing the NPCs in serum-free supplemented neurobasal media comprising the FGF and EGF.

9. The method of claim 8, wherein the stem cells are induced pluripotent stem cells.

10. The method of claim 9, wherein the induced pluripotent stem cells are obtained from fibroblasts.

11. The method of claim 10, wherein the fibroblasts are obtained from a subject having a neurological disease, disorder or syndrome.

12. The method of claim 8, wherein for (i) the inhibitors for BMP and TGF-β pathways comprise SB431542 and Dorsomorphin.

13. The method of claim 8, wherein for (iv) the fibroblast growth factor is FGF2.

14. The method of claim 8, wherein for (iv) the NPCs are first cultured in serum-free supplemented neurobasal media comprising an FGF for seven days and then cultured for seven days in serum-free supplemented neurobasal media comprising an FGF and EGF.

* * * * *